10

(12) United States Patent
Laskowitz et al.

(10) Patent No.: US 8,093,209 B2
(45) Date of Patent: Jan. 10, 2012

(54) METHODS OF SUPPRESSING MICROGLIAL ACTIVATION AND SYSTEMIC INFLAMMATORY RESPONSES

(75) Inventors: Daniel T. Laskowitz, Chapel Hill, NC (US); William D. Matthew, Durham, NC (US); Michael McMillian, Rareton, NJ (US)

(73) Assignee: Cognosci, Incorporated, Research Triangle Park, NC (US)

( * ) Notice: Subject to any disclaimer, the term of this patent is extended or adjusted under 35 U.S.C. 154(b) by 0 days.

(21) Appl. No.: 12/328,625

(22) Filed: Dec. 4, 2008

(65) Prior Publication Data

US 2009/0185997 A1 Jul. 23, 2009

Related U.S. Application Data

(62) Division of application No. 10/252,120, filed on Sep. 23, 2002, now abandoned.

(51) Int. Cl.
*A61K 38/16* (2006.01)
*A61P 31/00* (2006.01)
(52) U.S. Cl. .......................... 514/1.4; 530/324; 530/326
(58) Field of Classification Search .......................... None
See application file for complete search history.

(56) References Cited

U.S. PATENT DOCUMENTS

| | | | |
|---|---|---|---|
| 4,902,505 A | 2/1990 | Pardridge et al. |
| 5,017,566 A | 5/1991 | Bodor |
| 5,168,045 A | 12/1992 | Dyer et al. |
| 5,182,364 A | 1/1993 | Dyer et al. |
| 5,204,327 A | 4/1993 | Kiyota et al. |
| 5,473,039 A | 12/1995 | Dyer et al. |
| 5,604,198 A | 2/1997 | Poduslo et al. |
| 5,686,416 A | 11/1997 | Kozarich et al. |
| 6,245,751 B1 | 6/2001 | Crutcher et al. |
| 6,605,588 B1 | 8/2003 | Lee et al. |

FOREIGN PATENT DOCUMENTS

| | | |
|---|---|---|
| EP | 0297456 A2 | 1/1989 |
| WO | WO 92/10512 | 6/1992 |
| WO | WO 95/06456 | 3/1995 |
| WO | WO 97/14437 | 4/1997 |
| WO | WO 98/01101 | 1/1998 |
| WO | WO 99/08701 A1 | 2/1999 |
| WO | WO 99/16464 A1 | 4/1999 |
| WO | WO 99/45950 | 9/1999 |
| WO | WO 03/026479 A2 | 4/2003 |
| WO | WO 03/026479 A3 | 4/2003 |

OTHER PUBLICATIONS

Miwa et al. JP200217579, Aug. 8, 2000 (English translation).*
Aono, et al., "Protective Effects of Peptides Corresponding to the Receptor Binding Region of Apolipoprotein E on NMDA Excitotoxicity in Primary Neuronal-Glial Cultures", Trip Report: 31$^{st}$ Annual Meeting of the Society for Neuroscience, San Diego, California (Nov. 2001).

Barger, et al., "Microglial Activation by Alzheimer Amyloid Precursor Protein and Modulation by Apolipoprotein E", Nature 388: 878-881 (Aug. 1997).
Benazzouz, et al., "Riluzole Prevents MPTP-induced Parkinsonism in the Rhesus Monkey: A Pilot Study," *Eur. J. Pharmacol.* 284:299-307 (1995).
Bowie, et al., "Deciphering the message in protein sequences: tolerance to amino acid substitutions", Science, 247: 1306-1310 (1990).
Cardin, et al., "Inhibition of Lymphocyte Proliferation b Synthetic Peptides Homologous to Human Plasma Apolipoproteins B and E", Biochemical and Biophysical Research Communications, 154: 741-745 (Jul. 1998).
Champe, et al., "IV. Tertiary Structure of Globular Proteins," "V. Quaternary Structure of Proteins," "VI Denaturation of Proteins," and "VII. Protein Misfolding," pp. 18-21 in *Lippincott's Illustrated Reviews: Biochemistry*, 3rd Ed. Lippincott Williams & Wilkins, Philadelphia, Pennsylvania, USA (2005).
Chen, et al., "Motor and Cognitive Deficits in Apolipoprotein E Deficient Mice After Closed Head Injury," Neuroscience 80:1255-1262 (1997).
Christie, et al., "Expression of the Very Low-Density Lipoprotein Receptor (VLDL-r), an Apolipoprotein-E Receptor, in the Central Nervous System and in Alzheimer's Disease", Journal of Neuropathology and Experimental Neurology, 55(4): 491-498 (1996).
Clay, et al., "Localization of a Domain in Apolipoprotein E with Both Cytostatic and Cytotoxic Activity", Biochemistry, 34: 11142-11151 (1995).
Crutcher, et al., "Neurite degeneration elicited by apolipoprotein E peptides", Experimental Neurology 130(1):120-126 (1994).
Dong, et al., "Enhanced binding activity of an apolipoprotein E mutant, APO E5, to LDL receptors on human fibroblasts", Biochemical & Biophysical Research Communications 168(2):409-414 (Apr. 1990). Dong, et al., "Site-directed mutagenesis of an apolipoprotein E mutant, apo E5(Glu3—Lys) and its binding to low density lipoprotein receptors", Biochemical & Biophysical Research Communications I87(2):1180-1186 (Sep. 1992).
Dyer, et al., "A Synthetic Peptide Mimetic of Plasma Apolipoprotein E that Binds the LDL Receptor", Journal of Biological Chemistry, 266: 22803-22806 (Dec. 1991).
Dyer, et al., "Only Multimers of a Synthetic Peptide of Human Apolipoprotein E Are Biologically Active", Journal of Biological Chemistry, 266: 15009-15015 (1991).
Gordon, et al., "Derangement in Stress Response of Apolipoprotein E-deficient Mice," *Neuroscience Letters* 206:212-214 (1996).
Holtzman, et al., "Low density lipoprotein receptor-related protein mediates apolipoprotein E-dependent neurite outgrowth in a central nervous system-derived neuronal cell line", Proc. Natl. Acad. Sci. USA, 92: 9480-9484 (1995).

(Continued)

*Primary Examiner* — Daniel E Kolker
*Assistant Examiner* — Stacey MacFarlane
(74) *Attorney, Agent, or Firm* — Cooley LLP

(57) ABSTRACT

Methods of suppressing the activation of microglial cells in the Central Nervous System (CNS), methods of ameliorating or treating the neurological effects of cerebral ischemia or cerebral inflammation, and methods of combating specific diseases that affect the CNS by administering a compound that binds to microglial receptors and prevents or reduces microglial activation are described. ApoE receptor binding peptides that may be used in the methods of the invention are also described, as are methods of using such peptides to treat peripheral inflammatory conditions such as sepsis. Also described are methods of screening compounds for the ability to suppress or reduce microglial activation.

6 Claims, 16 Drawing Sheets

OTHER PUBLICATIONS

Innerarity, et al., "Binding of arginine-rich (E) apoprotein after recombination with phospholipid vesicles to the low density lipoprotein receptors of fibroblasts", Journal of Biological Chemistry 254(10):4186-4190 (1979).

International Search Report for PCT/US99/05221 (mailed Nov. 3, 1999).

Jordan, et al., "Isoform-Specific Effect of Apolipoprotein E on Cell Survival and β-Amyloid-induced Toxicity in Rat Hippocampal Pyramidal Neuronal Cultures," J. Neurosci. 18:195-204 (1998).

Lalazar, et al., "Site-specific Mutagenesis of Human Apolipoprotein E", Journal of Biological Chemistry, 263: 3542-3545 (1988).

Laskowitz, et al., "Endogenous apolipoprotein E suppresses LPS-stimulated microglial nitric oxide production", Neuroreport. 9(4):615-618 (1998).

Laskowitz, et al., "Apolipoprotein E and the CNS response to injury", Journal of Cerebral Blood Flow & Metabolism 18(5): 465-471 (1998).

Laskowitz, et al., "Apolipoprotein E suppresses glial cell secretion of TNF alpha", Journal of Neuroimmunology 76(1-2):70-74, (1997).

Laskowitz, et al., "Apolipoprotein E-deficient mice have increased susceptibility to focal cerebral ischemia", Journal of Cerebral Blood Flow & Metabolism 17(7):753-758 (1997).

Laskowitz, et al., "Downregulation of Microglial Activation by Apolipoprotein E and ApoE-Mimetic Peptide", Experimental Neurology, 167: 74-85 (2001).

Ludwig, "Supplementary European Search Report," 3 pages, from EP Appl. No. 02775888.7, European Patent Office, Munich, Germany (mailed Mar. 9, 2007).

Marzolo, et al., "Expression of α2-Macroglobulin Receptor/ Low Density Lipoprotein Receptor-Related Protein (LRP) in Rat Microglial Cells," J. Neurosci. Res. 60:401-411 (2000).

Mickle, et al., "Genotype-phenotype relationships in cystic fibrosis", Med. Clin. North Am., 84 (3): 597-607 (May 2000).

Misra, et al., "Apolipoprotein E and Mimetic Peptide Initiate a Calcium-Dependent Signaling Response in Macrophages", Journal Leukocyte Bio. 70: 677-683 (2001).

Mrak, et al., "Glial Cytokines in Alzheimer's Disease: Review and Pathogenic Implications", Hum. Pathol. 26: 816-823 (Aug. 1995).

Pardridge, "Chapter 12: Blood-brain barrier peptide transport and peptide delivery to the brain, Peptide-based drug design", Ed. Taylor et al., American Chemical Society, 265-296 (1995).

Tolar, et al., "Truncated Apolipoprotein E (ApoE) Causes Increased Intracellular Calcium and May Mediate ApoE Neurotoxicity," J. Neuroscience 19(16): 7100-7110 (1999).

Vitek, et al., "Modulation of nitric oxide production in human macrophages by apolipoprotein-E and amyloid-beta peptide", Biochemical & Biophysical Research Communications 240(2):391-394 (1997).

Voet, et al., Biochemistry, John Wiley & Sons, Inc., 126-128 and 228-234 (1990).

Weisgraber, et al., "The receptor-binding domain of human apolipoprotein E. Monoclonal antibody inhibition of binding", Journal of Biological Chemistry 258(20):12348-12354 (1983).

Yan, et al., "Two-amino acid molecular switch in an epithelial morphogen that regulates binding to two distinct receptors", Science, 290: 523-527 (2000).

Zielasek, et al., Advances in Neuroimmunology, 6 (2): 191-222 (1996).

McEwen, "Allostasis, Allostatic Load, and the Aging Nervous System: Role of Excitatory Amino Acids and Excitotoxicity", Neurochemical Research, 25: 1219-1231 (2000).

Pitt et al., "Glutamate excitotoxicity in a model of multiple sclerosis," Nature Medicine, vol. 6(1): 67-70, 2000.

Hall et al., "Beta-interferon and multiple sclerosis," Trends Neurosci., vol. 20: 63-67, 1997.

Examination Report for EP Application No. 02775888.7-2107 (mailed Sep. 21, 2010).

Huang et al., "Apolipoprotein E fragments present in Alzheimer's disease brains induce neurofibrillary tangle-like intracellular inclusions in neurons," Proc. Natl. Acad. Sci. USA, vol. 98: 8838-8843, Jul. 17, 2001.

Tolar, et al., "Neurotoxicity of the 22 kDa Thrombin-Cleavage Fragment of Apolipoprotein E and Related Synthetic Peptides Is Receptor-Mediated," J. Neuroscience, vol. 17: 5678-5686, Aug. 1, 1997.

Tikka and Koistinaho, "Minocycline Provides Neuroprotection Against N-Methyl-D-aspartate Neurotoxicity by Inhibiting Microglia," J. Immunol., vol. 166: 7527-7533, 2001.

* cited by examiner

METHODS OF SUPPRESSING MICROGLIAL ACTIVATION AND SYSTEMIC INFLAMMATORY RESPONSES

RELATED APPLICATION INFORMATION

This application is a divisional of U.S. patent application Ser. No. 10/252,120, filed Sep. 23, 2002, now abandoned, the disclosure of which is incorporated by reference herein in its entirety.

GOVERNMENT SUPPORT

This invention was made with Government support under NIH grants NS368087-01A2, K08NS01949, and RO3AG16507-01. The Government has certain rights to this invention.

FIELD OF THE INVENTION

The present invention relates to methods of suppressing the activation of microglial cells in the Central Nervous System (CNS), methods of reducing or suppressing the activation of glial or microglial cells, methods of ameliorating or treating the neurological effects of cerebral ischemia or cerebral inflammation, methods of combating specific diseases that affect the CNS by administering a compound that binds to microglial receptors and prevents or reduces microglial activation, and methods of screening compounds for the ability to prevent or reduce microglial activation. The invention further relates to the methods of suppressing glutamate excitotoxicity and neuronal cell death associated with N-methyl-D-aspartate (NMDA) exposure, as well as methods for suppressing systemic inflammatory responses such as those seen in sepsis.

BACKGROUND OF THE INVENTION

The Central Nervous System (CNS) has long been considered to be a site of relative immune privilege. However, it is increasingly recognized that CNS tissue injury in acute and chronic neurological disease may be mediated by the CNS inflammatory response. The CNS inflammatory response is primarily mediated by inflammatory cytokines.

The microglial cell is the primary immunocompetent cell in the central nervous system. Microglia are morphologically, immunophenotypically and functionally related to cells of the monocyte/macrophage lineage (Gehrmenn et al., 1995). Acute CNS insult, as well as chronic conditions such as HIV encephalopathy, epilepsy, and Alzheimer's disease (AD) are associated with microglial activation (McGeer et al., 1993; Rothwell and Relton, 1993; Giulian et al., 1996; Sheng et al., 1994). Microglial activation results in the production of nitric oxide (NO) and other free radical species, and the release of proteases, inflammatory cytokines (including IL-1β, IL-6 and TNFα), and a neurotoxin that works through the NMDA receptor (Giulian et al., 1996). Microglial activation can be assessed by measuring the production of nitrite, a stable product of nitric oxide formation (Barger and Harmon, 1997).

Apolipoprotein E (ApoE) plays a role in cholesterol metabolism and has also been reported to have immunomodulatory properties. For instance, ApoE has been demonstrated to have immunomodulatory effects in vitro, including suppression of lymphocyte proliferation and immunoglobulin synthesis after mitogenic challenge (Avila et al., 1982; Edgington and Curtiss, 1981). ApoE is secreted in large quantities by macrophage after peripheral nerve injury, and by astrocytes and oligodendrocytes (glial cells) after CNS injury (Stoll et al., 1989; Stoll and Mueller, 1986). The role that ApoE plays in glial activation and CNS injury, however, remains controversial.

The majority of ApoE is produced in the liver. However, due to its large size, ApoE does not readily cross the blood-brain barrier. In fact, following liver transplantation, peripheral apoE phenotype changes to that of the donor liver, while CSF (cerebrospinal fluid) apoE phenotype remains unchanged (Linton et al., 1991). Thus, ApoE localized within the nervous system represents a discrete pool from protein produced in the periphery (Laskowitz et al., January 2001).

ApoE is a 299 amino acid lipid-carrying protein with a known sequence (Rail et al., *J. Biol. Chem.* 257:4174 (1982); McLean et al., *J. Biol. Chem.* 259:6498 (1984)). The complete gene for human ApoE has also been sequenced (Paik et al., *Proc. Natl. Acad. Sci. USA* 82:3445 (1985). ApoE sequences from at least ten species have been determined, and show a high degree of conservations across species, except at the amino and carboxyl termini. Weisgraber, *Advances in Protein Chemistry* 45:249 (1994).

Human ApoE is found in three major isoforms: ApoE2, ApoE3, and ApoE4; these isoforms differ by amino acid substitutions at positions 112 and 158. The most common isoform is ApoE3, which contains cysteine at residue 112 and arginine at residue 158; ApoE2 is the least common isoform and contains cysteine at residues 112 and 158; ApoE4 contains arginine at residues 112 and 158. Additional rare sequence mutations of human ApoE are known (see, e.g., Weisgraber, *Advances in Protein Chemistry* 45:249 (1994), at page 268-269).

ApoE has two distinct functional domains, a 10-kDa carboxyl terminus and a 22 k-Da amino terminus (Wetterau et al., 1988). The carboxyl terminus has a high affinity for lipid and mediates the role of ApoE in cholesterol transport. The amino terminus is composed of four antiparallel alpha helices, which includes the receptor binding region (Weisbarger et al., 1983; Innerarity et al., 1983). ApoE is known to bind a family of cell surface receptors, including the LDL, VLDL, LRP/α2M, ER-2, LR8 receptors, apoE receptor 2 (apoER2), and megalin/gp330 (Kim et al., 1996; Novak et al., 1996; Veinbergs et al., 2001). The interaction of apolipoprotein E and the LDL receptor is important in lipoprotein metabolism. In studies of the LDL receptor-binding activity of ApoE, it is typically complexed with phospholipid. The protein has been described as essentially inactive in the lipid-free state (Innerarity et al., 1979).

One region of ApoE which is critical for the interaction with the LDL receptor lies between residues 140-160 (Mahley, 1988), and site-specific mutagenesis studies of this region have demonstrated that mutations affecting charge and conformation can result in defective binding (Lalazar, 1988). The receptor binding region of ApoE (i.e., amino acid residues 135-160) is rich in basic amino acids including arginine and lysine. Various amino acid substitutions in the receptor binding region of ApoE have been studied for their effects on ApoE-LDL receptor binding. Substitution of either arginine or lysine at residues 136, 142, 145 and 146 with neutral residues decreased normal ApoE3 binding activity (Weisgraber, 1988). No single substitution of a basic residue within the receptor-binding region of ApoE3 completely disrupts LDL receptor binding, suggesting that no one residue is critical for this interaction. It has been postulated that regions of ApoE outside the LDL binding region are necessary to maintain the receptor-binding region in an active binding conformation (Weisgraber, 1994). Dyer et al. (1991) studied lipid-free synthetic peptide fragments comprising residues 141-

155 of ApoE, and a dimeric peptide of this sequence. No binding activity was observed with the monomer of this peptide, but low levels of binding were observed with the dimer (~1% of LDL activity).

The receptors that bind ApoE have areas of high sequence similarity. The scavenger receptor is known to be present on microglia, and preferentially binds acetylated and oxidized LDL. The scavenger receptor may be particularly relevant under inflammatory (oxidizing) conditions. Scavenger receptors are also known to be upregulated in microglia after injury (Bell et al., 1994).

LRP receptors are known to be present on macrophages. In overview, following modification by lipoprotein lipase and the association of apolipoproteins, very large density lipoproteins (VLDL) and chylomicron become remnants, and are cleared hepatically by a receptor-mediated mechanism. Although recognized as distinct from the low density lipoprotein (LDL) receptor, the remnant receptor also has a high affinity for ApoE, and recognizes the remnant particles via incorporated ApoE moieties. In 1988, this remnant receptor was cloned, and dubbed the LDL receptor-related related protein, or "LRP".

The LRP is a large receptor, with a primary sequence of 4525 amino acids, and bears many structural similarities to other members of the LDL receptor family. Like the LDL receptor, the extracellular domain of LRP includes a cysteine-enriched ligand binding domain and EGF precursor homology domain which are believed to play a role in the acid-dependent dissociation of ligand from the receptor. Unlike the LDL receptor, however, the O-lined sugar domain is not present in the extracellular portion adjacent to the membrane. As with all of the members of the LDL receptor family, LRP is a transmembrane protein, and is anchored by a single transmembrane segment. The cytoplasmic tail of the protein is 100 amino acids, approximately twice as long as the LDL receptor, and contains the NpxY motif, which is believed to be necessary for targeted coated-pit mediated endocytosis (Krieger and Herz, 1994; Misra et al., 1994).

In addition to binding lipid, ApoE also binds lipopolysaccharide (LPS), which is an endotoxin that mediates Gram-negative sepsis by inducing the production of macrophage-derived cytokines. These cytokines, which include TNFα, IL-1α, IL-1β and IL-6, are responsible for the metabolic and physiologic changes that ultimately lead to pathology (Waage et al., 1987; Chensue et al., 1991: Henderson et al., 1996). ApoE redirects bound LPS from macrophages to parenchymal liver cells, which mediate the subsequent secretion of LPS into the bile where it is inactivated (Harris et al., 1993; Harris et al., 1998). Consequently, macrophages become less activated and produce less of the proinflammatory mediators.

Laskowitz et al. (June 1997) described experiments in which mixed neuronal-glial cell cultures from apoE-deficient mice were stimulated with lipopolysaccharide (LPS). It was found that preincubation of the cell cultures with apoE blocked glial secretion of TNFα in a dose-dependent manner. More recently, Van Oosten et al. demonstrated that concomitant administration of ApoE with a lethal dose of LPS protected mice against LPS-induced mortality (Van Oosten et al., 2001). Rensen et al. demonstrated that a free ApoE molecule binds approximately two molecules of LPS, possibly by an exposed hydrophilic domain involving arginine residues since selective elimination of the positive charge on arginine residues of apoE resulted in a largely reduced binding of LPS to ApoE and abolished the effect of ApoE on the in vivo behavior of LPS (Rensen et al., 1997). Interestingly, lactoferrin is a glycoprotein with an arginine/lysine-rich sequence at positions 25-31 resembling the receptor binding site (amino acids 142-148) of ApoE, and has also been shown to bind LPS (Huettinger et al., 1988; Cohen et al., 1992; Miyazawa et al., 1991). Although, he showing by Laskowitz et al. that preincubation of ApoE with neuronal-glial cell cultures blocked LPS-induced TNF-alpha tion whereas coadministration of ApoE with LPS did not suggests that some other mechanism than LPS binding is involved (Laskowitz et al., June 1997).

In addition to its roles in cholesterol metabolism and endotoxin clearance, ApoE may also play an important role in neurological disease. The presence of ApoE4 has been associated with risk of developing sporadic and late-onset Alzheimer's disease (Strittmatter et al., 1993). Barger and Harmon (August 1997) reported that treatment of microglia with a secreted derivative of beta-amyloid precursor protein (sAPP-alpha) activated microglia, induced inflammatory reactions in microglia, and enhanced the production of neurotoxins by microglia. The ability of sAPP-alpha to activate microglia was blocked by prior incubation of the sAPP-alpha protein with apolipoprotein E3 but not apolipoprotein E4. More recently, some researchers have proposed an involvement of ApoE in regulating Tau phosphorylation, suggesting that ApoE is involved some way in the development of the neurofibrillary fibrils associated with Alzheimer's Disease (Flaherty et al., 1999; Tesseur et al., 2000). However, the link between ApoE and Tau has remained controversial (Lovestone, 2001).

There have also been numerous clinical and experimental observations demonstrating that ApoE modifies the response of brain to acute injury. For example, clinical observations suggest that the ApoE4 allele is associated with increased mortality and functional deficit after acute and chronic closed head injury (Sorbi et al., 1995; Teasdale et al., 1997; Jordan et al., 1997; Friedman et al., 1999). The ApoE4 allele has also been associated with the extent of amyloid β-protein deposition following head injury (Mayeux et al., 1995; Nicoll et al., 1995).

The deleterious effects of the apoE4 isoform on neurological outcomes have also been observed in a variety of clinical settings associated with cerebral ischemia. These include stroke (Slooter et al., 1997), intracranial hemorrhage (Alberts et al., 1995; McCarron et al., 1998), cognitive deficit after cardiopulmonary bypass (Tardiff et al., 1997) and hypoxic brain injury following cardiac arrest resuscitation (Schiefermeier et al., 2000). The role of ApoE following focal ischemia is less clear, however, with at least one clinical study failing to document an effect of apoE genotype on functional outcome following stroke (Broderick et al., 2001).

Clinical observations implicating a role for apoE in modifying the central nervous system response to ischemia have recently been extended to animal models. ApoE deficient mice have larger infarcts and worse functional outcomes following focal ischemia and reperfusion relative to control animals matched for age, sex, and genetic background (Laskowitz et al., July 1997).

This effect is independent of cerebral blood flow or cerebrovascular anatomy (Bart et al., 1998). In models of transient forebrain ischemia, apoE deficient animals also have increased injury to neuronal populations that are selectively vulnerable to cerebral hypoperfusion, including hippocampus, caudoputamen, and cortex (Sheng et al., 1999; Horsburgh et al., 1999). This increased sensitivity to ischemia can be reversed by intraventricular administration of human recombinant apoE (Horsburgh et al., 2000). Moreover, consistent with the clinical literature, apoE deficient mice expressing the human apoE4 transgene have larger infarcts and worse functional outcomes than mice expressing the human apoE3 transgene (Sheng et al., 1998).

Although there are multiple clinical reports demonstrating that apoE genotype influences neurological recovery in isoform-specific fashion, the mechanisms by which this occur remain poorly defined. It has been proposed that endogenous apoE may influence the CNS response to injury by modifying oxidative stress (Miyata and Smith, 1996), exerting direct neurotrophic effects (Holtzman et al., 1995), downregulating the CNS inflammatory response (Lynch et al., 2001), or serving as a pathological chaperone by promoting cerebral amyloid deposition (Wisniewski and Frangione, 1992). More recent studies, however, have failed to demonstrate any neuroprotective effect from the intact ApoE protein (Jordan et al., 1998; Lendon et al., 2000).

Furthermore, several studies have suggested that ApoE derived peptide fragments may cause neuronal injury. For example, it has recently been demonstrated that carboxyl-terminal truncated forms of apoE occur in the brains of patients with AD, presumably as a result of intracellular processing. These fragments are bioactive and are capable of interacting with cytoskeletal proteins to induce inclusions resembling neurofibrillary tangles in cultured neurons (Huang et al., 2001). Moulder et al. recently reported that a dimer composed of the ApoE-derived peptide 141-155 has a neurotoxic effect, suggesting to the authors that ApoE itself could be a source of toxicity in Alzheimer's disease brain (Moulder et al., 1999). Using a peptide comprised of a tandem repeat of residues 141-149, Tolar et al. demonstrated that exposure of primary hippocampal neurons to this peptide induced neuronal cell death, an effect which was blocked by preincubation with MK-801, an NMDA antagonist (Tolar et al., 1999). These results predict that exposure with this tandem repeat peptide amplifies NMDA-induced excitotoxicity by direct or indirect mechanisms.

In summary, ApoE plays varied roles in different biological processes. While ApoE appears to provide a protective effect in the periphery by removing LPS from macrophages, the role it plays in CNS injury and neurological diseases such as Alzheimer's Disease is far from clear. What is needed is a better understanding of how ApoE contributes to the CNS inflammatory response, to aide in the formulation of reagents for use in the treatment of neurological injury and disease.

SUMMARY OF THE INVENTION

The present invention is based on the finding that microglial activation can be reduced or suppressed using peptides that comprise the receptor binding site sequence of Apolipoprotein E. Thus, the present invention provides methods and compositions for treating CNS disease states in which glial or microglial activation occurs, and in which glial or microglial activation contributes to the deleterious signs and/or symptoms associated with the specific disease state.

The present invention is further based on the unexpected finding that peptides derived from the receptor-binding region of ApoE completely suppress the neuronal cell death and calcium influx associated with N-methyl-D-aspartate exposure. This result is in contrast to recent reports in the literature that ApoE enhances the NMDA-induced excitotoxicity, a surprising result which provides the basis for ApoE-based formulations and treatments for injury and diseases associated with activation of glutamate receptors such as the NMDA receptor.

The present invention is further based on the unexpected finding that peptides derived from the receptor-binding region of ApoE protect against LPS-induced production of TNFα and IL-6 in an in vivo sepsis model, a finding that is surprising in view of the fact that the receptor-binding fragments of the present invention contain only a small portion of the intact protein. Thus, the present invention provides methods and compositions for treating sepsis using the peptides of the present invention, as well as any compound identified using the methods disclosed herein that binds to the same receptor as the peptides of the present invention.

The present invention is further based upon the identification and characterization of the LRP/α2M as a high affinity Apolipoprotein E receptor, a characterization which is the basis for several of the diagnostic assays and kits disclosed herein. The assays of the invention may be performed using any ApoE receptor, including but not limited to the LRP/α2M, LDL, VLDL, ER-2, LR8, apoER$_2$ and megalin/gp 330 receptors.

In view of the foregoing, one aspect of the present invention is a method of suppressing glial or microglial activation, either in vitro or in a mammalian subject, by administering a compound or composition containing a compound that binds to glial or microglial cells or other effector cells such as astrocytes at the receptor bound by the peptides of the present invention, and particularly the peptides of SEQ ID Nos 3, 4, 5, 6 and 10. The compound or composition is administered in an amount that reduces glial or microglial activation compared to activation that would occur in the absence of the compound. Suitable compounds include the peptides of the present invention, which may be formulated into pharmaceutical compositions comprising one or more of the peptides alone or in combination with other pharmaceutical compounds relevant for suppressing glial or microglial activation.

A further aspect of the present invention is a method of ameliorating symptoms associated with CNS inflammation by administering a compound or a composition containing a compound that binds to glial or microglial cells at the receptor bound by the peptides of the present invention, and particularly the peptides of SEQ ID Nos 3, 4, 5, 6 and 10. The compound or composition is administered in an amount that reduces CNS inflammation as compared to that which would occur in the absence of the compound. Suitable compounds include the peptides of the present invention, which may be formulated into pharmaceutical compositions comprising one or more of the peptides alone or in combination with other pharmaceutical compounds relevant for suppressing CNS inflammation.

A further aspect of the present invention is a method of ameliorating symptoms associated with CNS or cerebral ischemia in a subject, by administering a compound or a composition containing a compound that binds to glial or microglial cells at the LRP/α2M receptor or at the receptor bound by the peptides of the present invention, and particularly the peptides of SEQ ID Nos 3, 4, 5, 6 and 10. The compound or composition is administered in an amount that alleviates symptoms associated with CNS ischemia as compared to that which would occur in the absence of the compound. Suitable compounds include the peptides of the present invention, which may be formulated into pharmaceutical compositions comprising one or more of the peptides alone or in combination with other pharmaceutical compounds relevant for alleviating CNS ischemia.

A further aspect of the present invention is a method of reducing neuronal cell death associated with glutamate excitotoxicity or NMDA exposure in a mammalian subject by administering to said subject a compound or a composition containing a compound that binds to glial or microglial cells at the receptor bound by the peptides of the present invention, and particularly the peptides of SEQ ID Nos 3, 6 and 10. The compound or composition is administered in an amount that reduces neuronal cell death associated with glutamate toxicity as compared to reduction that would occur in the absence of the compound. Suitable compounds include the peptides of the present invention, which may be formulated into pharmaceutical compositions comprising one or more of the peptides alone or in combination with other pharmaceutical compounds relevant for suppressing glutamate toxicity.

A further aspect of the present invention is a method of suppressing macrophage activation in a mammalian subject, by administering a compound or a composition containing a compound that binds to macrophage cells at the LRP/α2M receptor or at the receptor bound by the peptides of the present invention, and particularly the peptides of SEQ ID Nos 3, 6 and 10. The compound or composition is administered in an amount that suppresses macrophage activation as compared to activation that would occur in the absence of the compound. Suitable compounds include the peptides of the present invention, which may be formulated into pharmaceutical compositions comprising one or more of the peptides alone or in combination with other pharmaceutical compounds relevant for suppressing macrophage activation.

A further aspect of the present invention is a method of treating atherosclerosis or of reducing the formation of atherosclerotic plaques, comprising administering a compound or a composition containing a compound that binds to macrophage cells at the receptor bound by the peptides of the present invention, and particularly the peptides of SEQ ID Nos 3, 4, 5, 6 and 10. The compound or composition is administered in an amount that reduces the formation of artherosclerotic plaques as compared to that which would occur in the absence of the compound. Suitable compounds include the peptides of the present invention, which may be formulated into pharmaceutical compositions comprising one or more of the peptides alone or in combination with other pharmaceutical compounds relevant for reducing the formation of atherosclerotic plaques.

A further aspect of the present invention is a method of treating or of reducing the inflammation associated with bacterial sepsis, comprising administering a compound or a composition containing a compound that binds to macrophage cells at the receptor bound by the peptides of the present invention, and particularly the peptides of SEQ ID Nos 3, 4, 5, 6 and 10. The compound or composition is administered in an amount that reduces sepsis-associated inflammation as compared to that which would occur in the absence of the compound. Suitable compounds include the peptides of the present invention, which may be formulated into pharmaceutical compositions comprising one or more of the peptides alone or in combination with other pharmaceutical compounds relevant for treating sepsis.

A further aspect of the present invention is a therapeutic peptide of SEQ ID NO: 3, or a dimer of two peptides wherein each peptide comprises SEQ ID NO:2, or a peptide of SEQ ID NO:4, SEQ ID NO:5, SEQ ID NO:6, or a peptide of SEQ ID NO:10, and pharmaceutical compositions thereof. Also included are compounds identified using the assays disclosed in the present invention, wherein such compounds bind to the receptor bound by the peptides of the invention and mediate the functional effects disclosed herein. Consistent therewith, the invention also includes use of the disclosed peptides and compounds and functional variants thereof in methods of making medicaments for treating the various diseases and disorders discussed herein. Such medicaments may comprise the subject peptides and compounds of the invention, alone or in combination with other known pharmaceutical agents.

A further aspect of the present invention is a method of screening a compound for the ability to suppress glial or microglial activation by incubating an activated glial or microglial cell culture with the compound, and then measuring a marker of microglial activation such as nitric oxide.

A further aspect of the present invention is a method of screening a compound for the ability to suppress glial or microglial activation, by pre-incubating a glial or microglial cell culture with the compound; incubating the cell culture with a known activator of glia or microglia; and then measuring a marker of glial or microglial activation.

A further aspect of the present invention is a method of screening a test compound for the ability to suppress glial or microglial activation, by determining whether the compound binds to glia or microglia at the same receptor to which peptides of SEQ ID NO:3 or SEQ ID No:4 or SEQ ID No:5 or SEQ ID NO:6 or SEQ ID NO:10 bind (for instance, the LRP/α2M receptor).

DETAILED DESCRIPTION OF THE INVENTION

Figure 1:
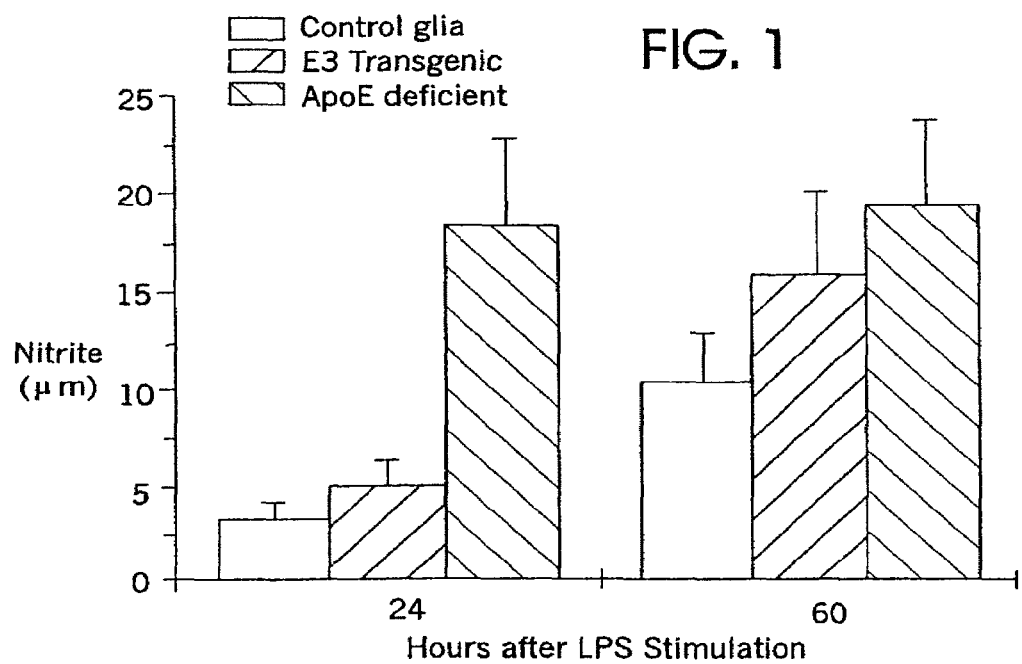
FIG. 1 graphs the production of nitrite by cultures of glial cells from ApoE-deficient mice (solid bar), ApoE3 transgenic mice (hatched bar), and control mice (white bar), after exposure to lipopolysaccharide (LPS). Responses were measured at 24 and 60 hours after stimulation of cell cultures by LPS.

The present inventors determined that apoE modulates the activation of glia in the CNS, and further identified several peptides that suppresses the activation of microglia. While not wishing to be bound to a single theory, the present inventors hypothesized that ApoE binding to a microglial receptor affects the phenotype of the microglia, decreasing the responsiveness of the microglia to various activators, and therefore decreasing the release of inflammatory compounds from the microglia that would otherwise occur in the presence of such activators. The ApoE may be binding to the same receptor as is bound by the activating compounds, or may be binding to a receptor independent from that bound by activators.

In lymphocytes, ApoE has been shown to block activation by a variety of compounds, including LPS, the lectin PHA, and anti-CD3 antibody; these activators are known to bind to distinct receptors on lymphocytes. The methods and compounds of the present invention are designed to prevent or suppress the receptor-mediated activation of microglia, and thus prevent or reduce the deleterious neurological effects associated with activated microglia. Peptides and other therapeutic molecules according to the present invention are able to bind to receptors on glia, and decrease the responsiveness of the cell to various activators. In this manner, methods and compounds according to the present invention may be used to treat, ameliorate, or prevent certain signs, symptoms, and/or deleterious neurological effects of acute and/or chronic CNS injury.

Glutamate and related excitatory amino acids are released by synapses in the mammalian brain, and activate ion channel glutamate receptors including the NMDA, AMPA (α-amino-3-hyrdoxy-5-methyl-isoxazole-4-propionate) and kainate receptors. Overstimulation of ionotropic glutamate receptors, particularly NMDA receptors, has been implicated in neuronal degeneration. Systemic administration of non-competitive inhibitors such as the NMDA receptor antagonist MK-801 prior to ischemia has been shown to prevent microglial activation, as well as delayed death of neurons, suggesting that early blockage of the glutamate cascade prevents microglial activation involved in ischemic injury (Streit et al., 1992). However, recent studies using a peptide (141-149) from the receptor binding region of ApoE suggest that such peptides amplify NMDA-induced excitotoxicity and induce neuronal cell death (Tolar et al., 1999). Other recent studies failed to demonstrate any neuroprotective effect against NMDA-induced excitotoxicity from the intact apoE protein (Jordan et al., 1998; Lendon et al., 2000).

In contrast to recent reports in the literature, the present inventors have found that ApoE exhibited a modest dose-dependent reduction in NMDA induced cytotoxicity. By comparison, a seventeen residue ApoE-mimetic peptide (SEQ ID NO:10) surprisingly exhibited a significantly more robust neuroprotection relative to native ApoE and blocked both the calcium influx and cell death associated with NMDA exposure as completely as the NMDA receptor antagonist MK-801. Further truncation of the peptide at the amino terminal resulted in a progressive loss of neuroprotection from NMDA excitotoxicity. These results suggest that one way which ApoE affects recovery of neuronal cells from ischemic injury following brain insult is by protecting cells against glutamate toxicity. Furthermore, the results support the use of ApoE-mimetic peptides as a valuable therapeutic strategy following cerebral ischemia.

The unexpected finding that ApoE peptides completely suppress the neuronal cell death and calcium influx associated with N-methyl-D-aspartate exposure provides the basis for ApoE-based formulations and treatments for disorders and diseases associated with activation of glutamate receptors which would not have been apparent before the present invention. The finding also provides the basis for combined therapeutic compositions containing one or more more of the peptides or NMDA antagonist compounds of the invention in combination with known reagents for treating diseases associated with NMDA excitotoxicity.

For instance, NMDA excitotoxicity has been associated with HIV dementia and encephalopy (Perez et al., 2001; Haughey et al., 2001; Doble, 1999). The fact that ApoE peptides work as NMDA antagonists is particularly surprising seeing as no statistically significant correlation has been found between the risk of HIV dementia or HIV encephalitis in relation to apoE genotypes (Dunlop et al., 1997). Thus, even without the recent reports that ApoE enhances NMDA show NMDA antagonistic activity.

NMDA excitotoxicity has also been associated with neurolathyrism, amyotrophic lateral sclerosis (ALS) (Doble, 1999; Nguimfack, 2002), schizophrenia, Huntington's chorea, Parkinson's (Nguimfack, 2002; Mytilineou et al., 1997; Klopman and Sedykh, 2002; Le and Lipton, 2001), bipolar disorder (Farber et al. 2002), multiple sclerosis in humans and experimental allergic encephalomyelitis (EAE) in animals (Paul and Bolton, 2002), depression, stroke (Le and Lipton, 2001), epilepsy and the inherited neurometabolic disease d-2-hydroxyglutaric aciduria (Kolker et al., 2002), in addition to Alzheimer's Disease (Bi et al., 2002; Bi and Sze, 2002) and traumatic brain injury (Rao et al., 2001; Regner et al., 2001; Xu and Luo, 2001). NMDA antagonists are also used in clinical anesthesia (Farber et al., 2002), and have been shown to inhibit chronic pain (McKenna and Melzack, 2001; Le and Lipton, 2001), drug tolerance (Cady, 2001) and alcohol dependency in an animal model (Kotlinska, 2001).

Thus, the present invention includes the use of the disclosed peptides and NMDA antagonist compounds in methods and pharmaceutical formulations for the treatment of any of the above diseases or disorders, and as ingredients in anesthesia formulations and in combined therapeutic compositions containing other known compounds useful for treating the various disorders. For instance, the peptides and other compounds of the invention may be combined with any known HIV drug, including HIV reverse transcriptase and protease inhibitors, in a combined therapeutic regimen geared toward inhibiting viral replication and preventing or treating HIV dementia, or may be administered alone or with other NMDA antagonists in a supplementary formulation. One author recently commented that, even though antiretroviral therapy of the CNS is essential for improvement in function and prognosis in patients demonstrating AIDS dementia complex, it may also be necessary in the long term to provide additional neuroprotection, blocking secondary mechanisms of neurotoxicity, since a significant portion of toxicity seems to be mediated by indirect mechanisms that continue even during antiretroviral therapy (Clifford, 2002).

Riluzole is a substance with glutamate antagonistic properties that is used for neuroprotective treatment in amyotrophic lateral sclerosis and which is currently being tested in clinical trials for treatment of Huntington's disease and Parkinson's disease (Schiefer et al., 2002; Doble, 1999). Schiefer and colleagues recently demonstrated that Riluzole prolongs survival time and alters nuclear inclusion formation in a transgenic mouse model of Huntington's disease. Thus, given the NMDA antagonistic role of the peptides and compounds of the invention, these peptides and compounds could be used in pharmaceutical formulations for the treatment of ALS, Huntington's and Parkinson's, alone or in combination with other glutamate antagonists such as Riluzole.

L-deprenyl is an inhibitor of monoamine oxidase (MAO)-B that delays the emergence of disability and the progression of signs and symptoms of Parkinson's disease, and is predicted to exert a protective effect from events occurring downstream from activation of glutamate receptors (Mytilineou et al., 1997). MAO-B inhibitors, dopamine receptor antagonists such as Levodopa and NMDA receptor antagonists have all been shown to have an antiparkinson effect, and multidrug combinations have been shown to synergistically enhance the antiparkinson effects of the drugs (Klopman and Sedykh, 2002). Thus, given the NMDA antagonistic role of the peptides and compounds of the invention, these peptides and compounds could be used in pharmaceutical formulations for the treatment of Parkinson's, alone or in combination with other NMDA receptor antagonists, MAO-B inhibitors such as L-deprenyl and dopamine receptor antagonists such as Levodopera.

The production of free radicals as a result of glutamate excitotoxicity has been implicated in the pathogenesis of schizophrenia (Nguimfack, 2002). Thus, researchers have begun to examine treatment of schizophrenia with antioxidizing substances used in other neurological diseases such as ALS, Parkinson's and Huntington's disease. Given that the NMDA receptor antagonistic peptides and compounds of the invention may be used to inhibit the production of free radicals as a result of glutamate excitotoxicity, these peptides and compounds may be used in pharmaceutical formulations for the treatment of schizophrenia, alone or in combination with other antioxidizing substances.

Anticonvulsant, antiepileptic agents that inhibit NMDA receptor hypofunction have found to be of clinical use in bipolar disorder (Farber et al., 2002). Such agents include phenyloin, carbamazepine, valproic acid, lamotrigine, riluzole, tetrodotoxin, felbamate, gabapentin and ethosuximide. Given that the peptides of the compounds of the present invention also inhibit NMDA receptor-associated neurotoxicity, the peptides and compounds of the present invention may be used alone or in combination with other NMDA receptor antagonists or inhibitors of NMDA receptor hypofunction in pharmaceuticals and methods of treating bipolar disorder or epilepsy.

Multiple sclerosis (MS) is an immunologically mediated disease, as determined by observation of the response to immunotherapy and the existence of an animal model, experimental autoimmune encephalitis. Interferon (IFN) beta-1b, IFN beta-1a, and glatiramer acetate, current therapies used for relapsing or remitting MS, have mechanisms of action that address the immunologic pathophysiology of MS (Dhib-Jalbut, 2002). For instance, the IFNs bind to cell surface-specific receptors, initiating a cascade of signaling pathways that end with the secretion of antiviral, antiproliferative, and immunomodulatory gene products. Glatiramer acetate, a synthetic molecule, inhibits the activation of myelin basic protein-reactive T cells and induces a T-cell repertoire characterized by anti-inflammatory effects. Several currently marketed treatments, including IV immunoglobulin, methotrexate, and azathioprine, are being evaluated as treatments for relapsing-remitting multiple sclerosis (RRMS) in combination with the approved therapies (Calabrese, 2002). Given that the NMDA receptor antagonist memantine has been shown to prevent and breakdown of and restore the blood-brain barrier and reduce symptoms associated with pathogenesis of EAE in vivo (Paul and Bolton, 2002), the peptides and compounds of the present invention may be used alone or in combination with other NMDA receptor antagonists or in addition to interferons or Glatiramer acetate for the treatment of MS in humans.

Using an animal model of persistent human pain, McKenna and Melzack recently showed that pain behavior was significantly reduced by treatment with the NMDA receptor antagonist AP5 (McKenna and Melzack, 2001). Similarly, Von Bergen and colleagues recently demonstrated that intrathecal administration of LY293558, a competitive non-N-methyl-D-aspartate excitatory amino acid receptor antagonist, blocked both sensory and motor responses in rats through 180 min, with complete recovery observed the following day. The effects of LY293558 were more pronounced and sustained than those of bupivacaine, leading the authors to conclude that drugs like LY293558 that block glutamate receptors may be an alternative to local anesthetics for spinal anesthesia in humans (Von Bergen et al., 2002). Thus, the peptides and compounds of the present invention may be used alone or in combination with other NMDA receptor antagonists or in addition to other anesthetic compounds as local anesthetics in humans and animals.

NMDA receptors are also believed to play a major role in the pathophysiology of substance use (Kotlinska, 2001; Soyka et al., 2000). For instance, Kotlinska showed that the NMDA receptor antagonist memantine given prior to ethanol administration prevented the development of ethanol dependence in rats. Jones and colleagues demonstrated that the intensity of morphine withdrawal syndrome was reduced in rat pups pre-treated with the NMDA receptor antagonist, LY235959. Withdrawal behaviors such as head moves, moving paws, rolling, and walking were decreased, and vocalizations were completely eliminated in pups pre-treated with LY2359559 (Jones et al., 2002). According to a recent review, strategies aimed at targeting the basic mechanisms of addiction rely on the premise that addiction is caused by adaptive changes in the central nervous system and that craving, which is the main cause of relapse, depends on dopaminergic mechanisms and requires high general excitability. Thus, pharmacological approaches have involved drugs that reduce neuronal adaptability by inhibiting the calcium entry to neurons both through voltage-gated channels (e.g. nimodipine) and NMDA receptors (e.g. memantine), as well as drugs that stimulate the inhibitory GABAergic system (gamma-vinyl-GABA, baclofen). Thus, the peptides and compounds of the present invention may be used alone or in combination with other NMDA receptor antagonists such as memantine or in addition to other neuronal adaptability compounds such as nimodipine, gamma-vinyl-GABA and baclofen in compositions and methods for the prevention and treatment of alcohol and drug addiction in humans.

The finding by the present inventors that one way in which ApoE peptides inhibit microglial activation is by inhibiting glutamate excitotoxicity lends further support to the value of these peptides and the other NMDA receptor antagonistic compounds of the invention for the treatment of CNS injury. For instance, Rao et al. reported neuroprotection by memantine, another NMDA receptor antagonist, after traumatic brain injury in rats (Rao et al., 2001). Other authors recently commented that excessive activation of NMDA receptors may be one of the most important factors to induce secondary cerebral impairments, and NMDA receptor antagonists such as AP5 may protect the brain from edema after brain injury. Thus, the peptides and compounds of the present invention may be used alone or in combination with other NMDA receptor antagonists in compositions and methods for the treatment of brain injury and associated secondary cerebral impairments in humans and animals.

The present methods and compounds are useful in preventing, treating, or ameliorating neurological signs and symptoms associated with acute CNS injury. As used herein, acute CNS injury includes but is not limited to stroke (caused by thrombosis, embolism or vasoconstriction), closed head injury, global cerebral ischemia (e.g., ischemia due to systemic hypotension of any cause, including cardiac infarction, cardiac arrhythmia, hemorrhagic shock, and post coronary artery bypass graft brain injury), focal ischemia and intracranial hemorrhage. Ischemic damage to the central nervous system may result from either global or focal ischemic conditions. Global ischemia occurs where blood flow to the entire brain ceases for a period of time, such as during cardiac arrest. Focal ischemia occurs when a portion of the brain is deprived of normal blood flow, such as during thromboembolytic occlusion of a cerebral vessel, traumatic head injury, edema and brain tumors. Much of the CNS damage due to cerebral ischemia occurs during the hours or even days following the ischemic condition, and is secondary to the release of cytotoxic products by damaged tissue.

The present methods and compounds are also useful in preventing, treating, or ameliorating neurological signs and symptoms associated with chronic neurological disease, including but not limited to Alzheimer's disease (AD) and HIV-associated encephalopathy. The finding by the present inventors that ApoE peptides may be used to suppress glial activation provides a role for the peptides and compounds of the invention in the treatment of any neurological disease involving microglial activation. For example, microglia express markers of activation in AD, suggesting that crucial inflammatory events in AD involve microglia. Such activated microglia cluster near amyloid plaques (Griffin et al., 1995). Microglia are also activated in epilepsy (Sheng et al., 1994).

The surprising finding by the present inventors that one way in which ApoE peptides inhibit peptides and other compounds of the invention for treating AD, since it has been recently shown that uptake and pathogenic effects of amyloid beta peptide are blocked by NMDA receptor antagonists (Bi et al., 2002). Other studies indicate that anti-inflammatory drugs may delay the onset or progression of the disease (Breitner et al., 1995; Rogers et al., 1993). Thus, the peptides and compounds of the present invention may be used alone or in combination with other NMDA receptor antagonists or other known pharmaceuticals and especially anti-inflammatory drugs used for the treatment of AD in compositions and methods for the treatment of AD in humans.

The present methods and compounds are also useful in preventing, treating, or ameliorating the neurological signs and symptoms associated with inflammatory conditions affecting the nervous system including the CNS, including but not limited to multiple sclerosis, vasculitis, acute disseminated encephalomyelitis, and Guillain-Barre syndrome. In this regard, the ApoE peptides and other compounds of the invention may be used alone or in combination with other known anti-inflammatory drugs or cytokines to formulate pharmaceutical compositions for the treatment of CNS inflammatory conditions.

The present methods and compounds are useful in preventing, suppressing or reducing the activation of glia in the CNS that occurs as a part of acute or chronic CNS disease. The effect of the present methods and compounds may be assessed at the cellular or tissue level (e.g., histologically or morphometrically), or by assessing a subject's neurological status. The suppression or reduction of glial activation can be assessed by various methods as would be apparent to those in the art; one such method is to measure the production or presence of compounds that are known to be produced by activated glia, and compare such measurements to levels of the same compounds in control situations. Alternatively, the effects of the present methods and compounds in suppressing, reducing or preventing microglial activation may be assessed by comparing the signs and/or symptoms of CNS disease in treated and control subjects, where such signs and/or symptoms are associated with or secondary to activation of microglia.

The present invention is also based on the surprising finding by the inventors that ApoE receptor binding peptides protect against LPS-induced production of cytokines in the periphery in an in vivo animal model of sepsis. Although intact ApoE has recently been shown to protect mice from bacterial LPS-induced lethality (Van Oosten et al., 2001), it is surprising that a peptide containing only the receptor binding region of ApoE confers protection given that ApoE is thought to mediate protection by redirecting LPS from macrophages to parenchymal liver cells. Other possible therapies for sepsis involve the administration of anti-inflammatory beta, granulocyte colony-stimulating factor, IFN-phi, macrophage migration inhibitory factor and high mobility group 1 protein (Zanotti et al., 2002), and monoclonal antibodies, including antiendotoxin antibodies, anti-tumor necrosis factor antibodies, and anti-CD14 antibodies (Matsubara et al., 2002). Thus, the peptides and compounds of the present invention may be used alone or in combination with other known anti-inflammatory cytokines and antibodies in compositions and methods for the treatment of sepsis.

As used herein, the terms "combating," "treating" and "ameliorating" are not necessarily meant to indicate a reversal or cessation of the disease process underlying the CNS or sepsis condition afflicting the subject being treated. Such terms indicate that the deleterious signs and/or symptoms associated with the condition being treated are lessened or reduced, or the rate of progression is reduced, compared to that which would occur in the absence of treatment. A change in a disease sign or symptom may be assessed at the level of the subject (e.g., the function or condition of the subject is assessed), or at a tissue or cellular level (e.g., the production of markers of glial or macrophage activation is lessened or reduced). Where the methods of the present invention are used to treat chronic CNS conditions (such as Alzheimer's disease), the methods may slow or delay the onset of symptoms such as dementia, while not necessarily affecting or reversing the underlying disease process.

Suitable subjects for carrying out the methods of the present invention include male and female mammalian subjects, including humans, non-human primates, and non-primate mammals. Subjects include veterinary (companion animal) subjects, as well as livestock and exotic species.

Active compounds that may be used in the methods of the present invention include ligands or agonists that specifically and/or selectively bind to the LRP/α2M receptor or to any receptor bound by the ApoE peptides of the invention. Examples of such compounds include, but are not limited to, 1) alpha 2 macroglobulin; 2) pseudomonas exotoxin; 3) lipoprotein lipase; 4) apolipoprotein E; 5) oxidized and/or acetylated LDL; 6) receptor associated protein (RAP); 7) remnant particles; 8) low density lipoprotein (LDL); 9) high density lipoprotein (HDL); 10) lactoferrin; 11) tissue plasminogen activator (tPA); 12) urine plasminogen activator (uPA); etc., and receptor binding fragments thereof.

As used herein, an "ApoE peptide" or a "peptide of ApoE" refers to any peptide of ApoE or functional variant thereof that binds to a receptor bound by ApoE and mediates the functional effects described herein. Amino acid residues 100-200 of each isoform of the ApoE molecule comprise a known ApoE receptor binding region. More specifically, the receptor binding region of ApoE is within amino acid residues 130-160 of each isoform of the ApoE molecule (SEQ ID NO:4 and SEQ ID NO:5), and more specifically is within amino acid residues 140-155 (HLRKLR KRLLRDADDL) (SEQ ID NO:1). See, e.g., Weisgraber, Apolipoprotein E: Structure-Function Relationships, *Advances in Protein Chemistry* 45:249 (1994). The amino acid interchanges that define the E2, E3 and E4 isoforms are not found within the region of amino acid residues 140-155, but do influence the overall structure of the Apolipoprotein molecule. ApoE2 and ApoE3 molecules form covalently bound homodimers; ApoE4 molecules do not.

As used herein, the term homodimer refers to a molecule composed of two molecules of the same chemical composition; the term heterodimer refers to a molecule composed of two molecules of differing chemical composition.

The present inventors utilized a 9-mer monomer having an amino acid sequence LRKLRKRLL (SEQ ID NO:2). This 9 amino acid sequence is found within the larger ApoE receptor binding sequence region identified above, and is found at amino acid positions 141-149 of ApoE. The present inventors constructed a dimer of SEQ ID NO:2, i.e., a peptide having an amino acid sequence of LRKLRKRLL LRKLRKRLL (SEQ ID NO:3). Peptides of SEQ ID NO:3 suppressed microglial activation in a dose-dependent fashion. Use of the monomer (monomer peptides of SEQ ID NO:2) did not suppress microglial activation. (See FIG. 2).

The present inventors further utilized a 20-mer monomer having an amino acid sequence TEELRVRLAS HLRKLRKRLL (SEQ ID NO:6). This 20 amino acid sequence is found at amino acid positions 130-149 of ApoE, and comprises the 9-mer SEQ ID NO:2. Peptides of SEQ ID NO:6 suppressed microglial activation in a dose-dependent fashion (see FIGS. 4-7).

The present inventors further showed that a 17-mer having the amino acid sequence LRVRLAS HLRKLRKRLL (SEQ ID NO:10) from amino acid positions 133-149 of ApoE was protective in a murine head injury model and in a murine model of LPS-induced sepsis. The same peptide was also shown to inhibit NMDA excitotoxicity in primary rat neuronal/glial cell cultures.

In contrast, Clay et al., *Biochemistry* 34:11142 (1995) reported that dimeric peptides of amino acids 141-155 or 141-149 were both cytostatic and cytotoxic to T lymphocytes in culture. Cardin et al. *Biochem Biophys Res. Commun.* 154:741 (1988) reported that a peptide of apoE 141-155 inhibited the proliferation of lymphocytes. A peptide consisting of a tandem repeat of amino acids 141-155, as well as longer monomeric peptides comprising the 141-155 region, was found to cause extensive and specific degeneration of neurites from embryonic chicks in vitro. Crutcher et al., *Exp. Neurol.* 130:120 (1994). These authors suggested that peptide sequences associated with apoE might contribute directly to neurodegenerative processes, thereby supporting the unexpected nature of the neuroprotective effect achieved with the peptides of the present invention.

Peptides of the present invention may be produced by standard techniques as are known in the art. Peptides useful in the present methods include those comprising the ApoE LDL receptor binding sequence (including multiple repeats thereof, including but not limited to dimers and trimers); and conjugates of two or more peptides, each of which comprises a peptide as described herein or a peptide comprising the LDL receptor binding sequence. One ApoE receptor binding sequence is provided in SEQ ID NO:1. A preferred peptide comprises or consists of multiple repeats of SEQ ID NO: 2, preferably dimers thereof. Thus, a preferred peptide useful in the present methods is SEQ ID NO:3 (a tandem repeat of LRKLRKRLL), or peptides comprising SEQ ID NO:3. Further preferred peptides comprise or consist of SEQ ID NO:4, SEQ ID NO:5, SEQ ID NO:6 or SEQ ID NO:10.

Modification of the peptides disclosed herein to enhance the functional activities associated with these peptides could be readily accomplished by those of skill in the art. For instance, the ability of a linear tandem repeat of amino acids 141-155 (the 141-155 dimer) to bind the LDL receptor was studied by Dyer et al., *J. Lipid Research* 36:80 (1995). A series of modified peptides was constructed and assessed for LDL binding ability. These authors report that deletion of the charged amino terminal residues (including arg142 and lys143) in 145-155 or 144-150 dimers abolished the LDL receptor activities of the peptides. These authors conclude that LDL-receptor binding activity of the 141-155 dimer is dependent on at least two clusters of basic amino acids present on the hydrophilic face of the amphipathic alpha-helix of the 141-155, 141-150, 141-155 (lys143→ala) and 141-155 (arg150→gala) dimer peptides. Dyer et al., *J. Biol. Chem.* 266:15009 (1991) reported that a self-conjugate of peptide 141-155, and a peptide consisting of a tandem repeat of 141-155, were able to inhibit both lymphocyte proliferation and ovarian androgen production. Dyer et al., *J. Biol. Chem.* 266:22803 (1991) investigated the LDL binding ability of a dimeric 141-155 tandem peptide, and a trimeric 141-155 peptide. Binding was decreased with amino acid substitutions of Lys-143-→Ala, Leu144-→Pro, and Arg150-→Ala. Lalazar et al., *J. Biol. Chem.* 263:3542 (1988) investigated variants of ApoE for binding to the LDL receptor. When neutral amino acids were substituted for basic residues at positions 136, 140, 143, and 150, binding activity was reduced. Where proline was substituted for leucine144 or alanine152, binding was reduced. However, slightly enhanced receptor binding was displayed by a variant in which arginine was substituted for serine139 and alanine was substituted for leucine 149.

Active compounds (or "active agents") useful in the methods of the present invention include those that compete with a peptide of SEQ ID NO:3, and/or a peptide of SEQ ID NO:6, and/or a peptide of SEQ ID NO:10 in binding to microglial receptors or receptors on neighboring effector cells, such as astrocytes, to thereby prevent or suppress activation of the microglia by molecules that would otherwise activate microglia. Compounds that are useful in the present methods also include those which act as antagonists for the receptor bound by peptides of SEQ ID NO:3 and/or SEQ ID NO:6 and/or SEQ ID NO:10. Antibodies that selectively target and bind to this receptor can also be used as antagonists of microglial activation according to the present invention. Such antibodies selectively or specifically bind to the receptor bound by peptides of SEQ ID NO:3 and/or peptides of SEQ ID NO:6 and/or peptides of SEQ ID NO:10.

Peptides of SEQ ID NO:3, SEQ ID NO:6, SEQ ID NO:10 or conformational analogues thereof, are an aspect of the present invention. Such compounds are peptides or peptidomimetics having a core sequence of amino acids with a conformation in aqueous solution that interacts with receptor molecules on glial cells to block the activation of glial cells that would otherwise occur in conjunction with acute or chronic CNS injury, or exposure to known activators of microglia such as LPS. Stated another way, such compounds are characterized by the ability to compete with peptides of SEQ ID NO:3 and/or peptides of SEQ ID NO:6 and/or SEQ ID NO:10 for binding to microglia, and by their ability to suppress microglial activation by known activators such as LPS.

Another variation of the therapeutic peptides of the present invention is the linking of from one to five amino acids or analogues to the N-terminal or C-terminal amino acid of the therapeutic peptide. Analogs of the peptides of the present invention may also be prepared by adding from one to five additional amino acids to the N-terminal, C-terminal, or both N- and C-terminals, of an active peptide, where such amino acid additions do not adversely affect the ability of the peptide to bind to microglia at the site bound by a peptide of SEQ ID NO:3 and/or SEQ ID NO:6 and/or SEQ ID NO:10.

Changes in the amino acid sequence of peptides can be guided by known similarities among amino acids and other molecules or substituents in physical features such as charge density, hydrophobicity, hydrophilicity, size and configuration, etc. For example, the amino acid Thr may be replaced by Ser and vice versa, and Leu may be replaced by Ile and vice versa. Further, the selection of analogs may be made by mass screening techniques known to those skilled in the art (e.g., screening for compounds which bind to microglia at the receptor bound by a peptide of SEQ ID NO:3 and/or SEQ ID NO:6 and/or SEQ ID NO:10). A preferred exchange is to replace Ser with Arg, to increase the arginine content of the peptide; examples include peptides of or comprising SEQ ID NO:7, SEQ ID NO:8 or SEQ ID NO:9. A further preferred exchange is to substitute alanine for leucine149.

Peptides of the present invention may also be characterized as short peptides of from about 20 amino acids, 22 amino acids, 24 amino acids, 26 amino acids, 28 amino acids, 30 amino acids, 35 amino acids, or 40 amino acids, up to about 22 amino acids, 24 amino acids, 26 amino acids, 28 amino acids, 30 amino acids, 35 amino acids, 40 amino acids, 45 amino acids, 50 amino acids or more, where the peptides comprise the 18-amino acid sequence LRKLRKRLL LRKLRKRLL (SEQ ID NO:3), or variants thereof that retain the receptor binding ability of peptides of SEQ ID NO:3. A preferred peptide useful in the present invention is one consisting of or comprising SEQ ID NO:3. Where longer peptides are employed, those incorporating amino acid sequences derived from the ApoE sequence immediately surrounding amino acid residues 141-149 are preferred. Where peptides longer than 18 amino acids are employed, it is contemplated that they may include virtually any other amino acid sequences so long as the resultant peptide maintains its ability to bind to microglial and suppress microglia activation in acute and chronic CNS inflammation. The present invention includes those variations of the ApoE sequence at 141-149 which are known to retain the ability LDL receptor-binding ability. Synthetic peptides may further be employed, for example, using one or more D-amino acids in place of L-amino acids, or by adding groups to the N- or C-termini, such as by acylation or amination.

Peptides of the present invention may also be characterized as short peptides of from about 10 amino acids, 12 amino acids, 14 amino acids, 15 amino acids, 18 amino acids, 20 amino acids, 22 amino acids, 24 amino acids, 26 amino acids, 28 amino acids, 30 amino acids, 35 amino acids, or 40 amino acids, up to about 15 amino acids, 22 amino acids, 24 amino acids, 26 amino acids, 28 amino acids, 30 amino acids, 35 amino acids, 40 amino acids, 45 amino acids, 50 amino acids or more, where the peptides comprise the 9-amino acid sequence LRKLRKRLL (SEQ ID NO:2), or variants thereof that retain the receptor binding ability of peptides of SEQ ID NO:3 and/or SEQ ID NO:6 and/or SEQ ID NO:10. A preferred peptide useful in the present invention is one consisting of or comprising the apoE receptor binding region; a particularly preferred peptide consists of or comprises SEQ ID NO:6 and/or SEQ ID NO:10. Where longer peptides are employed, those incorporating amino acid sequences derived from within the apoE receptor binding region, or the ApoE sequence immediately surrounding the apoE receptor binding region, are preferred, although it is contemplated that these peptides may include virtually any other amino acid sequences so long as the resultant peptide maintains its ability to bind to microglia and suppress microglia activation in acute and chronic CNS inflammation. The present invention includes those variations of the ApoE sequence at 141-149 which are known to retain the ability LDL receptor-binding ability. Synthetic peptides may further be employed, for example, using one or more D-amino acids in place of L-amino acids, or by adding groups to the N- or C-termini, such as by acylation or amination.

The peptides of the present invention include not only natural amino acid sequences, but also peptides which are analogs, chemical derivatives, or salts thereof. The term "analog" or "conservative variation" refers to any polypeptide having a substantially identical amino acid sequence to the therapeutic peptides identified herein, and in which one or more amino acids have been substituted with chemically similar amino acids. For example, a polar amino acid such as glycine or serine may be substituted for another polar amino acid; a basic amino acid may be substituted for another basic amino acid, or an acidic amino acid may be substituted for another acidic amino acid; or a non-polar amino acid may be substituted for another non-polar amino acid. There term "analog" or "conservative variation" as used herein also refers to a peptide which has had one or more amino acids deleted or added to a polypeptide of the present invention, but which retains a substantial sequence similarity (at least about 85% sequence similarity, and preferably at least 90%, 92%, 94%, 95%, 96%, 98% or even 99% sequence similarity), where the peptide retains the ability to suppress microglial activation as described herein.

The amino acids constituting peptides of the present invention may be of either the L-configuration or the D-configuration. Therapeutic peptides of the present invention may be in free form or the form of a salt, where the salt is pharmaceutically acceptable.

As used herein, the term "administering to the brain of a subject" refers to the use of routes of administration, as are known in the art, that provide the compound to the central nervous system tissues, and in particular the brain, of a subject being treated.

Preferably, the compounds of the present invention are used in combination with a pharmaceutically acceptable carrier. The present invention thus also provides pharmaceutical compositions suitable for administration to mammalian subjects. Such compositions comprise an effective amount of the compound of the present invention in combination with a pharmaceutically acceptable carrier. The carrier may be a liquid, so that the composition is adapted for parenteral administration, or may be solid, i.e., a tablet or pill formulated for oral administration. Further, the carrier may be in the form of a nebulizable liquid or solid so that the composition is adapted for inhalation. When administered parenterally, the composition should by pyrogen free and in an acceptable parenteral carrier. Active compounds may alternatively be formulated encapsulated in liposomes, using known methods. Additionally, the intranasal administration of peptides to treat CNS conditions is known in the art (see, e.g., U.S. Pat. No. 5,567,682 to Pert, regarding intranasal administration of peptide T to treat AD). (All patents referenced herein are intended to be incorporated by reference herein in their entirety.) Preparation of a Compound of the Present Invention for Intranasal Administration May be Carried out using techniques as are known in the art.

Pharmaceutical preparations of the compounds of the present invention may optionally include a pharmaceutically acceptable diluent or excipient. For the sepsis-related embodiments of the invention, the disclosed peptides may be conjugated to pharmaceutically acceptable carriers to increase serum half-life using methods that are known to those of skill in the art. See, e.g., U.S. Pat. No. 6,423,685, which is herein incorporated by reference in its entirety.

An effective amount of the compound of the present invention is that amount that decreases microglial activation compared to that which would occur in the absence of the compound; in other words, an amount that decreases the production of neurotoxic compounds by the microglia, compared to that which would occur in the absence of the compound. The effective amount (and the manner of administration) will be determined on an individual basis and will be based on the specific therapeutic molecule being used and a consideration of the subject (size, age, general health), the condition being treated (AD, acute head injury, cerebral inflammation, etc.), the severity of the symptoms to be treated, the result sought, the specific carrier or pharmaceutical formulation being used, the route of administration, and other factors as would be apparent to those skilled in the art. The effective amount can be determined by one of ordinary skill in the art using techniques as are known in the art. Therapeutically effective amounts of the compounds described herein may be determined using in vitro tests, animal models or other dose-response studies, as are known in the art.

The compounds of the present invention may be administered acutely (i.e., during the onset or shortly after events leading to cerebral inflammation or ischemia), or may be administered prophylactically (e.g., before scheduled surgery, or before the appearance of neurologic signs or symptoms), or administered during the course of a degenerative disease to reduce or ameliorate the progression of symptoms that would otherwise occur. The timing and interval of administration is varied according to the subject's symptoms, and may be administered at an interval of several hours to several days, over a time course of hours, days, weeks or longer, as would be determined by one skilled in the art.

The typical daily regime may be from about 0.01 µg/kg body weight per day, from about 10 µg/kg body weight per day, from about 100 µg/kg body weight per day, from about 1000 µg/kg body weight per day, from about 10,000 µg/kg body weight per day, from about 100,000 µg/kg body weight per day.

The blood-brain barrier presents a barrier to the passive diffusion of substances from the bloodstream into various regions of the CNS. However, active transport of certain agents is known to occur in either direction across the blood-brain barrier. Substances that may have limited access to the brain from the bloodstream can be injected directly into the cerebrospinal fluid. Cerebral ischemia and inflammation are also known to modify the blood-brain barrier and result in increased access to substances in the bloodstream.

Administration of a compound directly to the brain is known in the art. Intrathecal injection administers agents directly to the brain ventricles and the spinal fluid. Surgically-implantable infusion pumps are available to provide sustained administration of agents directly into the spinal fluid. Lumbar puncture with injection of a pharmaceutical compound into the cerebrospinal fluid ("spinal injection") is known in the art, and is suited for administration of the present compounds.

Pharmacologic-based procedures are also known in the art for circumventing the blood brain barrier, including the conversion of hydrophilic compounds into lipid-soluble drugs. The active agent may be encapsulated in a lipid vesicle or liposome.

The intra-arterial infusion of hypertonic substances to transiently open the blood-brain barrier and allow passage of hydrophilic drugs into the brain is also known in the art. U.S. Pat. No. 5,686,416 to Kozarich et al. discloses the co-administration of receptor mediated permeabilizer (RMP) peptides with compounds to be delivered to the interstitial fluid compartment of the brain, to cause an increase in the permeability of the blood-brain barrier and effect increased delivery of the compounds to the brain. Intravenous or intraperitoneal administration may also be used to administer the compounds of the present invention.

One method of transporting an active agent across the blood-brain barrier is to couple or conjugate the active agent to a second molecule (a "carrier"), which is a peptide or non-proteinaceous moiety selected for its ability to penetrate the blood-brain barrier and transport the active agent across the blood-brain barrier. Examples of suitable carriers include pyridinium, fatty acids, inositol, cholesterol, and glucose derivatives. The carrier may be a compound which enters the brain through a specific transport system in brain endothelial cells. Chimeric peptides adapted for delivering neuropharmaceutical agents into the brain by receptor-mediated transcytosis through the blood-brain barrier are disclosed in U.S. Pat. No. 4,902,505 to Pardridge et al. These chimeric peptides comprise a pharmaceutical agent conjugated with a transportable peptide capable of crossing the blood-brain barrier by transcytosis. Specific transportable peptides disclosed by Pardridge et al. include histone, insulin, transferrin, and others. Conjugates of a compound with a carrier molecule, to cross the blood-brain barrier, are also disclosed in U.S. Pat. No. 5,604,198 to Poduslo et al. Specific carrier molecules disclosed include hemoglobin, lysozyme, cytochrome c, ceruloplasmin, calmodulin, ubiquitin and substance P. See also U.S. Pat. No. 5,017,566 to Bodor.

An alternative method of administering peptides of the present invention is carried out by administering to the subject a vector carrying a nucleic acid sequence encoding the peptide, where the vector is capable of entering brain cells so that the peptide is expressed and secreted, and is thus available to microglial cells. Suitable vectors are typically viral vectors, including DNA viruses, RNA viruses, and retroviruses. Techniques for utilizing vector deliver systems and carrying out gene therapy are known in the art. Herpesvirus vectors are a particular type of vector that may be employed in administering compounds of the present invention.

Screening Methods. Also disclosed herein are methods of screening compounds for the ability to prevent or reduce microglial activation under conditions of cerebral ischemia or cerebral inflammation. Such methods comprise contacting an activated microglial cell with a test compound, and detecting whether the test compound binds to microglia at the same receptor at which peptides of SEQ ID NO:3 and/or SEQ ID NO:6 and/or SEQ ID NO:10 bind. The contacting step may be carried out in vitro, for example in cell culture. A competitive binding assay may be used to detect whether the test compound binds to the same receptor that is bound by peptides of SEQ ID NO:3 and/or SEQ ID NO:6 and/or SEQ ID NO:10, for instance by detecting the inhibition of receptor binding of a peptide of the invention that is conjugated to or associated with a detectable label such a radioisotope or a fluorescent molecule, or any other detectable label that is known and commonly used in the art.

An additional method of screening a test compound for the ability to suppress microglial activation comprises incubating an activated microglial cell culture with a test compound, and measuring at least one marker of microglial activation. A decrease in a marker of microglial activation (compared to the level of that marker that would occur in the absence of the test compound) indicates that the test compound is able to suppress, prevent or reduce microglial activation. An exemplary marker of microglial activation is the production of nitric oxide.

A further method of screening a test compound for the ability to suppress microglial activation involves pre-incubating a microglial cell culture with a test compound, then incubating the microglial cell culture with a compound that is known to activate microglia. At least one marker of microglial activation is then measured, and a decrease in the activation marker (compared to that which occurs in the absence of the pre-incubation step) indicates that the test compound is able to affect microglial activation. An exemplary marker of microglial activation is the production of nitric oxide.

Atherosclerosis. It known that the inflammatory process mediates an aspect of the atherosclerotic process. See, e.g., Hansson (1994); Berliner et al. (1995); Watanabe et al. (1997). ApoE is known to be secreted by macrophages locally at blood vessel walls (although the amount secreted by macrophages in an individual is trivial compared to the amount of ApoE produced by the liver). In the classic model of atherosclerosis, ApoE functions to remove cholesterol from the blood stream and deliver it to macrophages or to the liver. However, it has become apparent that ApoE secreted by macrophages at the blood vessel wall decreases atherosclerotic plaque formation, independent of any lipid metabolism effects. For instance, ApoE-deficient mice are accepted as a model of hypercholesteremia and atherosclerotic disease. Providing ApoE-secreting macrophages to such mice dramatically decreases atherosclerotic plaque formation. Linton et al. (1995). Conversely, replacing a wild-type mouse's macrophages with ApoE-deficient macrophages accelerates atherosclerotic changes, even though the animal continues to produce ApoE by the liver. Fazio et al. (1997).

In atherosclerosis it is hypothesized that ApoE, via a receptor-mediated event, down-regulates macrophage activation in the vicinity of blood vessel walls. Such down-regulation of macrophage activation interrupts or interferes with the cascade of events associated with atherosclerotic plaque formation, to thereby reduce or slow the formation of atherosclerotic lesions. The cascade of events known to be associated with atherosclerosis includes smooth muscle cell and endothelial cell proliferation, and foam cell formation. Evidence exists that ApoE downregulates each of these processes. ApoE thus affects the presence and progression of atherosclerosis in vivo, independent of its effects on lipids. The progression of atherosclerosis may be assessed by measuring the amount or size of atherosclerotic plaques, or the percentage of the blood vessel blocked by an atherosclerotic lesion, or the rate of growth of such plaques.

The present inventors have for the first time demonstrated that ApoE transduces a calcium-mediated signal ($Ca^{2+}$/inositol triphosphate signal transduction) in macrophage, indicating that ApoE modifies macrophage function by downregulating macrophage activation and, therefore, subsequent inflammation. Peptides, compounds, methods and pharmaceutical formulations as described herein in relation to microglia and CNS disease are accordingly useful in methods of suppressing the activation of macrophages to suppress, prevent, or slow atherosclerosis.

Atherosclerosis refers to the thickening of the arterial intima and accumulation of lipid in artherosclerotic plaques. Administration of compounds of the present invention to treat or prevent atherosclerosis may be by any means discussed herein as well as other suitable methods that are known in the art. When using the present compounds to prevent, slow or treat atherosclerotic changes, it is apparent that they need not be formulated to pass through the blood brain barrier. Conditions that may be treated by the present method include atherosclerosis of the coronary arteries; arteries supplying the Central Nervous system, such as carotid arteries; arteries of the peripheral circulation or the splanchnic circulation; and renal artery disease. Administration, such as parenteral administration, may be site-specific or into the general blood stream.

The examples which follow are set forth to illustrate the present invention, and are not to be construed as limiting thereof.

EXAMPLE 1

Microglial Nitric Oxide Production

Materials and Methods

This study examined the role of endogenous apoE in modulating microglial nitric oxide (NO) production, as measured by nitrite accumulation following lipopolysaccharide (LPS) stimulation of microglia.

Culture preparation and characterization: Mixed glial cell cultures were prepared from: (a) wildtype (C57B16; Jackson Laboratories) mouse pups; (b) ApoE deficient mutant mouse pups (ApoE-deficient mice), and (c) transgenic mouse pups expressing human ApoE3 and not murine ApoE (ApoE3 mice). See Xu et al., *Neurobiol. Dis.* 3:229 (1996) regarding the creation and characterization of the transgenic mice. Mixed glial cell cultures were prepared as has been described. See McMillian et al., *Neurochem.* 58:1308 (1992); Laskowitz et al., *J. Neuroimmunol.* 76:70 (1997). Briefly, brains were removed from 2-4 day old pups, cleaned of membranes and blood vessels, mechanically dispersed in $Ca^{+2}$-free media, and collected by centrifugation. Cells were then plated in DMEM/F12 (containing 10% fetal calf serum, 1% penicillin/ streptomycin, Gibco #15070), one brain per 25 cm flask. Mixed neuronal/glial preparations were grown in humidified incubators until confluent (3-5 weeks).

The percentage of microglia, astrocytes and neurons were quantified to demonstrate that cultures prepared from ApoE-deficient and ApoE3 mice had comparable glial populations. Immunostaining was performed using antibodies to glial fibrillary acidic protein (GFAP; SIGMA®; 1:500 dilution) and tau protein (SIGMA®; 1:500 dilution) to estimate numbers of astrocytes and neurons, and peroxidase-coupled Bandeiraea simplifolica B4 isolectin and naphthyl acetate esterase staining was used to detect microglia. Laskowitz et al., *J. Neuroimmunol.* 76:70 (1997). A mixed neuronal-glial culture system was used, as this most closely approximates the normal CNS milieu, and allows glia-glia interactions, which play a role in the inflammatory cascade.

Comparable glial populations were confirmed using semi-quantitative Western blot analysis performed for astrocytes (aGFAP; SIGMA®), neurons (atau; SIGMA®) and microglia (Bandeiraea simplifolica B4 isolectin; SIGMA®). Cellular protein was harvested at the end of experiments and 50 μg protein from each sample was separated by polyacrylamide gel electrophoresis and the protein was transferred to nylon membranes. Non-specific binding of antisera and lectin was blocked by preincubation of the membrane in 4% dried milk, 0.1% Triton X-100. Membranes were incubated overnight with antibodies or 1 μg/ml B4 isolectin. After extensive washing in phosphate-buffered saline, bound antibody or lectin was visualized by an ABC kit (Vector, Burlingame, Calif.), using diaminobenzidine as substrate.

Culture Stimulation Cultures were plated in serum-free media after washing cells once with this media, and stimulated with LPS 100 ng/ml (SIGMA®). Aliquots were taken at 24 and 60 hours for nitrite assay.

Nitrite Quantification The production of NO was assessed by measuring the accumulation of nitrite, which was quantified using a calorimetric reaction with Griess reagent (0.1% N-1-naphthylethylenediamine dihydrochloride, 1% sulfanilamide, and 2.5% $H_3PO_4$). Absorbance was measured at 570 nm by spectrophotometry. The sensitivity of this assay is approximately 0.5 μM.

Statistical Analysis Data were compared by ANOVA and the Fischer LSD multiple range test; $p<0.05$ was considered significant.

EXAMPLE 2

Microglial Nitric Oxide Production

Results

Culture Characterization: No significant differences were found in glial populations among the cultures prepared from ApoE-deficient, ApoE3, and wild-type mice. Cultures comprised approximately 70% astrocytes, 15% microglia and 15% neurons. Comparisons of cellular preparations from wildtype mice, ApoE-deficient mice and ApoE3 mice showed no differences in glial populations. In particular, levels of microglia (the primary effector cells for NO production) were comparable in all three culture preparations, as detected by lectin binding (data not shown).

ApoE-deficient mouse cultures showed robust nitrite responses during the first 24 hours of exposure to LPS. This enhanced response was 6-fold greater than that observed with microglia from control animals ($p=0.0001$; FIG. 1). Cultures from transgenic mice in which murine apoE is replaced with human ApoE3 show weak responses to LPS that were not significantly different than responses of wildtype animals ($p=0.64$ and $p=0.2$ at 24 and 60 hours, respectively). By 60 hours, increased nitrite accumulation was observed in response to LPS in wildtype and ApoE3 transgenic mouse preparations, although there was still a significantly greater amount of nitrite in the apoE deficient culture as compared to controls ($p=0.04\%$; FIG. 1)

The above studies show that ApoE deficient mixed neuronal-glial cultures respond differently to LPS stimulation than glial cultures prepared from mice expressing native murine ApoE3 or those expressing the human ApoE3 isoform. These results are consistent with ApoE being a biologically relevant mediator of the CNS response to injury. These studies demonstrate that endogenous ApoE modulates glial secretion of LPS-stimulated nitric oxide production, and suggest that one function of endogenous ApoE produced within the brain is to suppress microglial reactivity and thus alter the CNS response to acute and chronic injury.

EXAMPLE 3

Suppression of Microglial Activation by Peptides of SEQ ID NO:3

Enriched microglia primary cultures were prepared from the brains of apoE deficient mouse pups as described in Example 1, above. The microglia were stimulated with lipopolysaccharide (100 ng/ml) to activate the microglia as described in Example 1. Activated microglia secrete inflammatory cytokines and nitric oxide; the secretion of nitric oxide was used in the present experiment as a marker of microglial activation. Nitric oxide production was assessed as described in Example 1.

Figure 2:
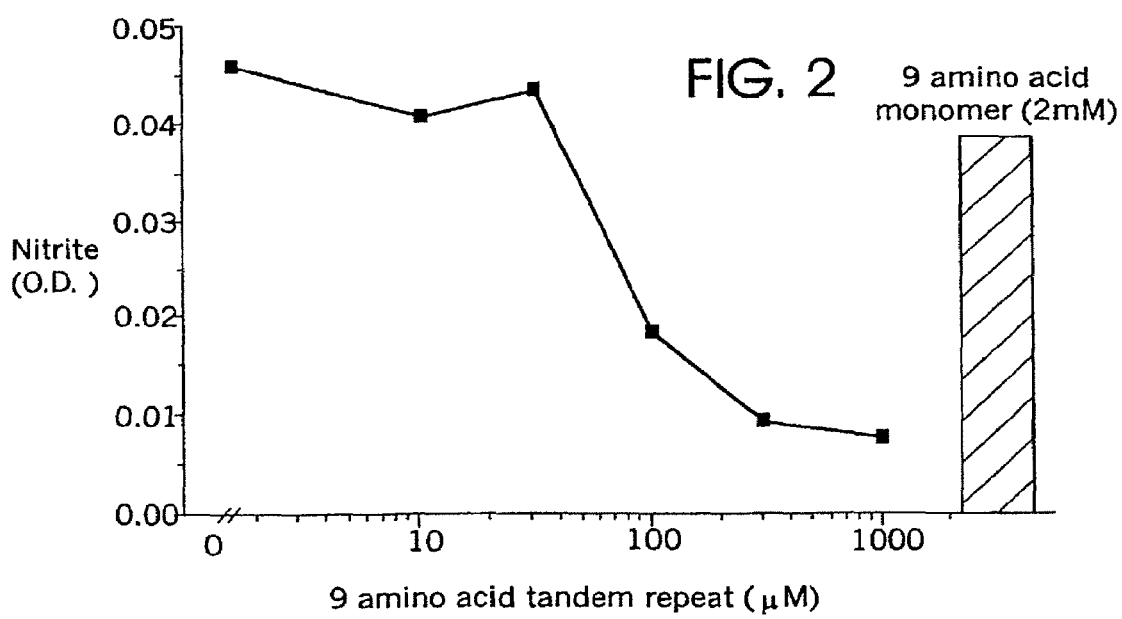
FIG. 2 graphs nitrite production by enriched microglia primary cultures from ApoE-deficient mice after stimulation with LPS and subsequent addition of peptides of SEQ ID NO:3 (tandem repeat peptides). Peptides were added in doses of from 0 μM to 1000 μM, and a dose dependent decrease in nitrite production was observed. As a control, peptides of SEQ ID NO:2 were added to cultures (solid bar); no decrease in nitrite production was observed.

Peptides of SEQ ID NO:3 were added to cultures of activated microglia, in dosages of from 0 µM to 1000 µM. A dose-dependent decrease in nitric oxide secretion was observed after 48 hours (FIG. 2). The administration of a peptide of SEQ ID NO:2 in a dose of 2 mM did not result in any apparent decrease in nitric oxide secretion (FIG. 2). The monomer peptide of SEQ ID NO:2 acted as a control to establish that the observed results are not due to any non-specific peptide effect.

EXAMPLE 4

Effect of ApoE on Macrophage

Intracellular signaling pathways of ApoE were investigated using peritoneal macrophage.

Figure 3A:
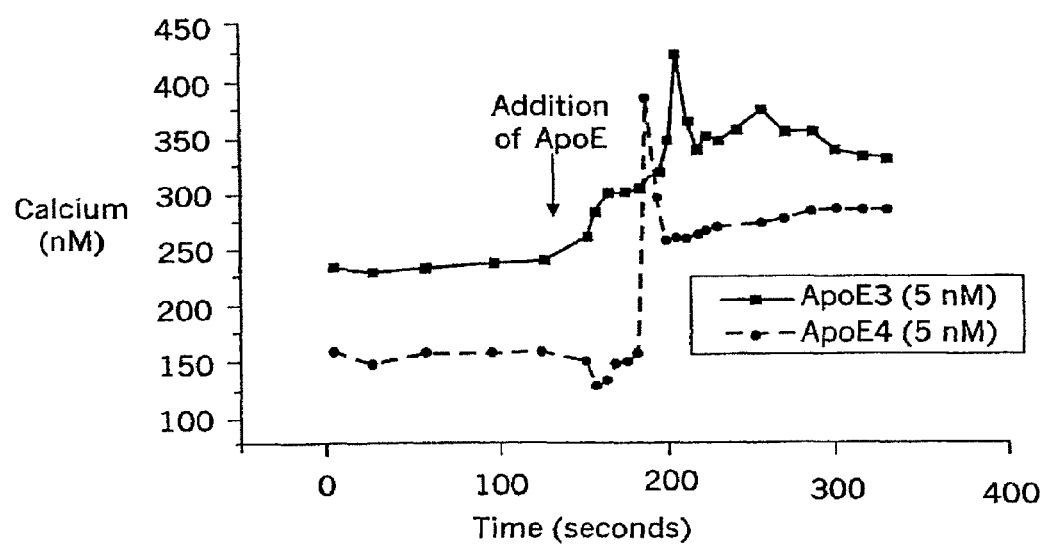
FIG. 3A graphs intracellular calcium content over time in murine peritoneal macrophages, after exposure to either ApoE3 (squares) or ApoE4 (circles).

Thioglycolate-elicited peritoneal macrophage were harvested from 8-week old C57-BL6 mice, and plated at a density of $4 \times 10^3$ cells on glass coverslips, loaded with 2.5 µM Fura-2/AM for thirty minutes, and washed with Hanks buffered solution containing 75 calcium. After exposure to 5 nM human recombinant apoE3 or E4, intracellular calcium was measured by Zeiss digital microscopy. As shown in FIG. 3A, ApoE caused intracellular mobilization of intracellular calcium in the macrophage. Preincubation with 100 molar excess of Receptor Associated Protein (RAP) did not block this effect; RAP is a physiological antagonist to LRP and blocks the function of LRP.

Macrophage were also plated at a density of $2 \times 10^6$ cells/well, labeled with $^3$H-myoinositol (8 µC/ml) 16 hours at 37 degrees, and exposed to human ApoE3 or ApoE4 (5 nM). Control cells were exposed to vehicle but not ApoE. Results are shown in FIG. 3B; values are expressed as the percent change in inositol trisphosphate in treated cells as compared to control cells.

Figure 3B:
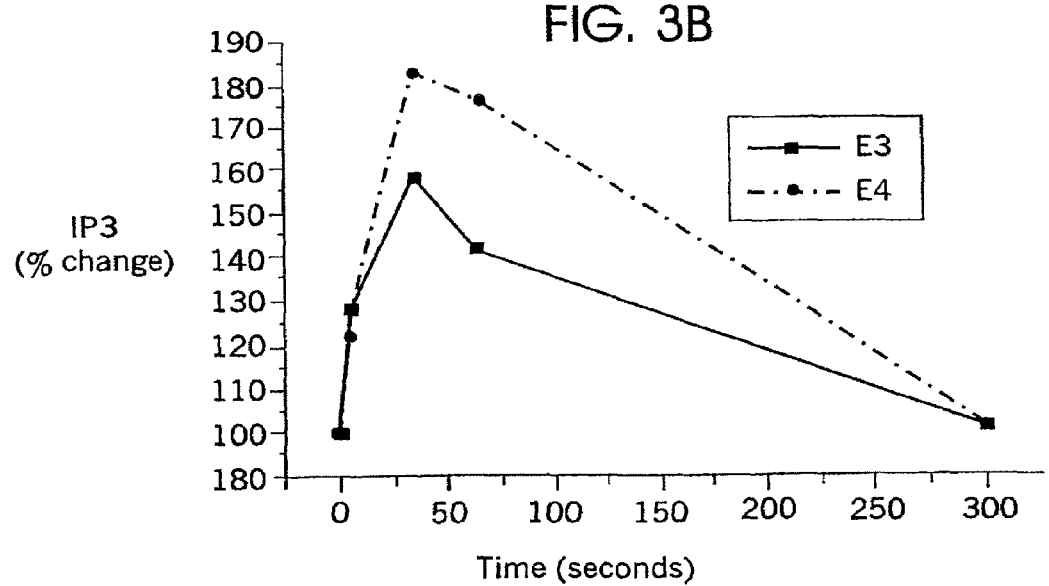
FIG. 3B graphs inositol trisphosphate (IP3) in murine peritoneal macrophages exposed to either ApoE3 (squares) or ApoE4 (circles). The graph shows the percent change in IP3 content in treated cells compared to control cells exposed to vehicle but not ApoE.

Exposure of peritoneal macrophage to ApoE induced a rise in intracellular calcium associated with turnover of inositol tris-phosphate (FIGS. 3A and 3B). The present results indicate that ApoE initiates a signal transduction pathway that affects and modifies macrophage function. The present data suggest that ApoE downregulates macrophage activation and inflammation; macrophage activation and inflammation is known to contribute to the atherosclerotic process.

EXAMPLE 5

Suppression of Microglial Activation Using Peptides of SEQ ID NO:6

A 20-amino acid peptide derived from the receptor binding region of apoE, containing amino acids 130-149 (SEQ ID NO:6) was prepared according to methods known in the art.

Primary murine microglial cultures were prepared as described in Example 1, from apoE deficient mouse pups. In some cultures the microglia were activated with lipopolysaccharide (100 ng/ml), as described in Example 1.

Figure 4:
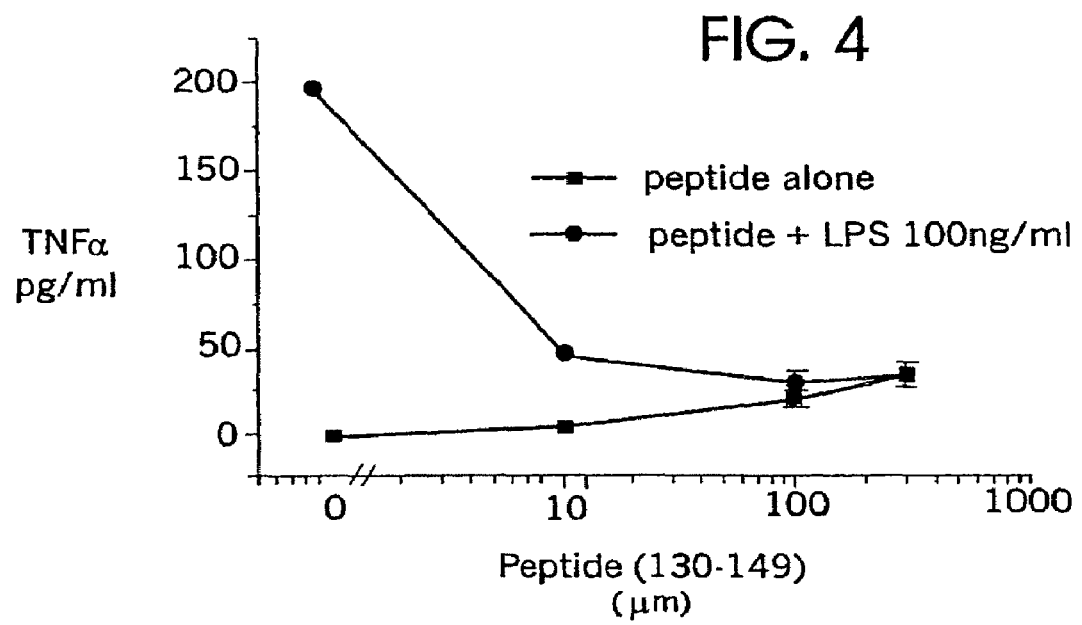
FIG. 4 graphs production of TNFα (picogram/ml) by microglia primary cultures from ApoE-deficient mice after addition of peptides of SEQ ID NO:6 (squares), or addition of peptides of SEQ ID NO:6 and LPS (100 ng/ml) (circles). Peptides were added in doses of 10 μM, 100 μM and 1000 μM.

Peptides of SEQ ID NO:6 were added to cultures of activated and non-activated microglia, in dosages of 0 µM (control), 10 µM, 100 µM and 1000 µM (FIG. 4). Each dosage level of peptide was tested alone (squares) and in combination with LPS (100 ng/ml; circles). The production of TNFα was then measured 24 hours after addition of the peptides. A decrease in TNFα production by activated microglia (compared to control culture) was observed with each peptide dose used (FIG. 4, circles). Data in FIG. 4 is presented in at least triplicate at each dose; error bars represent standard error of the mean).

These results indicate that peptides of SEQ ID NO:6 suppress cytokine release from activated glial cells.

EXAMPLE 6

Cytotoxicity of Peptides of SEQ ID NO:6

The toxic effects of peptides of SEQ ID NO:6 was investigated. Cultures of activated (LPS) and non-activated microglia, as described in Example 5, were used. Peptides having SEQ ID NO:6 were added to cell cultures in amounts of 0 µM (control), 10 µM, 100 µM and 1000 µM; each dosage level of peptide was tested alone (squares) and in combination with LPS (100 ng/ml; circles). Cell viability was then measured by optical density 24 hours after addition of the peptides.

Figure 5:
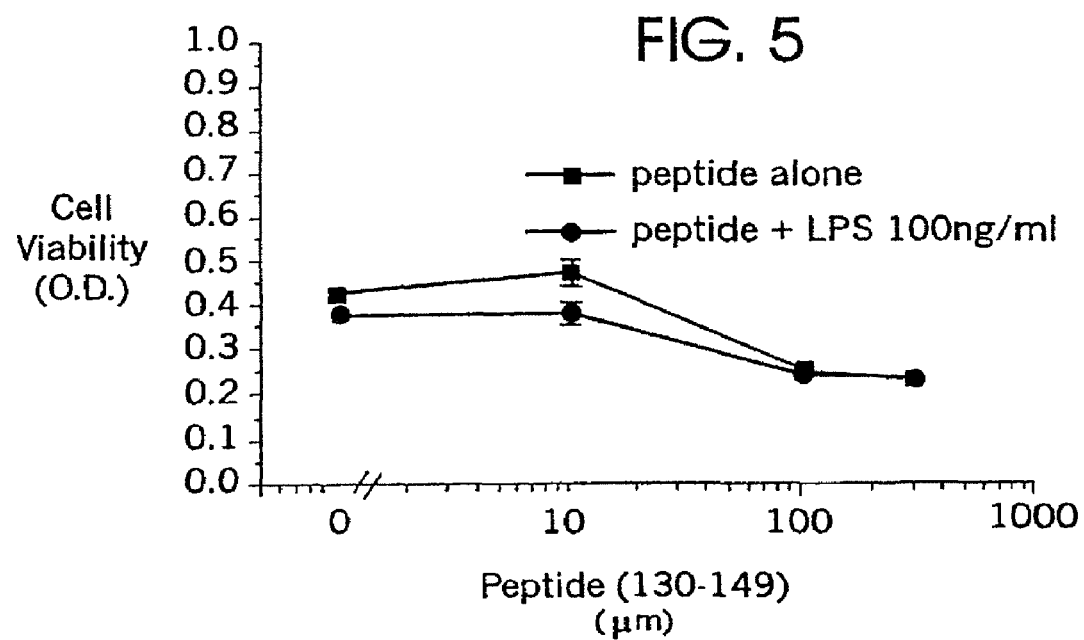
FIG. 5 is a graph of the optical density of cell cultures, as a measure of cell viability. Cultures of microglia from ApoE-deficient mice were exposed to either peptides of SEQ ID NO:6 (squares), or peptides of SEQ ID NO:6 and LPS (100 ng/ml) (circles). Peptides were added in doses of 10 μM, 100 μM and 1000 μM.

As shown in FIG. 5, optical density was approximately the same in cultures receiving 0 µM and 10 µM of peptide, but decreased in cultures receiving 100 µM or 1000 µM. These results, taken with the results of Example 5, indicate that a non-toxic concentration of a peptide of SEQ ID NO:6 is sufficient to suppress glial cytokine release.

EXAMPLE 7

Suppression of Glial Cytokines and Cytotoxicity of Peptides of SEQ ID NO:6

Figure 6:
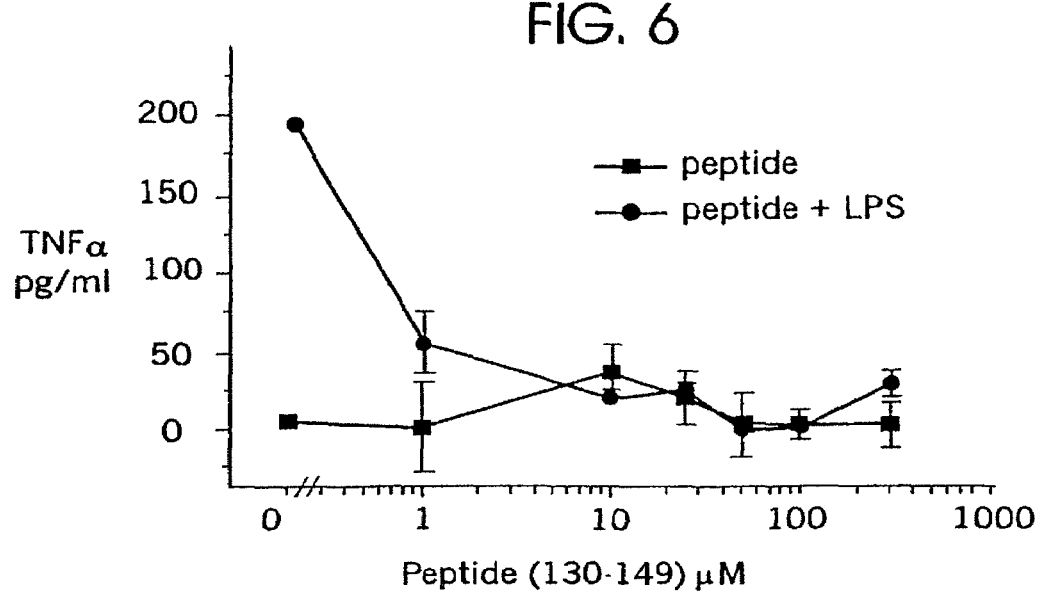
FIG. 6 graphs production of TNFα (picogram/ml) by microglia primary cultures from ApoE-deficient mice after addition of peptides of SEQ ID NO:6 (squares), or addition of peptides of SEQ ID NO:6 and LPS (100 ng/ml) (circles). Peptides were added in doses of 1 μM, 10 μM, 100 μM and 1000 μM.
Figure 7:
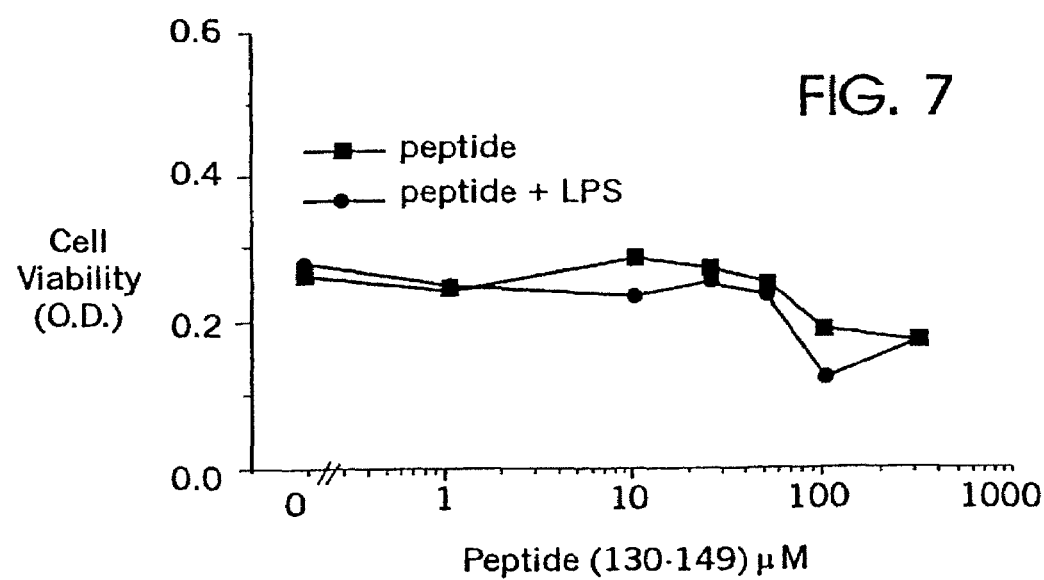
FIG. 7 is a graph of the optical density of cell cultures, as a measure of cell viability. Cultures of microglia from ApoE-deficient mice were exposed to either peptides of SEQ ID NO:6 (squares), or peptides of SEQ ID NO:6 and LPS (100 ng/ml) (circles). Peptides were added in doses of 10 μM, 100 μM and 1000 μM.

The experiments as described in Examples 5 and 6 were repeated using a peptide doses of 0 µM (control), 1 µM, 10 µM, 100 µM and 1000 µM. Each dosage level of peptide was tested alone (squares) and in combination with LPS (100 ng/ml; circles). The production of TNFα was measured 24 hours after administration of the peptides, and results are shown in FIG. 6. The optical density of the cell cultures was also measured (at 24 hours) to assess cell viability; results are shown in FIG. 7.

These results show that microglial cytokine release was suppressed in cell cultures receiving as little as 1 µM of peptide, but cytotoxic effects were seen only in cultures receiving much larger doses of peptide. The results of examples 5-7 indicate that non-toxic concentrations of peptides comprising the receptor binding region of apoE are able to suppress cytokine release from activated microglia.

EXAMPLE 8

In Vivo Treatment of Focal Ischemia

A murine model of focal ischemia-reperfusion is used to assess the effects of intrathecal, intravenous or intraperitoneal administration of small therapeutic peptides (fewer than 30 amino acids in length) comprising the apoE LDL receptor region. One such peptide has SEQ ID NO:6.

Wild-type mice are subjected to middle cerebral artery occlusion and reperfusion according to techniques known in the art (see, e.g., Laskowitz et al., *J. Cereb. Blood Flow Metab.* 17:753 (July 1997)). One group of mice (wild-type control) receives no treatment after cerebral artery occlusion; in a similar group (wild-type treatment group) each mouse receives intrathecal, intraperitoneal or intravenous injection of a therapeutic peptide. Therapeutic peptides may be injected in varying doses, using the in vitro data provided above as an initial guide.

Each animal is evaluated neurologically at a predetermined time after reperfusion (e.g., 24 hours after reperfusion) (see, e.g. Laskowitz et al., *J. Cereb. Blood Flow Metab.* 17:753 (July 1997)). After neurological examination each mouse is anesthetized and sacrificed and the brain is sectioned and stained, and infarct volume is measured. Neurological outcome and infarct size is compared between control and treatment groups.

The above experiments may be repeated using apoE deficient mice.

EXAMPLE 9

In Vivo Treatment of Global Ischemia

A murine model of global ischemia, adapted from the rat two vessel occlusion model of global ischemia, is used to assess the effects of intrathecal administration of small therapeutic peptides (fewer than 30 amino acids in length) comprising the apoE LDL receptor region. One such peptide has SEQ ID NO:6.

Wild-type mice (21±1 grams) are fasted overnight, anesthetized with halothane or another suitable anesthetic, intubated and mechanically ventilated. The right internal jugular vein and femoral artery are cannulated. Pericranial temperature is held at 37.0 C. The carotid arteries are occluded and mean arterial pressure is reduced to 35 mmHg with 0.3 mg intra-arterial trimethaphan and venous exsanguination. Ten minutes later ischemia is reversed. Control mice receive no additional treatment, test mice receive intrathecal, intravenous or intraperitoneal injection of a therapeutic peptide. Peptides may be injected at varying doses, using the in vitro data provided herein as a guide.

Each animal is evaluated neurologically at a predetermined time (e.g., 1, 3 or 5 days after reperfusion), using known neurological testing procedures (see, e.g., Laskowitz et al., *J. Cereb. Blood Flow Metab.* 17:753 (July 1997)). After neurological evaluation, each animal is anesthetized and sacrificed and the brain injury is assessed using methods known in the art.

For example, brains may be perfusion fixed in situ, then sectioned, stained and examined by light microscopy, for example, to determine injury to the CA 1 sector of the hippocampus, and viable and non-viable neurons counted and compared.

Neurological outcome and brain injury is compared between control and treatment groups.

EXAMPLE 10

Apolipoprotein E and ApoE-Mimetic Peptides Initiate a Calcium-Dependent Signaling Response in Macrophages This example shows that apoE initiates a signaling cascade in murine peritoneal macrophage that is associated with mobilization of intracellular $Ca^{2+}$ stores following increased production of inositol trisphosphate. This cascade was inhibited by pretreatment with receptor-associated protein and $Ni^{2+}$. Signal transduction was mediated by a pertussis toxin-sensitive G protein. These are characteristic properties of signal transduction induced via ligand binding to the lipoprotein receptor-related protein (LRP) receptor. A peptide derived from the receptor binding region of apoE also initiated signal transduction in the same manner as the intact protein. The presence of cross desensitization suggested that the apoE and the apoE-mimetic peptide competed for the same binding site. This was confirmed by our observation that radiolabeled apoE-mimetic peptide competed with the intact protein for receptor binding. These data indicates that ApoE-dependent signal transduction mediates the immunomodulatory properties of this lipoprotein.

Materials and Methods

Materials. Brewer's thioglycollate broth was purchased from Difco Laboratories (Baltimore, Md.). RPMI Medium 1640, fetal bovine serum, Hanks' Balanced Salt Solution and other cell culture reagents were purchased from Life Technologies, Inc. (Grand Island, N.Y.). Bovine serum albumin (BSA), pertussis toxin, and HEPES were from Sigma Chemical Co. (St. Louis, Mo.). Fura-2AM and BAPTA/AM were obtained from Molecular Probes (Eugene, Oreg.). Myo-[2-$^3$H]inositol (specific activity 10-20 Ci/mmol) was purchased from American Radiolabeled Biochemicals (St. Louis. Mo.). A plasmid containing the RAP cDNA was a kind gift from Dr. Joachim Herz, the University of Texas, Southwestern, Dallas Tex. It was used to produce RAP as previously described [21]. Human recombinant apoE2 was obtained commercially from Panvera Corp (Madison, Wis.). The preparation was free of endotoxin, and homogenous as judged by SDS-polyacrylamide gel electrophoresis. [$^3$H]thymidine (specific activity, 70 Ci/mmol) and Iodine-125 (specific activity: 440 mCi/mg) were purchased from the American Radiolabeled Chemicals, Inc. (St. Louis Mo.). The 20 amino acid ApoE mimetic peptide (Ac-TEELRVRLASHLRKLRKRLL-amide) with and without a tyrosine on the amino terminus as well as a scrambled control peptide of identical size, amino acid composition, and purity were synthesized by QCB Biochemicals (Hopkinton, Mass.) to a purity of 95%. All amino termini were acetylated and all carboxyl termini were blocked with an amide moiety. Peptides were reconstituted in sterile isotonic phosphate buffered saline. A scrambled control peptide of identical size, amino acid composition, and purity was also synthesized. All other reagents used were of the highest quality commercially available.

Macrophage Harvesting. All experiments involving animals were first approved by the Duke Institutional Animal Care and Use Committee. Pathogen-free female C57BL/6 mice and ApoE deficient mice previously backcrossed 10 times to the C57BL/6 strain were obtained from the Jackson Laboratory (Bar Harbor, Me.). Thioglycollate-elicited peritoneal macrophages were harvested by peritoneal lavage using 10 ml of ice-cold Hanks' balanced salt solution containing 10 mM HEPES and 3.5 mM NaHCO$_3$ (HHBSS), pH 7.4. The macrophages were pelleted by centrifugation at 4° C. at ~800×g for 10 min and resuspended in RPMI 1640 media supplemented with 25 mM HEPES, 12.5 U/ml penicillin, 6.5 mg/ml streptomycin, and 5% fetal bovine serum. Cell viability was determined by the trypan blue exclusion method and was consistently greater then 95%.

Receptor Binding Studies. Macrophages were plated in 48-well cell culture plates (Costar) at 2.5×10$^5$ cells per well and incubated for 3 h at 37° C. in a humidified 5% CO$_2$ incubator. The plates were then cooled to 4° C. and unbound cells were removed by three consecutive rinses with ice-cold Hanks' balanced salt solution containing 20 mM Hepes and 5% BSA, pH 7.4 (binding buffer). To quantify direct binding of the $^{125}$I-apoE mimetic peptide, varying amounts of radiolabeled peptide were added to each well in the presence or absence of 200-fold molar excess of unlabeled peptide. Specific binding to cells was determined by subtracting the amount of $^{125}$I-apoE peptide bound in the presence of excess unlabeled peptide (nonspecific binding) from the amount of $^{125}$I-apoE peptide bound in the absence of excess unlabeled peptide (total binding). For competition studies, 50 nM radiolabeled peptide was added to each well in the presence or absence of varying amounts (31.25 nM-4 µM) of unlabeled ApoE2 or P. Cells were then incubated at 4° C. for 12-16 h. Unbound ligand was removed from the wells and the cell monolayer was rinsed three times with ice-cold binding buffer. Cells were then solubilized with 1 M NaOH, 0.5% SDS at room temperature for >5 h before the contents of each well was added to polystyrene tubes and counted in a LKB-Wallac, CliniGamma 1272 γ-counter (Finland).

Measurement of $[Ca^{2+}]_i$ in apoE and peptide treated macrophage. Changes in $[Ca^{2+}]_i$ levels in Fura-2/AM treated single cells were quantified using digital imaging microscopy in accordance with known techniques. Macrophages were plated on glass coverslips sitting in 35 mm Petri dishes at a density of 1.5×10$^5$ cells/cm$^2$, and allowed to adhere for 2 h in a humidified 5% CO$_2$ incubator at 37° C. The non-adherent cells were aspirated and the monolayers were washed twice with HHBSS. 4 µM Fura-2/AM was incubated with the cells for thirty min in the dark at room temperature and $[Ca^{2+}]_i$ was subsequently measured using a digital imaging microscope in accordance with known techniques. After obtaining baseline measurements for 5 min, ligand (apoE, apoE mimetic peptide, or scrambled peptide) was added, and multiple $[Ca^{2+}]_i$ measurements were taken. To determine if signaling resulted from ligation of the ligand to LRP, cells were preincubated with a 1000-fold molar excess of RAP or 10 mM NiCl$_2$, both of which inhibit ligand binding to LRP, for 5 min prior to stimulation with apoE or peptide. In experiments in which the involvement of a G protein was assessed, monolayers were incubated with 1 µg/ml pertussis toxin for 12 h at 37° C. and Ca$^{2+}$ measurements were made as stated above.

Measurement of IP$_3$ in apoE treated macrophage and effect of pertussis toxin. The formation of IP$_3$ in myo-[2-$^3$H]inositol-labeled macrophages under various experimental conditions was quantified in accordance with known techniques. Macrophage were plated in 6 well plates (4×10$^6$ cells/well) and allowed to adhere at 37° C. for 2 h in a humidified 5% CO$_2$ incubator. Medium was aspirated from the monolayers and RPMI 1640 medium containing 0.25% BSA and myo-[2-$^3$H] inositol (specific activity 10-20 Ci/mmol) was added to each well. The cells were incubated at 37 (C for an additional 16-18 h. Monolayers were rinsed three times with 25 mM HHBSS containing 1 mM CaCl$_2$, 1 mM MgCl$_2$, 10 mM LiCl, pH 7.4. A volume of 0.5 ml of this solution was added to each well, and the cells were preincubated for 3 min at 37° C. before stimulated with ligand. The reaction was stopped by aspirating the medium containing the ligand and adding 6.25% perchloric acid. The cells were scraped out of the wells, transferred to tubes containing 1 ml of octylamine/Freon (1:1 vol/vol) and 5 mM EDTA, and were centrifuged at 5600×g for 20 min at 4° C. The upper phase solution was applied to a 1 ml Dowex resin column (AG 1-X8 formate; Bio Rad Laboratories, Richmond, Calif.) and eluted sequentially in batch process with H$_2$O, 50, 200, 400, 800, and 1200 mM ammonium formate containing 0.1 M formic acid [26]. Radioactivity was determined by placing aliquots in a liquid scintillation counter to determine radioactivity. To evaluate the pertussis-toxin sensitivity of the G protein coupled to receptor activation and phosphatidyl inositol 4,5-bisphosphate (PIP$_2$) hydrolysis, cells were plated as described above and incubated with µg/ml pertussis toxin which had been preactivated with 40 mM DTT at 30° C. for 20 min. The effect on IP$_3$ formation was measured as described above.

Competition between apoE and apoE mimetic peptide for binding site on the receptor. Changes in macrophage $[Ca^{2+}]_i$ upon stimulation with apoE and apoE-mimetic peptide were studied to determine whether these ligands bind to the same receptor. Fura-2/AM loaded macrophages were incubated overnight, plated on glass cover slips, stimulated with one ligand, and changes in $[Ca^{2+}]_i$ quantified. Cells were then stimulated with second ligand and Ca$^{2+}$ measurements repeated.

Results

Figure 8A:
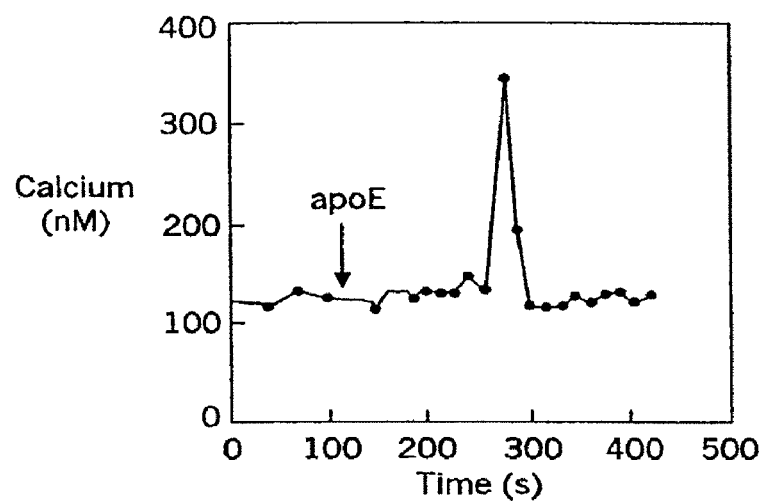
FIG. 8. Changes in $[Ca^{2+}]_i$ in macrophages treated with apoE. Panel A: Changes in $[Ca^{2+}]_i$ in a single Fura-2/AM loaded peritoneal macrophage on stimulation with apoE (100 pM). Details for measuring $[Ca^{2+}]_i$ are described in the Examples below. The graph shown is representative of 5 individual experiments using 20-30 cells each. Approximately 70-80% of the macrophage demonstrated changes in $[Ca^{2+}]_i$ upon stimulation with apoE. The arrow indicates the time of addition of apoE. Panel B: Effect of apoE concentration on changes in $[Ca^{2+}]_i$. The changes in $[Ca^{2+}]_i$ in individual cells were measured prior to and following exposure to varying concentrations of apoE. The data are displayed as mean (S.E.) and are representative of two independent experiments; in each case 25-30 cells were analyzed cells per study.
Figure 8B:
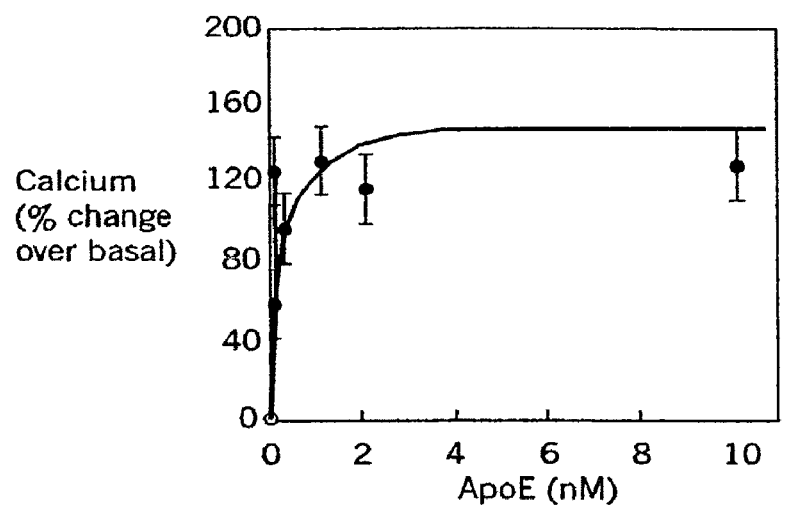

Effect of apoE on macrophage $[Ca^{2+}]_i$. Modulation of free cytoplasmic Ca$^{2+}$ concentration is a ubiquitous signaling response. In many cell types, binding of ligands to plasma membrane receptors activates the hydrolysis of PIP$_2$ by membrane-bound phospholipase C, generating IP$_3$. IP$_3$ causes the release of Ca$^{2+}$ from the endoplasmic reticulum by binding to its cognate receptor, which is also a Ca$^{2+}$ channel. In non-excitable cells, $[Ca^{2+}]_i$ signaling is associated both with Ca$^{2+}$ release from intracellular stores and Ca$^{2+}$ influx. Treatment of macrophages with human recombinant apoE increased $[Ca^{2+}]_i$ levels 2-4-fold compared to macrophage treated with buffer (FIG. 8A). In a typical experiment $[Ca^{2+}]_i$ levels in unstimulated cells and apoE-treated cells were 95.33±7.37 and 180.25±14.57 nM, respectively. The increase in $[Ca^{2+}]_i$ upon stimulation with apoE was observed in 70-80% of the cells examined. ApoE-induced increase in $[Ca^{2+}]_i$ was heterogeneous, asynchronous, and either oscillatory or sustained. ApoE-induced increases in macrophage $[Ca^{2+}]_i$ was dose-dependent (FIG. 8B). To address the possibility that native apoE secreted by macrophage altered responses to exogenous human recombinant apoE, these experiments were repeated using macrophage prepared from apoE deficient mice. Calcium responses following stimulation with apoE were identical in wild-type macrophages and macrophages from apoE deficient mice (data not shown).

Figure 9A:
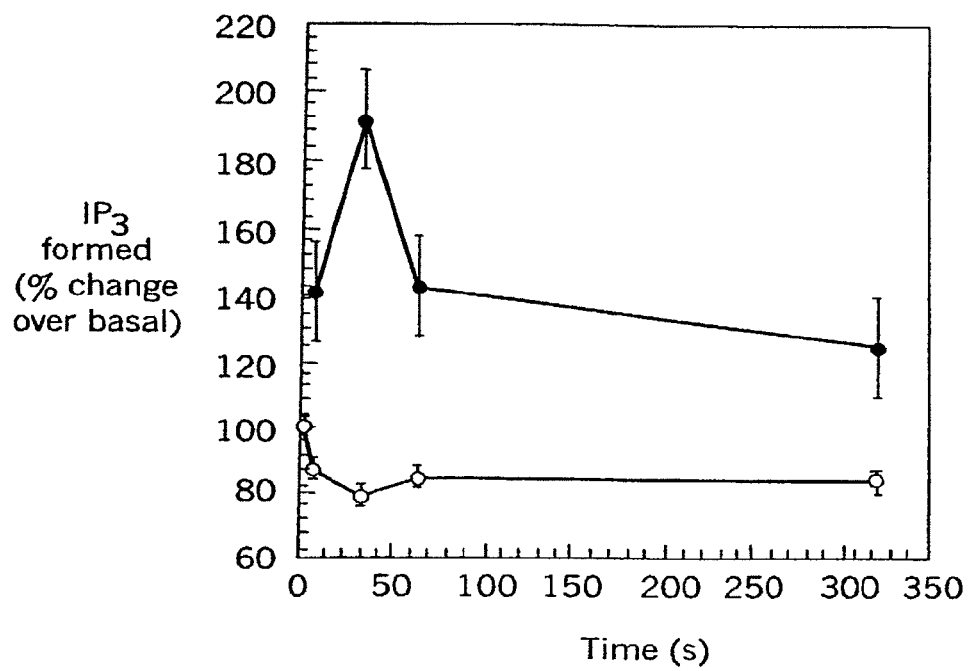
FIG. 9. Changes in $IP_3$ in macrophages treated with apoE. Panel A: Effect of apoE on $IP_3$ synthesis in macrophages, and modulation by pertussis toxin. These results are representative of two independent experiments performed in duplicate and expressed as % change in $IP_3$ formation at different time periods in myo-[2-$^3$H]inositol-labeled cells stimulated with apoE (100 pM) in the presence (open circles) and absence (filled circles) of pertussis toxin. Panel B: Effect of apoE concentration on IP3 formation in [$^3$H]labeled macrophages. The cells were stimulated with varying concentrations of apoE for 60 s and $IP_3$ determined. Results are displayed as mean (S.E.) and are representative of two individual experiments performed in duplicate.
Figure 9B:
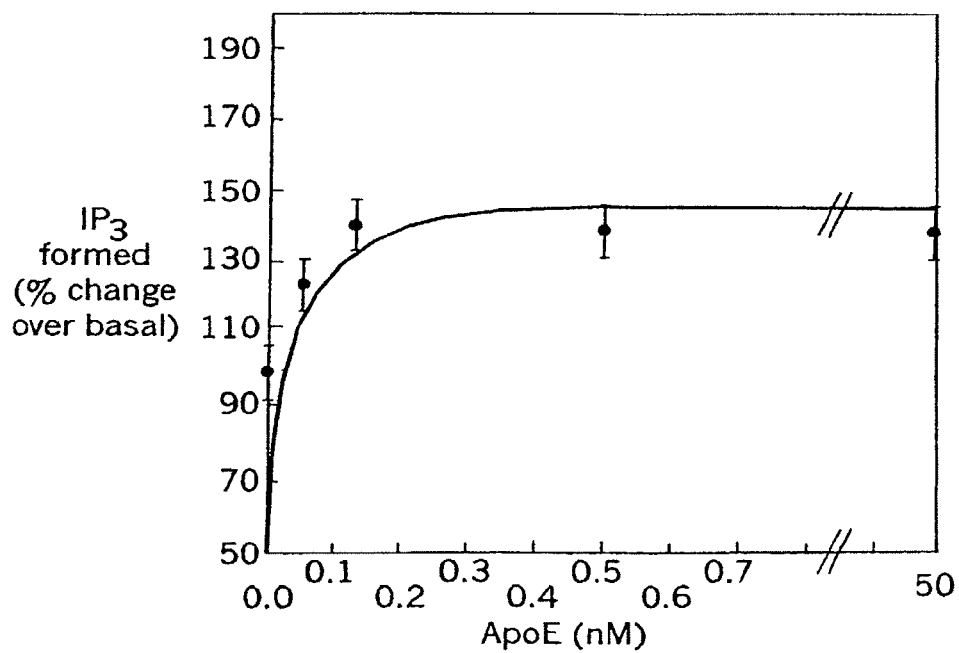

The effect of pertussis toxin on apoE-induced IP$_3$ synthesis. Exposure of myo-[2-$^3$H] inositol-labeled macrophage to apoE caused a 1.5-2.0-fold increase in IP$_3$ levels (FIG. 9A). This effect was dose-dependent (FIG. 9B). Pretreatment of the macrophages with pertussis toxin completely abolished this increase in IP$_3$. (FIG. 9A). These studies demonstrate that the phospholipase C-catalyzed hydrolysis of membrane PIP$_2$ in apoE stimulated cells is coupled to a pertussis toxin-sensitive G protein.

ApoE-induced increases in macrophage $[Ca^{2+}]_i$ are attenuated by Ni$^{2+}$ and Rap. Previous studies have demonstrated that ApoE binds to LRP and is then internalized. Additionally, binding of lactoferrin, *Pseudomonas* exotoxin A, lipoprotein lipase and thrombospondin to LRP initiates a signaling cascade associated with the generation of second messengers. To investigate the possibility that LRP is involved in the signal cascade induced by apoE, macrophages were preincubated with RAP and $Ni^{+2}$ prior to stimulation with apoE2 or apoE2 mimetic peptide. RAP is a 39 kD protein that blocks the binding of all known ligands to LRP. $Ni^{2+}$ also blocks ligand interactions with LRP. Both preincubation with RAP and $Ni^{+2}$ markedly attenuated the $[Ca^{2+}]_i$ increases associated with subsequent exposure to apoE (data not shown). These results are consistent with the hypothesis that apoE induces a signaling cascade via specific interaction with LRP. Pretreatment of macrophage with pertussis toxin also markedly attenuated the ApoE-dependent $Ca^{2+}$ response, indicating that signal transduction induced by apoE is coupled to a pertussis toxin-sensitive G protein. This is consistent with the known properties of LRP-dependent signal transduction.

Effect of apoE-mimetic peptide on macrophage $[Ca^{2+}]_i$. Stimulation of macrophage with the peptide derived from residues 130-149 of the apoE receptor binding region also resulted in a 2-3-fold increase in $[Ca^{2+}]_i$, whereas a scrambled control peptide of identical size and composition had no effect (data not shown). This increase in $[Ca^{2+}]_i$ was observed in approximately 60-70% of cells examined. As with the apoE responses, peptide-induced increases in macrophage $[Ca^{2+}]_i$ were heterogeneous and asynchronous. These results demonstrate that both intact apoE and a peptide derive from the apoE receptor binding region induce an increase in $[Ca^{2+}]_i$ that is consistent with the initiation of a signaling cascade. However, on a molar basis, higher concentrations of peptide were necessary to get $[Ca^{2+}]_i$ responses compared to the intact apoE. This difference likely results from differences in receptor affinity between the peptide and apoE, a property generally seen when comparing the effects of intact proteins to peptide ligands.

Effects of repeated stimulation of apoE and apoE-mimetic peptide on $[Ca^{2+}]_i$. We evaluated the possibility of competition between apoE and its mimetic peptide for binding sites on the receptor by quantifying the changes in $[Ca^{2+}]_i$ consequent to receptor ligation. Following repeated exposure to apoE, there was a marked attenuation in $[Ca^{2+}]_i$ suggesting tachyphylaxis (data not shown). Following the increase in $[Ca^{2+}]_i$ associated with the initial exposure to human recombinant apoE, there was a marked attenuation in $[Ca^{2+}]_i$ response to subsequent peptide exposure (data not shown). Similarly, there was a loss of $[Ca^{2+}]_i$ response to apoE addition following initial exposure to peptide (data not shown). No desensitization in calcium response was observed with exposure of scrambled peptide (data not shown). This observed tachyphylaxis suggests receptor desensitization secondary to receptor ligation, and is consistent with the hypothesis that both the intact apoE protein and the 20 residue peptide bind to the same receptor.

Discussion

The primary observations of this example are that: 1) binding to receptors on the macrophage cell surface of human recombinant apoE (in pM to nM concentrations) initiates signaling events associated with increases in $[Ca^{2+}]_i$ and $IP_3$; 2) a 20 residue peptide derived from the receptor binding region of apoE, but not a scrambled control peptide, causes identical changes in macrophage $[Ca^{2+}]_i$; 3) changes in $[Ca^{2+}]_i$ and $IP_3$ are specific and dose-dependent; 4) apoE-induced increase in cellular $IP_3$ is pertussis toxin-sensitive; and 5) changes in $[Ca^{2+}]_i$ are blocked by RAP and $Ni^{2+}$. Moreover, based on the presence of cross-desensitization, apoE and the apoE-mimetic peptide appear to bind to the same receptor.

EXAMPLE 11

An Apolipoprotein E Mimetic Peptide is Protective in a Murine Head Injury Model

This Example demonstrates a protective effect of intravenous administration of a 17 amino acid ApoE mimetic peptide (the fragment of ApoE containing amino acids 133-149 (SEQ ID NO: 10)) following head injury.

Mice were endotracheally intubated and their lungs were mechanically ventilated with 1.6% isoflurane at 30% partial pressure of oxygen. The mice received a midline closed head injury delivered by a pneumatic impactor at a speed of 6.8 m/s. Thirty minutes after closed head injury, mice were randomized into 3 groups (n=16 mice per group as follows: high dose peptide (406 ug/kg), low dose peptide (203 ug/kg), and saline control solution. All peptide solutions were prepared in sterile isotonic saline (100 ul) and delivered intravenously via tail vein injection. Rotorod time and weight were measured for five consecutive days after injury. At 21 days, the ability to learn to find a hidden platform in the Morris Water Maze was tested.

Figure 10A:
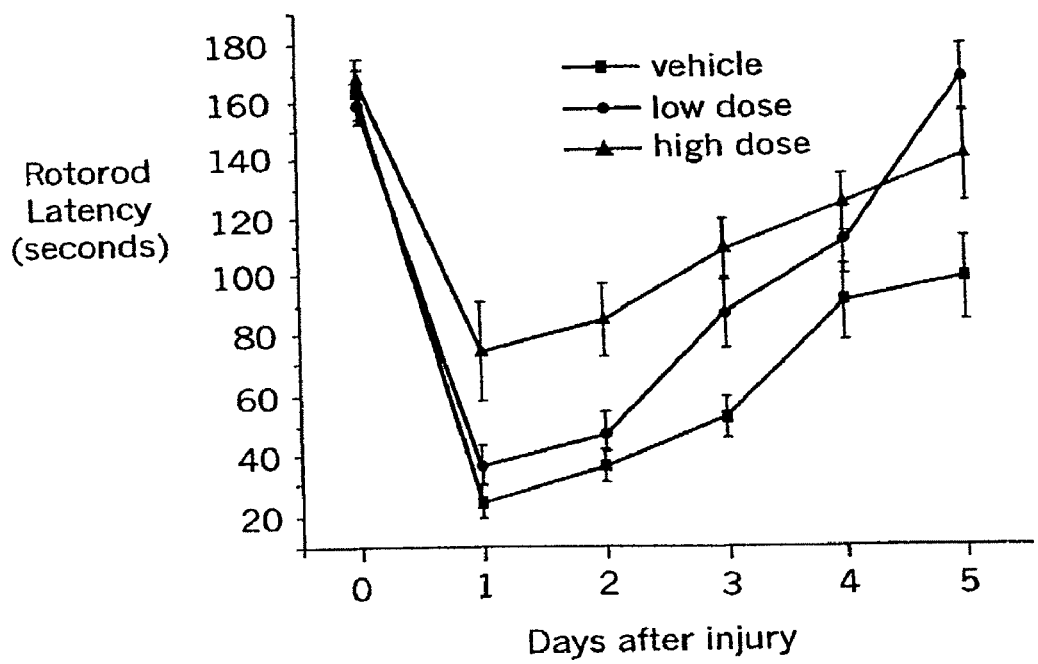
FIG. 10A shows the performance of mice with and without treatment on rotorod latency after closed head injury.
Figure 10B:
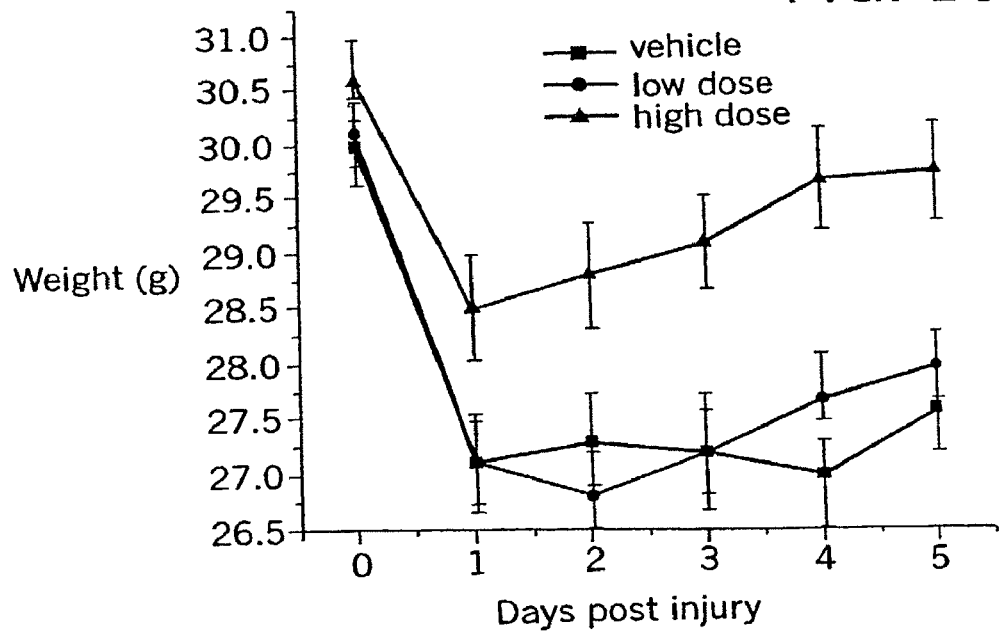
FIG. 10B shows the weight gain of mice with and without treatment after closed head injury.

Prior to injury, rotorod latency and weights were comparable in all animals. After injury, the saline injected animals had a profound deficit in rotorod testing which was associated with weight loss. High dose peptide, and to a lesser extent low dose peptide protected animals from this motor deficit (FIG. 10A), and concomitant weight loss (FIG. 10b). This protective effect of the single dose of peptide was sustained for five days following injury ($p<0.05$ 3-way repeat measures ANOVA).

Figure 10C:
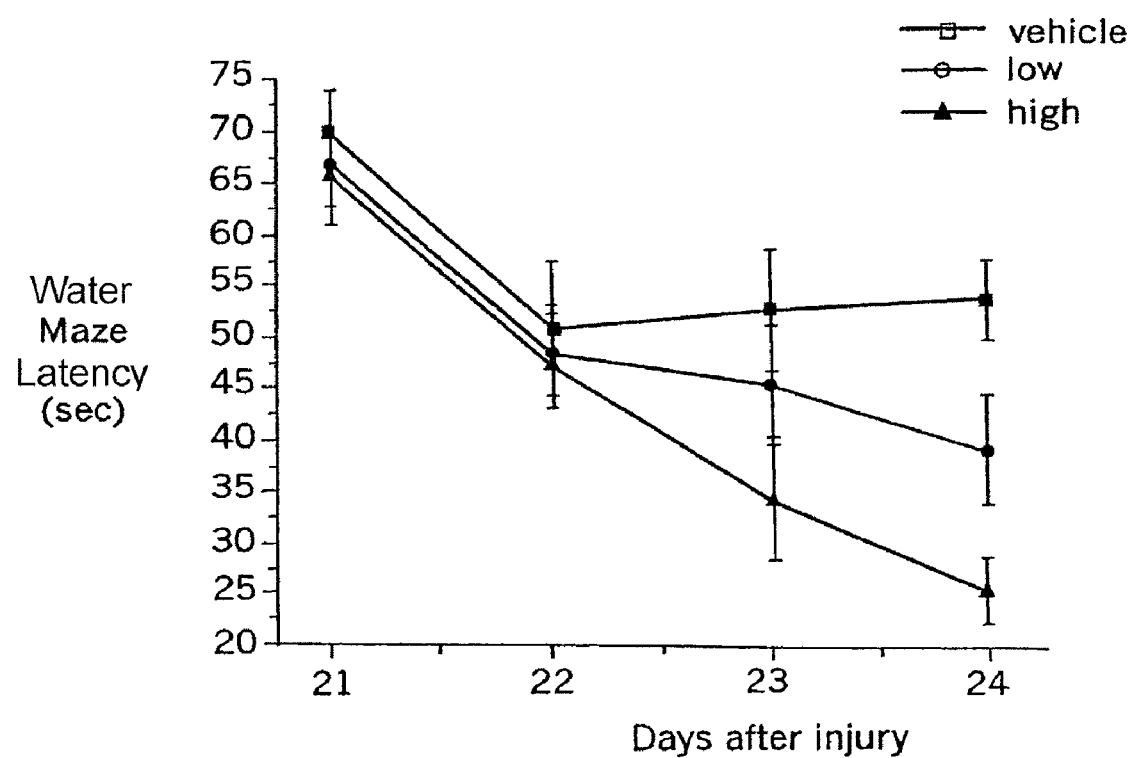
FIG. 10C shows the performance of mice with and without treatment in a water maze latency test after closed head injury.

In addition, the peptide appeared to provide protection in learning deficits in learning to find a hidden platform (FIG. 10C) in the Morris Water Maze ($p<0.05$ 3-way repeat measures ANOVA). Treatment with the peptide also resulted in a significant improvement in acute survival as demonstrated by Kaplan-Meier analysis (data not shown).

The foregoing examples are illustrative of the present invention, and are not to be construed as limiting thereof. The invention is described by the following claims, with equivalents of the claims to be included therein.

EXAMPLE 12

Protective Effect of Apolipoprotein E-Mimetic Peptides on N-Methyl-D-Aspartate Excitotoxicity in Primary Rat Neuronal/Glial Cell Cultures The present inventors hypothesized that one mechanism by which apoE might play a role in modifying the response of brain to ischemia is by protecting against glutamate excitotoxicity. Glutamate is believed to contribute to neuronal injury in the setting of ischemia. Of the different classes of glutamate-activated channels, specific activation of the N-methyl-D-aspartate (NMDA) receptor is believed to be primarily responsible for mediating calcium influx and exacerbation of neuronal injury in a variety of neuron types (Meldrum and Garthwaite, 1990).

To model the in vivo effects of ApoE in an experimental setting of cerebral ischemia, we examined the effects of biologically relevant concentrations of native human ApoE and peptides derived from the receptor-binding region of ApoE in a cell culture model of primary rat neocortical neurons and glia exposed to NMDA. Intact ApoE exhibited a modest dose-dependent reduction in NMDA induced cytotoxicity. By comparison, a seventeen residue ApoE-mimetic peptide exhibited enhanced neuroprotection relative to native ApoE and completely blocked both the calcium influx and cell death associated with NMDA exposure. Further truncation of the peptide at the amino terminus resulted in a progressive loss of neuroprotection from NMDA excitotoxicity. These results suggest that ApoE affects recovery of neuronal cells from ischemic injury following brain insult by protecting cells against glutamate toxicity. Furthermore, they implicate the use of ApoE-mimetic peptides as a therapeutic strategy following cerebral ischemia and other diseases and disorders associated with glutamate toxicity.

Experimental Procedures

All animal procedures were designed to minimize animal discomfort and numbers, and were approved by the Duke University Animal Care and Use Committee.

Preparation of Primary Neuronal-Glial Cultures

Primary neuronal-glial cultures were prepared from fetal Sprague-Dawley rat brains at 18 days of gestation as previously described (Pearlstein et al., 1998). Brains were harvested from 10-15 pups and dissected to separate cortex from meninges and subcortical structures using anatomical landmarks. Cortices were pooled and minced into 2 mm$^3$ pieces in a buffered salt solution supplemented with 20 mM HEPES buffer, pH 7.4, containing 0.25% trypsin. The tissue was incubated for 20 minutes at 37° C. in a 5% $CO_2$/95% room air atmosphere, and washed twice with ice-cold, glutamine-free minimum essential medium (MEM; Life Technologies) containing 15 mM glucose, 5% fetal bovine serum (GIBCO), 5% horse serum (GIBCO), and 1% DNase-I (Sigma Chemical Co., St. Louis, Mo., USA). Tissue pieces were dissociated by trituration through a fire-polished 9-inch Pasteur pipette (I.D.=0.7 mm). The resultant suspension was centrifuged at 50×g for 10 min, the supernatant discarded, and the pellet resuspended in growth medium (MEM supplemented with 15 mM glucose, 5% fetal bovine serum, and 5% horse serum). The dissociated cells were plated to achieve a confluent monolayer using 4×10$^5$ cells per well in poly-D-lysine coated, 24-well culture plates (Falcon 3047; Becton Dickinson Co., Lincoln Park, N.J., USA). Cultures were maintained undisturbed at 37° C. in a humidified 5% $CO_2$/95% room air atmosphere for 13-16 days prior to use. Cultures prepared according to this protocol were found to contain 54% neurons and 46% glia as determined by immunohistochemical staining for NF-160 and glial fibrillary acidic protein (Kudo et al., 2001).

Synthesis of Apo-E Peptides

Peptides were synthesized by QCB Biochemicals (Hopkinton, Mass.) to a purity of 95% and reconstituted in sterile isotonic phosphate buffered saline (PBS). For each peptide, the amino terminus was acetylated, and the carboxyl terminus was blocked with an amide moiety. The parent 17-residue peptide ApoE (133-149) (SEQ ID NO:10) was derived from the receptor-binding region of apoE. A scrambled control peptide of identical size, amino acid composition, and purity (Ac-LARKLRSRLVHLRLKLR-amide) (SEQ ID NO:14) was similarly created. The 14-residue sequence (136-149) and 11-residue sequence (139-149) (SEQ ID NO:11) were made by progressively truncating the amino terminus of the parent (133-149) (SEQ ID NO:12) peptide.

Exposure to NMDA/Cytotoxicity Assessment

Mature cultures (13-16 days in vitro) were washed with $Mg^{2+}$-free buffered salt solution (BSS) containing 20 mM HEPES buffer (pH7.4) and 1.8 mM $CaCl_2$, prior to the addition of NMDA. Following NMDA exposure, cultures were maintained for 30 minutes at 37° C. in a 5% $CO_2$/95% air atmosphere. The medium containing NMDA was then removed and replaced with MEM supplemented with 20 mM glucose. The cultures were returned to the incubator for 24 h.

In all experiments, cellular damage was assessed at 24 h after exposure to NMDA by measurement of the activity of lactate dehydrogenase (LDH) released into the medium as described below. The non-competitive NMDA receptor antagonist, MK-801 (Tocris Cookson Ins., St. Louis, Mo.) at a concentration of 10 μM was used as a positive control. Preliminary dose-response studies were performed to determine the concentration of NMDA (100 μM) required to effect a near-maximal LDH release ($ED_{90}$) as used in the present study.

Assessing Effect of apoE and apoE-Mimetic Peptide on NMDA Toxicity

The effect of human recombinant apoE (Panverra, Madison, Wis.) on 100 μM NMDA-induced LDH release was assessed and the dose-response curve was obtained (apoE: 0.1-10 μM final concentration). ApoE3, the most common human isoform, was added to the cultures 30 minutes prior to and removed following NMDA exposure. The effect of apoE peptide (133-149) on NMDA (100 μM or 300 μM)-induced LDH release was next assessed and the dose-response curve was obtained in a separate set of sister cultures that were simultaneously treated under one of the following conditions: (1) various doses of peptide (0.3 μM, 1 μM, 3 μM, 6 μM, 10 μM final concentration) were added to the culture immediately prior to and removed at the end of NMDA exposure; (2) no peptide, NMDA exposure; (3) no peptide, no NMDA exposure; (4) no peptide, NMDA exposure with 10 μM MK-801 for 30 minutes. The effect of a scrambled control peptide on NMDA-induced LDH release was similarly assessed.

The effect of time of administration of apoE peptide (133-149) on NMDA-induced LDH release was assessed in a separate set of sister cultures that were simultaneously treated under one of following conditions: (1) peptide was added to the culture medium 24 h prior to and removed immediately before exposure to NMDA; (2) peptide was added immediately prior to and removed at the end of the NMDA exposure; (3) peptide was added immediately following the 30 minutes NMDA exposure; (4) no peptide, NMDA exposure; (5) no peptide, no NMDA exposure. In all cases, peptide concentration was 6 μM, cultures were exposed to 100 μM NMDA for 30 minutes at 37° C., and the effect of treatment/exposure was examined 24 h after NMDA exposure as described above.

Measurement of LDH Release

Cellular injury was quantitatively assessed 24 h after excitotoxic stress by measuring the amount of lactate dehydrogenase (LDH) released into overlying medium by damaged cells. LDH activity was determined by a modification of methods previously described (Amador et al., 1963). In brief, a 200 μl sample of culture medium was added to a polystyrene cuvette containing 10 mM lactate and 5 μmol of NAD in 2.75 ml of 50 mM glycine buffer (pH 9.2) at 24° C. LDH activity was determined from the initial rate of reduction of NAD as calculated using a linear least square curve fit of the temporal changes in fluorescence signal from the cuvette (340 nm excitation, 450 nm emission) and expressed in units of enzymatic activity (nmol of lactate converted to pyruvate per min). Analysis was performed on a fluorescence spectrophotometer (Perkin Elmer Model LS50B; Bodenseewerk GmbH, Uberlinger, Germany).

Effect of Peptides on Cellular Calcium Uptake

Cellular calcium uptake from the extracellular space was assessed using $^{45}CaCl_2$ (American Radiolabeled Chemicals, St. Louis, Mo.). After washing the cultures with $Mg^{2+}$-free BSS containing 20 mM HEPES buffer, 6 μM peptide or 10 μM MK-801 was added to each well prior to and removed at the end of 100 μM NMDA exposure. $^{45}Ca$ (0.28 μCi/ml, 0.9 μCi/well) was added to each well immediately prior to NMDA exposure. The cultures were returned to the incubator and maintained at 37° C. Twenty minutes later, the exposure medium was removed and each well was washed 3 times with ice-cold $Mg^{2+}$-free BSS containing 20 mM HEPES buffer. The cells were subsequently lysed by addition of 0.2% sodium dodecyl sulfate (SDS). An aliquot from each well was added to a liquid scintillation vial containing 10 ml Cytoscint™ (ICN, Biochemical Research Product, CA) and radioactivity was determined by scintillation counting and normalized to cell count.

Circular Dichroism

Circular dichroism spectra were recorded on an Aviv Model 202 circular dichroism spectrometer, using 1 mm pathlength quartz cuvettes. Peptide concentration was approximately 50 µM in a buffer of PBS. Spectra were taken at 273 K. Samples contained 50 µM peptide in phosphate-buffered saline (PBS) and spectra were recorded at 4° C. Percent helicities were calculated from the signal at 222 nm using the equation as previously described (Myers et al., 1997). Concentrations of peptide stock solutions were determined by quantitative amino-acid analysis, carried out by the Protein/DNA technology Center at the Rockefeller University.

Statistical Analysis

Multiple group comparisons were performed by one-way analysis of variance. When comparisons to single control group were needed, post hoc analysis was performed using Dunnet's test. Values are reported as mean±standard deviation. Significance was assumed when $P<0.05$.

Results

To investigate the ability of ApoE to protect cells from glutamate excitotoxicity in an experimental tissue culture model of cerebral ischemia, primary rat neuronal/glial cultures were preincubated with human recombinant ApoE prior to exposure of the cells to NMDA. Previous experiments performed in our laboratory failed to detect an isoform specific effect of human recombinant ApoE on NMDA-induced excitotoxicity in primary rodent neuronal/glial cultures (Aono et al, 2002). To this end ApoE3, the most common isoform (Corder et al, 1993), was used throughout the experiments described herein.

Figure 11:
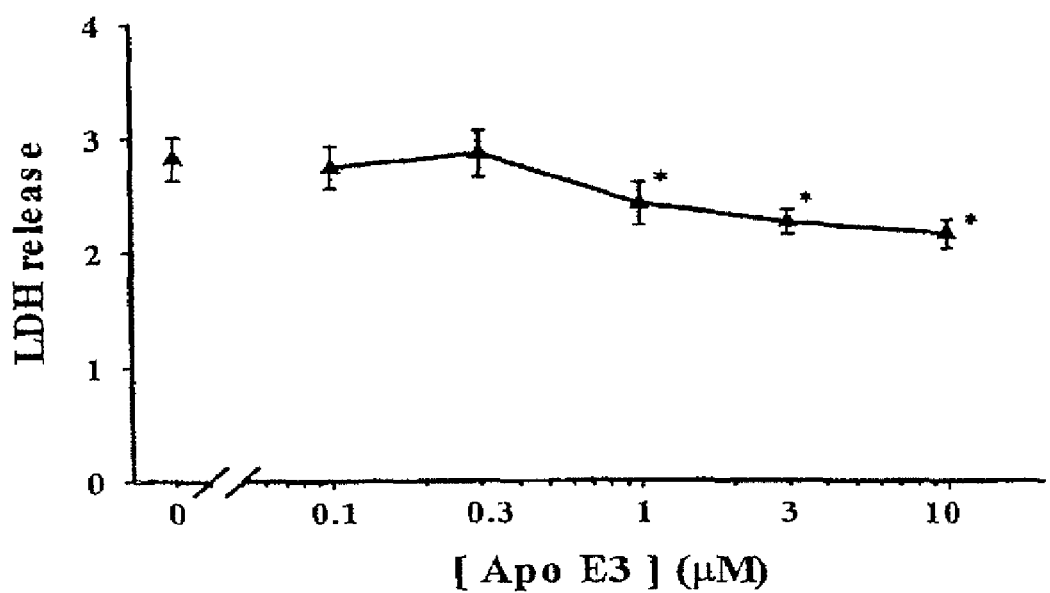
FIG. 11 shows the dose-response effect of human recombinant ApoE3 on NMDA-induced cell damage. Values=mean±s.d., N=6 culture wells per condition. *=P<0.05 compared to NMDA without ApoE3. Details for measuring NMDA-induced cell damage are provided in Examples below.

To determine the dose-response of ApoE3 on NMDA-induced cell damage, primary cultures were first preincubated with varying concentrations of apoE3 for 30 minutes prior to exposure with 100 µM NMDA (FIG. 11). Cellular injury was assayed 24 h following excitotoxic stress by measuring the amount of LDH released by damaged cells into the media (LDH release=nmols of lactate converted to pyruvate per min; see Experimental Procedures). Exposure of cultures to NMDA alone caused a significant increase in LDH release (2.82+/−0.19) compared to control untreated cells (1.01+/−0.06; $p<0.05$). Preincubation of the cultures with apoE3 provided a modest, dose-dependent reduction in LDH release which was significant at ApoE concentrations of 1-10 µM relative to NMDA alone ($p<0.05$, ANOVA followed by Dunnett's test). Hence, ApoE3 confers modest yet significant neuroprotection of primary rat neuronal/glial cultures from glutamate excitotoxicity.

Figure 12A:
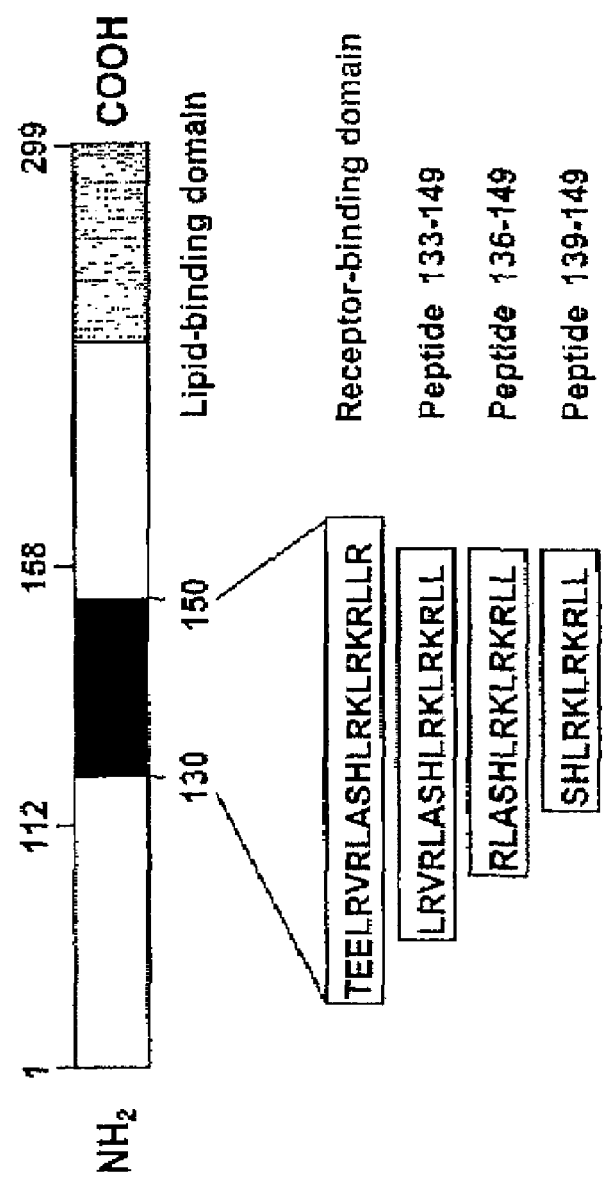
FIG. 12(A) is a schematic of full-length ApoE and ApoE-mimetic peptides. ApoE is represented by the open box. The 10-kDa lipid-binding domain is located at the carboxyl terminus and is denoted by the shaded region. The approximate region corresponding to the ApoE LDL receptor-binding domain is depicted by the solid box (amino acids 130-150, SEQ ID NO:13), followed by the sequences of the three truncated apoE-mimetic peptides used in these studies (SEQ ID NO: 10-12). (B) Circular dichroism spectra of ApoE peptides were recorded on an Aviv Model 202 CD spectrometer, using 0.1 cm pathlength cuvettes. CD spectra of the three peptides were consistent with a mixture of helical and random coil structure.
Figure 12B:
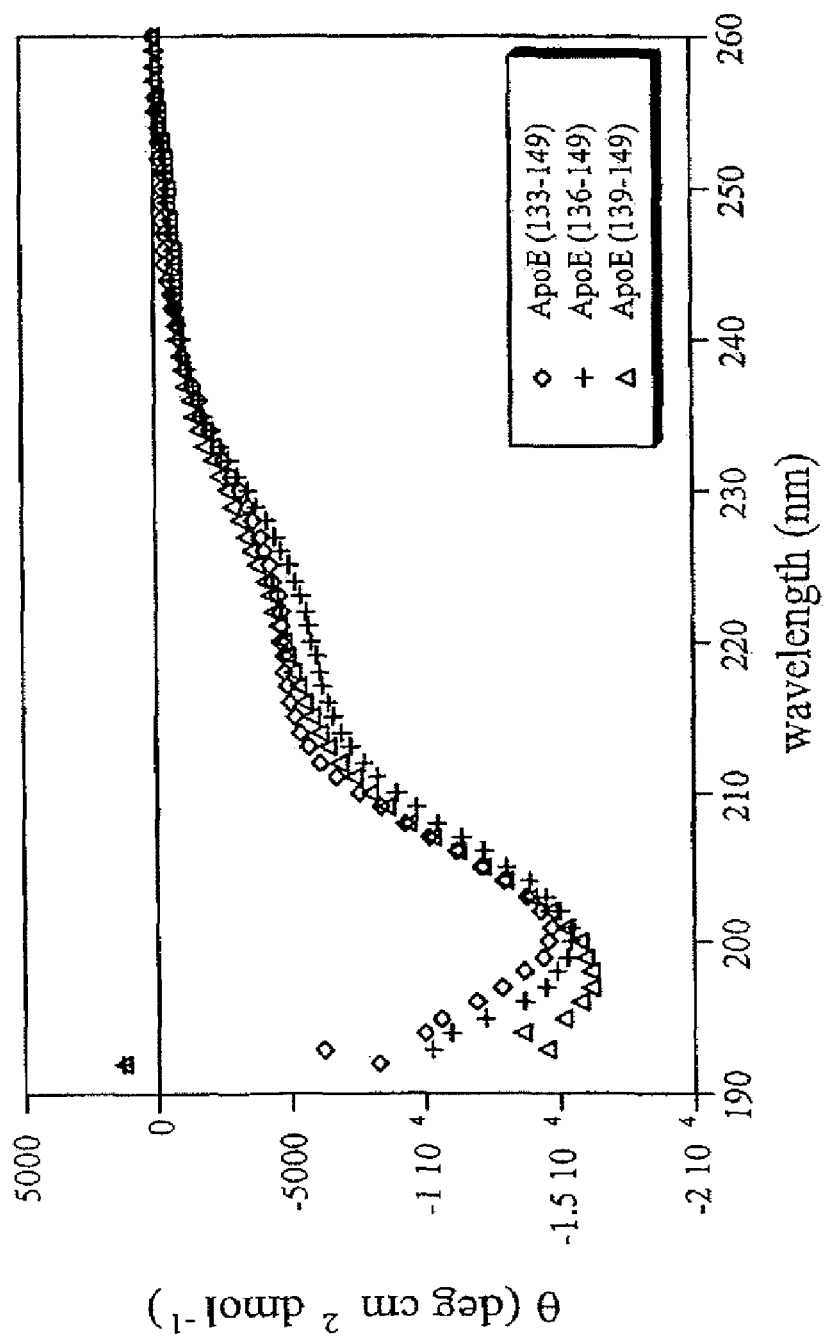

To test the hypothesis that small ApoE-mimetic peptides could similarly protect neuronal/glial cultures from NMDA excitotoxicity, we created a panel of three truncated apoE peptides derived from the receptor-binding region of apoE (FIG. 12A; ApoE 133-149, 136-149, 139-149). To assess the structural characteristics of the peptides and their helical content, we first carried out circular dichroism (CD) experiments (FIG. 12B). The CD spectra of the three peptides demonstrated evidence of significant helical structure, as evidenced by the significant minima at 222 nm and 208 nm. From these data we calculate that the three peptides have a comparable degree of helicity, with a 12-14% helical population in solution. Previous sedimentation equilibrium experiments performed in our laboratory demonstrate that these peptides exist as monomers in solution, indicating that the observed helical structure is not due to self-association of the peptide into helical oligomers (Laskowitz et al., 2001).

Figure 13:
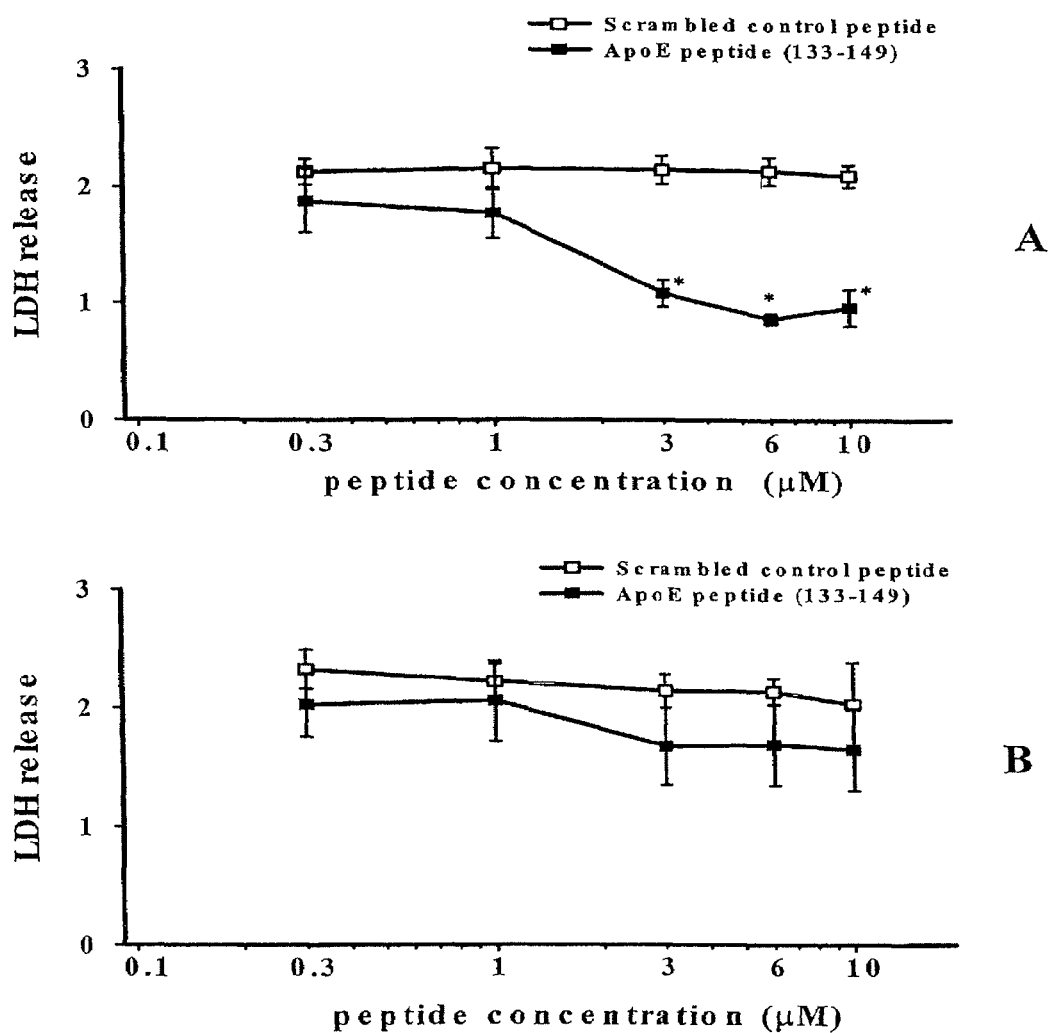
FIG. 13 contains graphs showing the dose response effect of ApoE peptide (133-149) (SEQ ID NO:10) on NMDA-induced cell damage of primary mixed neuronal-glial cultures at (A) 100 µM NMDA or (B) 300 µM NMDA. Values=mean±s.d., N=6-8 culture wells per condition. =P<0.05 compared to NMDA without peptide.

We first investigated the effect of the peptide ApoE (133-149) on NMDA-induced cell damage in primary neuronal/glial cultures (FIG. 13). This peptide was previously shown by our group to possess a bioactivity capable of modulating murine microglial function (Laskowitz et al, 2001). Primary rat neuronal/glial cultures were first preincubated with ApoE (133-149) 30 minutes prior to NMDA exposure and LDH release was assayed 24 h later. Exposure of cultures to 100 µM NMDA in the absence of ApoE (133-149) caused a two-fold increase in LDH release (1.74+/−0.06) relative to unexposed control cells (0.88+/−0.10; $p<0.05$) (FIG. 3A). In contrast to intact ApoE3 which was only modestly protective, addition of the 17-residue ApoE peptide provided robust, dose-dependent protection against 100 µM NMDA toxicity.

Protection from glutamate toxicity was first observed using a 3 µm ApoE (133-149) peptide concentration with maximal protection observed at 6 µM apoE (133-149) ($p<0.05$, ANOVA followed by Dunnett's test). As expected, no protection was observed in the presence of the scrambled control peptide. Surprisingly, treatment of cultures with apoE (133-149) failed to protect cells at any peptide concentration when cultures were exposed to 300 µM NMDA exposure (FIG. 13B). These results demonstrate that an ApoE mimetic peptide comprising 17 amino acid residues derived from the receptor-binding domain of ApoE is neuroprotective following NMDA-induced excitotoxicity. Furthermore, the peptide conferred greater protection to cultures than the intact holo-protein.

Figure 14:
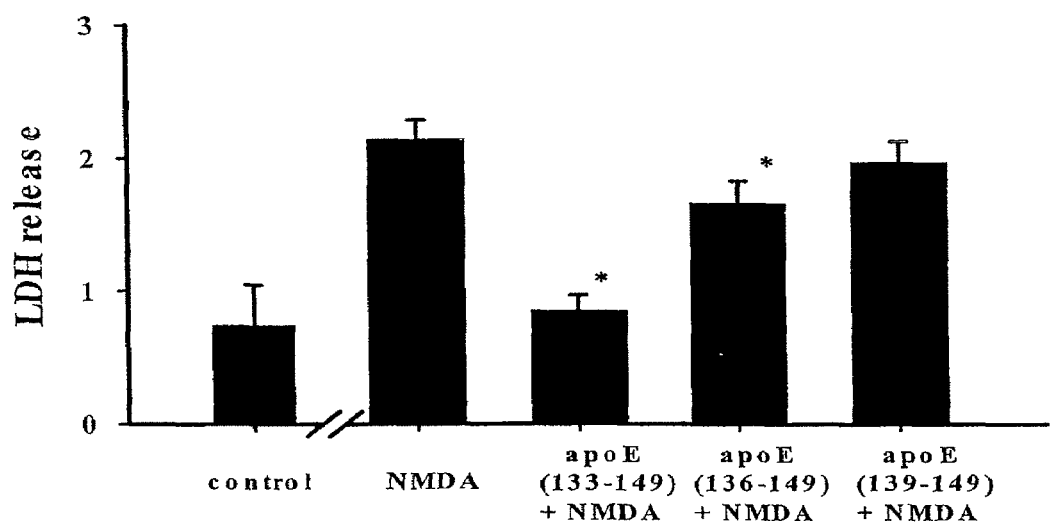
FIG. 14 is a graph showing the effect of truncations of ApoE peptide on NMDA-induced cell damage. Values=mean±s.d., N=8 culture wells per condition. *=P<0.05 compared to NMDA without peptide.

To further define the peptide domain required for neuroprotection in our primary culture system, we compared the effects of truncated ApoE peptides on NMDA-induced cell damage (FIG. 14). Removal of the three amino-terminal residues from the 17 residue peptide generated ApoE (136-149), a 14 amino acid peptide (FIG. 12A). Treatment with 6 µM ApoE (136-149) conferred modest protection against NMDA toxicity relative to the 17-residue parent peptide, ApoE (133-149), which completely blocked 100 µM NMDA-induced cell death (FIG. 14). By contrast, deletion of three additional amino terminal residues resulted in an 11-residue peptide, ApoE (139-149), which possessed no detectable bioactivity (ANOVA followed by Dunnett's test; $p<0.05$). These results indicate that truncations from the amino terminus of the 17 residue peptide ApoE (133-149), resulted in a progressive loss of neuroprotection against NMDA excitotoxicity, and that the amino acid domain ApoE (133-136) is necessary for the ApoE peptide to retain bioactivity.

Figure 15:
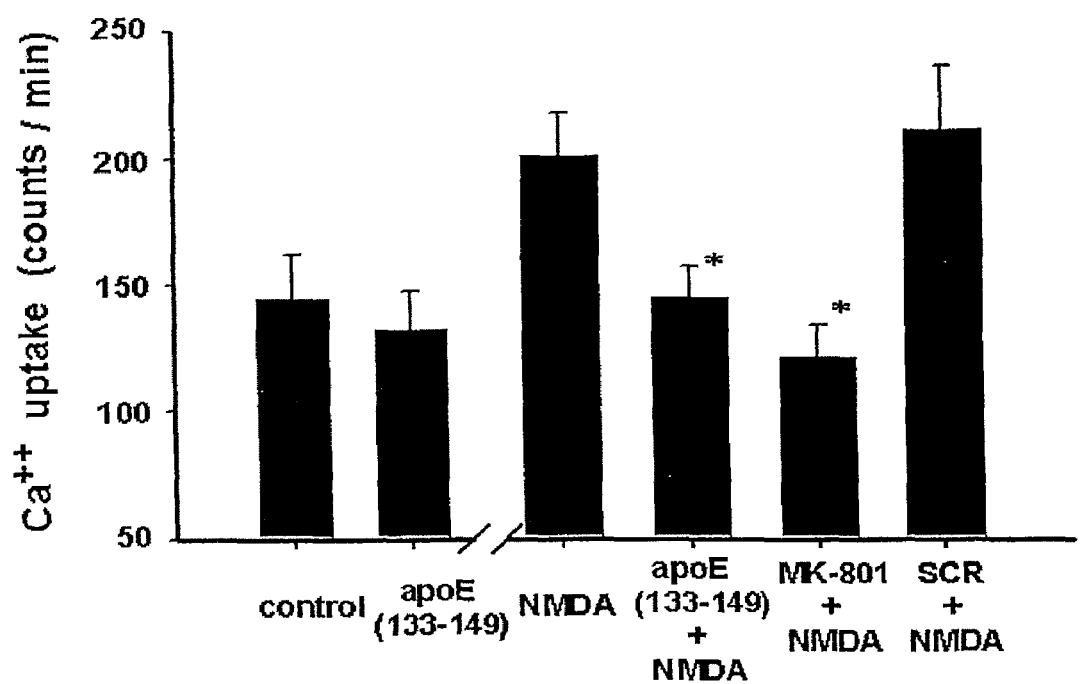
FIG. 15 is a graph showing the effect of ApoE peptide (133-149) on NMDA-induced $Ca^{++}$ uptake by primary mixed neuronal-glial cultures. Values=mean±s.d., N=8 culture wells per condition. *=P<0.05 compared to NMDA without peptide.

To investigate whether the parent ApoE-mimetic peptide exerted its protective effects by modulating calcium influx associated with NMDA exposure, we measured calcium uptake following incubation of the cells with ApoE (133-149) and 100 µM NMDA (FIG. 15). Calcium uptake was measured twenty minutes following exposure of the cultures to $^{45}Ca^{++}$ (see Experimental Procedures). Exposure of the cultures to 6 µM ApoE (133-149) in the absence of NMDA served as a control and had no direct effect on calcium influx (FIG. 15). Exposure of cultures to 100 µM NMDA in the absence of peptide induced calcium influx which was completely reversed by pretreatment with 10 µM MK-801 (FIG. 15).

Treatment with 6 μM ApoE (133-149) significantly decreased calcium influx compared to NMDA alone, whereas treatment with 6 μM scrambled control peptide had no effect on calcium influx (ANOVA followed by Dunnett's test; p<0.05). Hence, a 17-residue peptide derived from the receptor-binding domain of apoE is capable of protecting cells from the detrimental effects of calcium influx associated with NMDA-induced excitotoxicity.

Figure 16:
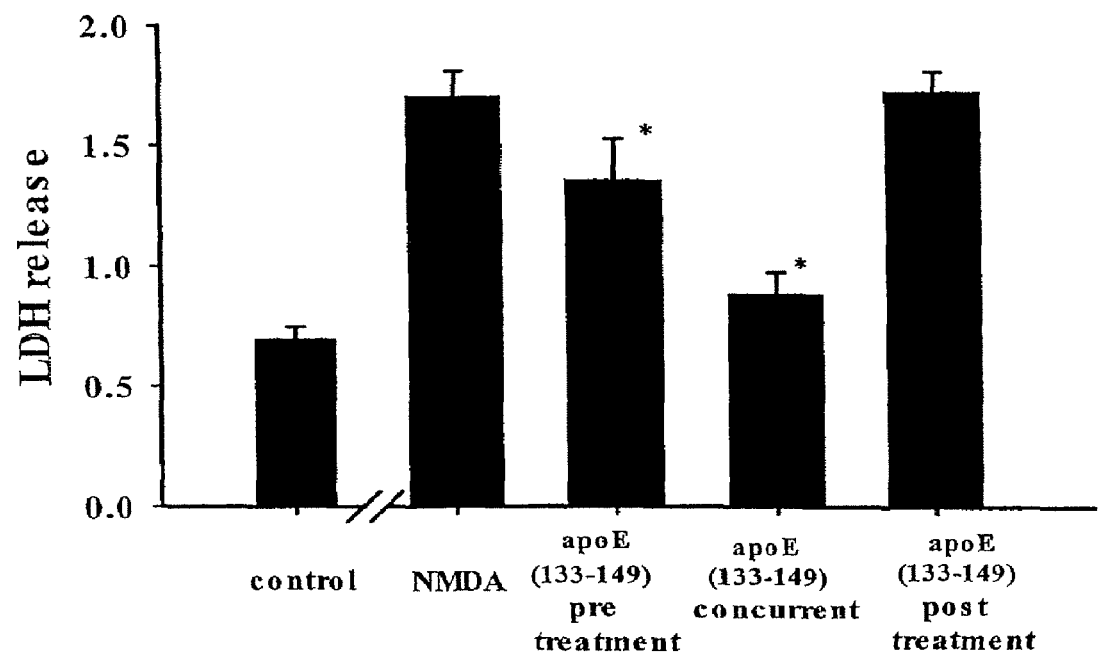
FIG. 16 is a graph showing the effect of timing of ApoE peptide (133-149) exposure on NMDA-induced cell damage. Cultures were pre-treated (peptide added 24 h prior to and removed immediately before NMDA exposure), treated concurrently (peptide added immediately prior to and removed immediately after NMDA exposure), or post-treated (peptide added immediately after NMDA exposure and maintained in the medium until determination of LDH released from damaged cells 24 h later) with 6 µM apoE peptide (133-149). Values=mean±s.d., N=8 culture wells per condition. *=P<0.05 compared to NMDA without peptide.

We next wished to examine the temporal relationship between administration of the ApoE-mimetic peptide and protection following NMDA exposure. To this end, ApoE (133-149) was added to cells either 24 hours prior to NMDA exposure, concurrently with NMDA, or post-NMDA exposure (FIG. 16; see Experimental Procedures). As before, a robust protection was observed when 6 μM ApoE (133-149) was administered concurrent with 100 μM NMDA (FIG. 16). Pretreatment of cultures with peptide 24 hours prior to NMDA exposure provided a modest but significant protection, whereas addition of ApoE (133-149) following NMDA exposure provided no protection. Thus, although ApoE (133-149) afforded modest protection when added 24 hours prior to NMDA exposure, administration of the peptide concurrently provided the best protection (ANOVA followed by Dunnett's test; p<0.05). Together, these results demonstrate that a monomeric peptide comprised of ApoE residues 133-149 can protect cells from glutamate excitotoxicity in an experimental tissue culture model of cerebral ischemia.

C. Discussion

In this study, we demonstrate that peptide sequences derived from the receptor-binding region of ApoE exert a protective effect against NMDA-mediated neuronal excitotoxicity in a tissue culture model of cerebral ischemia. This neuroprotective effect of the ApoE peptide was both specific and dose-dependent. At a concentration of 6 μM, a seventeen residue peptide, ApoE (133-149) blocked the neurotoxicity and calcium influx associated with exposure of primary neuronal-glial cultures to 100 μM NMDA as completely as the NMDA receptor antagonist MK-801.

Although there are multiple clinical reports demonstrating that apoE genotype influences neurological recovery in isoform-specific fashion, the mechanisms by which this occur remain poorly defined. It has been proposed that endogenbus apoE may influence the CNS response to injury by modifying oxidative stress (Miyata and Smith, 1996), exerting direct neurotrophic effects (Holtzman et al., 1995), downregulating the CNS inflammatory response (Lynch et al., 2001), or serving as a pathological chaperone by promoting cerebral amyloid deposition (Wisniewski and Frangione, 1992). In this report, we found that the intact ApoE protein also confers a modest degree of neuroprotection from NMDA-induced toxicity. This is in contrast with other recent studies, which failed to demonstrate any neuroprotective effect from the intact ApoE protein (Jordan et al., 1998; Lendon et al., 2000). These discordant results may in part be due to differences in methodology and experimental design. For example, Lendon et al. found that a 5 μg/ml concentration of ApoE failed to demonstrate additional neuroprotection beyond that of HDL alone, which itself conferred a modest benefit against NMDA-induced neurotoxicity. Unfortunately, in that study the effects of ApoE alone were not studied (Lendon et al. 2000). Jordan et al. also failed to demonstrate neuroprotection from ApoE in a model of NMDA-induced neurotoxicity. It is worth noting, however, that in these experiments, ApoE from conditioned media was used rather than human recombinant ApoE, and ApoE was preincubated for 5 days prior to NMDA exposure, as compared to 30 minutes in our study.

Our results suggest that biologically relevant concentrations of ApoE confer a modest degree of neuroprotection from excitotoxic cell death. Interestingly, the peptide derived from the receptor binding region of ApoE exerted a much more robust neuroprotective effect than the intact holoprotein, and completely blocked the cell death and calcium influx associated with the exposure of neocortical neurons to 100 μM NMDA. One explanation for our observations is that ApoE and the peptide fragments bound to the NMDA receptor. Although competitive antagonism of the NMDA receptor might explain the loss of neuroprotection of the peptide at higher excitotoxic burdens, competition at the NMDA receptor has never been demonstrated either for ApoE or for peptide fragments derived from ApoE.

Another plausible explanation is that these peptides exerted their biological activity against NMDA toxicity indirectly by interacting with specific cell surface receptors in the same manner as the intact ApoE holoprotein. ApoE is known to bind a family of cell surface receptors, including the LDL, VLDL, LRP/α2M, ER-2, and LR8 receptors (Kim et al., 1996; Novak et al., 1996). One region of ApoE which is critical for the interaction with the LDL receptor lies between residues 140-160 (Mahley, 1988), and site-specific mutagenesis studies of this region have demonstrated that mutations affecting charge and conformation can result in defective binding (Lalazar, 1988). We have previously demonstrated that the peptides derived from the receptor binding region identical to those used in this study compete with ApoE for receptor binding (Misra et al., 2001). In fact, ApoE has been demonstrated to initiate a signaling cascade in both neurons and macrophage (Misra et al., 2001; Muller et al., 1998).

A recent report has demonstrated that the LRP receptor is capable of initiating a calcium signaling response mediated by the NMDA receptor (Bacskai et al., 2000). Although the exact mechanism by which this occurs remains undefined, the authors speculate on the presence of a neuron-specific intracellular adaptor protein that modulates NMDA activity following ligand binding and dimerization of the LRP receptor, and this conceivably could lead to a protective response downstream from the NMDA receptor. Interestingly, recent observations have suggested that the presence of receptor-associated protein (RAP), which blocks all known LRP interactions, does not reverse the neuroprotective effects of ApoE in a cell culture paradigm of NMDA excitotoxicity (Aono et al., 2002).

In the native holoprotein, the receptor binding region is in an a helical conformation. To confirm that the peptide fragments used in our studies were capable of adopting this structure, we performed circular dichroism (CD) experiments. Each of the three peptides tested had a significant helical population in solution, approximating 12-14%. Furthermore, these peptides behave as monomers in solution, and any helical structure is intrinsic to the peptide, and not due to self-association into helical oligomers (Laskowitz et al., 2001). Our results are consistent with the possibility that the free peptides are capable of adopting a helical conformation, which may be stabilized upon receptor binding.

Clearly, the degree of helicity is not the only determinant of bioactivity, as both the functional (apoE 133-149; apoE 136-149) and non-functional (apoE 139-149) peptides had comparable helicity. Thus, the neuroprotective effects of these ApoE-mimetic peptides also appear to be dependent on the specific amino acid sequence and size. In particular, the 17 amino acid peptide derived from residues 133-149 of the apoE receptor-binding region completely blocked the toxicity of NMDA exposure, whereas the 14 amino peptide (apoE 136-149) had reduced efficacy, and the 11 amino acid sequence (apoE 139-149) lost all biological activity in this regard. This suggests that residues 133-139 are essential for bioactivity. Interestingly, this domain is identical to that required for downregulation of glial activation (Laskowitz et al., 2001).

It is noteworthy that the peptides used in this study are derived from the receptor-binding region, and do not include residues 112 and 158, which are the polymorphic regions associated with the different human apoE isoforms. Thus, although the current studies do not directly address the association between apoE isoform and human disease, it is certainly plausible that amino acid substitutions distant from the receptor binding region may affect the conformation of this region, and subsequent apoE-receptor interactions. For example, the substitution of cysteine for arginine at position 158 significantly reduces the ability of ApoE2 to bind the LDL receptor, even though this polymorphism lies outside of the receptor binding region (Weisgraber et al., 1982).

Our results are in contrast to the reports of other groups, who have recently suggested that the ApoE peptide fragments may cause neuronal injury. For example, it has recently been demonstrated that carboxyl-terminal truncated forms of ApoE occur in the brains of patients with AD, presumably as a result of intracellular processing. These fragments are bioactive and are capable of interacting with cytoskeletal proteins to induce inclusions resembling neurofibrillary tangles in cultured neurons (Huang et al., 2001).

Our observation that peptides derived from the ApoE protein are capable of conferring neuroprotection against NMDA induced excitotoxicity is also in contrast to other recent observations. The majority of these studies utilized tandem repeats derived from the receptor-binding region of apoE. In particular, an eighteen amino acid peptide comprised of tandem repeats of residues 141-149 increases intracellular $Ca^{2+}$ and regulates tau phosphorylation via two separate mechanisms: activation of a cell surface $Ca^{2+}$ channel, and release of internal $Ca^{2+}$ stores via a pertussis-toxin sensitive pathway (Wang and Gruenstein, 1997). Using a peptide comprised of a tandem repeat of residues 141-149, Tolar et al. demonstrated that exposure of primary hippocampal neurons to this peptide induced neuronal cell death, an effect which was blocked by preincubation with MK-801 (Tolar et al., 1999). These results predict that exposure with the tandem repeat peptide would amplify NMDA-induced excitotoxicity by direct or indirect mechanisms. It is worth noting, however, that this tandem repeat peptide is substantively different than the peptides used in the current study. A recent report (Moulder et al., 1999) observed that neuronal cell death induced by this tandem repeat may occur via a different mechanism than neuronal death induced by the holoprotein, suggesting that this tandem repeat may not be a biologically relevant model of the intact ApoE protein.

In summary, we report that small peptides derived from the receptor-binding region of ApoE block the calcium influx and neurotoxicity associated with exposure of primary neocortical cultures to NMDA. The in vivo relevance of these findings is consistent with the clinical observations that ApoE appears to modulate neurological recovery from ischemic and hemorrhagic stroke, as well as the global cerebral hypoperfusion associated with cardiopulmonary bypass and post-cardiac arrest resuscitation. Although the neuroprotection observed with these peptides is greater than the modest benefit observed following exposure to the intact ApoE protein, these observations suggest that one mechanism by which endogenous ApoE may affect recovery from ischemic injury is by protecting against glutamate excitotoxicity. The use of these ApoE-mimetic peptides should have therapeutic implications, as well as provide further insight into the neurobiology of this protein in brain subjected to an ischemic or traumatic insult.

EXAMPLE 13

Suppression of LPS-Induced TNF-a and IL-6 Production by ApoE Mimetic Peptides

Septic shock is the most common cause of death in intensive care units, and represents a significant unmet medical challenge. Lipopolysaccharide (LPS) is a primary mediator of gram negative sepsis, and the upregulation of inflammatory cytokines induced by LPS plays an important role in mediating the systemic inflammatory response associated with sepsis. Intravenous administration of LPS is a common animal model of gram negative septic shock, and replicates the clinically relevant systemic inflammatory response. In particular, intravenous administration of LPS causes early upregulation of TNFα and IL-6, which are macrophage-derived cytokines that play an important role in mediating systemic inflammation.

We now demonstrate that injection of ApoE (133-149) suppresses serum levels of TNFα and IL-6 following LPS administration. In these methods, 14-16 week old male C57-BL6 mice were injected with LPS (11.25 μg in 150 μl sterile isotonic saline, or 375 μg/kg) via the tail vein, and then immediately with vehicle (isotonic sterile saline) or ApoE (133-149) (at a dose of 200 μg, in 100 μl, or 6.6 mg/kg, prepared in isotonic saline). Serum samples were obtained in both LPS+vehicle and LPS+peptide groups (n=10 animals/group) at the following timepoints: time 0 (prior to injection), 1 hour, 3 hour and 24 hours after injection. Blood was collected by transcardial puncture, and allowed to clot for 30 minutes. Serum samples, obtained after centrifugation at 16,000 g for 5 minutes, were screened by solid phase ELISA for TNFα and IL-6. There were 20 animals per time point.

Figure 17:
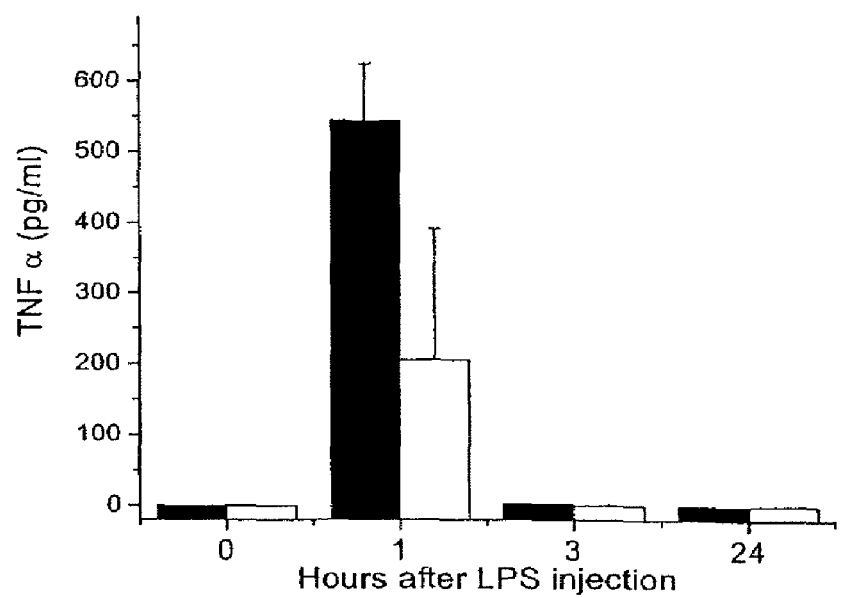
FIG. 17 contains graphs depicting the suppression of LPS-induced serum levels of TNFα (A) and IL-6 (B) by ApoE peptide (133-149). The dark bars represent vehicle-treated animals and the light bars represent peptide-treated animals.
Figure 17:
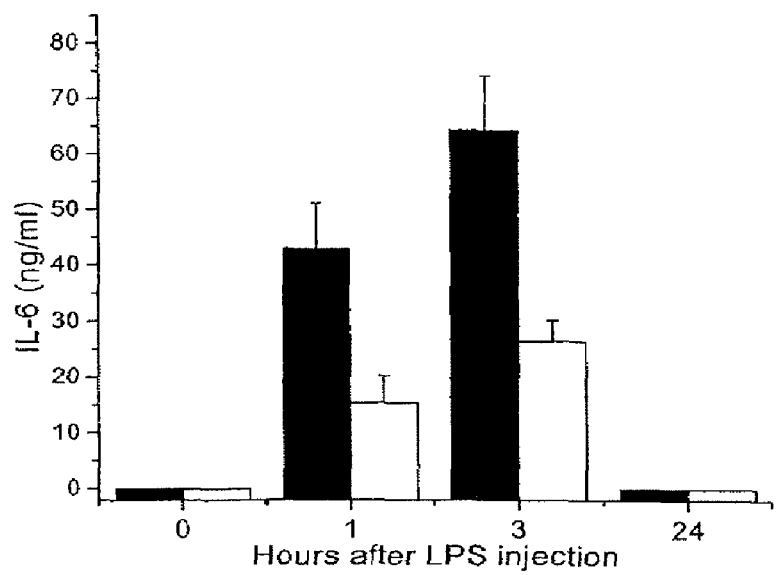

At 1 hour post-injection, serum TNFα was significantly reduced as a function of whether animals received LPS+ vehicle or LPS+apoE peptide (FIG. 17A). At 3 hrs and at baseline, TNFα levels were not measurable. At 1 and 3 hours post-injection, serum IL-6 levels were significantly reduced as a function of whether animals received LPS+vehicle or LPS+apoE peptide (FIG. 17B). At 24 hrs and at baseline, IL-6 levels were not measurable. This data reveals that ApoE (133-149) suppresses TNFα and IL-6 production in the presence of LPS, and therefore suggests that ApoE mimetic peptides may have therapeutic potential in the clinical setting in patients with early sepsis.

REFERENCES

All references and patents cited herein are herein incorporated by reference in their entireties, including, but not limited to, the following:

Alberts et al., *Stroke* 27:183 (abstract) (1996).
Alberts et al., ApoE genotype and survival from intracerebral haemorrhage, *Lancet* 346: 575 (1995).
Amador et al., Serum lactate dehydrogenase activity: an analytical assessment of current assays, *Clin. Chem.* 9: 391-4 (1963).
Aono, et al. (in press). Apolipoprotein E protects against NMDA excitotoxicity. *Neurobiol. Dis.*
Avila et al., *J. Biol. Chem.* 257:5900 (1982).
Bacskai, et al., The endocytic receptor protein LRP also mediates neuronal calcium signaling via N-methyl-D-aspartate receptors. *Proc. Natl. Acad. Sci.* 97:11551-11556 (2000).

Barger and Harmon, *Nature* 388:878 (1997).

Bart, et al., Regional cerebral blood flow in apolipoprotein E deficient vs wildtype mice undergoing middle cerebral artery occlusion. *Neuroreport* 11:2615-2620 (1998).

Bell et al., Upregulation of the macrophage scavenger receptor in response to different forms of injury in the CNS, *J. Neurocytol.* 23(10):605-13 (1994).

Berliner et al., *Circulation* 91:2488 (1995).

Bi et al., Uptake and pathogenic effects of amyloid beta peptide 1-42 are enhanced by integrin antagonists and blocked by NMDA receptor antagonists, *Neuroscience* 112 (4):827-40 (2002).

Bi, et al., N-methyl-D-aspartate receptor subunit NR2A and NR2B messenger RNA levels are altered in the hippocampus and entorhinal cortex in Alzheimer's disease, *J. Neurol. Sci.* 200(1-2):11-8 (2002).

Breitner et al., *Neurobiol. Aging* 16:523 (1995).

Broderick, et al., Apolipoprotein E phenotype and the efficacy of intravenous tissue plasminogen activator in acute ischemic stroke. *Ann. Neurol.* 49:736-744 (2001).

Cady, Understanding opioid tolerance in cancer pain, *Oncol. Nurs. Forum* 28(10):1561-8 (2001).

Calabresi, Considerations in the treatment of relapsing-remitting multiple sclerosis, *Neurology* 58(8 Suppl 4):S10-22 (2002).

Chensue et al., *Am. J. Pathol.* 138:395-402 (1991).

Clifford, AIDS dementia, *Med. Clin. North Am.* 86(3):537-50, vi (2002).

Cohen et al., Interaction of lactoferrin and lipopolysaccharide (LPS): effects on the antioxidant property of lactoferrin and the ability of LPS to prime human neutrophils for enhanced superoxide formation, *J. Infect. Dis.* 166:1375-1378 (1992).

Connolly et al., *Stroke* 27:174 (abstract) (1996).

Corder et al., Gene doses of apolipoprotein E type 4 allele and the risk of Alzheimer's disease in late onset families. *Science* 261:921-923 (1993).

Dhib-Jalbut, Mechanisms of action of interferons and glatiramer acetate in multiple sclerosis, *Neurology* 58(8 Suppl 4):S3-9 (2002).

Doble, The role of excitotoxicity in neurodegenerative disease: implications for therapy, *Pharmacol. Ther.* 81(3):163-221 (1999).

Dunlop et al., HIV dementia and apolipoprotein E, *Acta Neurol. Scand.* 95(5):315-8 (1997).

Dyer et al., *J. Biol. Chem.* 266:15009 (1991).

Edgington and Curtiss, *Cancer Res.* 41:3786 (1981).

Farber et al., Antiepileptic drugs and agents that inhibit voltage-gated sodium channels prevent NMDA antagonist neurotoxicity, *Mol. Psychiatry.* 7(7):726-33 (2002).

Fazio et al., *Proc. Natl. Acad. Sci.* 94:4647 (1997).

Flaherty et al., Regulation of tau phosphorylation in microtubule fractions by apolipoprotein E, *J. Neurosci. Res.* 56(3):271-4 (1999).

Friedman et al., G., Apolipoprotein E-epsilon 4 genotype predicts a poor outcome in survivors of traumatic brain injury. *Neurology* 52:244-248 (1999).

Gehrmenn et al., Microglia: intrinsic immuneffector cell of the brain, *Brain Res. Brain Res. Rev.* 20(3):269-87 (1995).

Giulian et al., *J. Neuroscience,* 16:3139 (1996).

Griffin et al., *J Neuropath. Exp. Neurol.* 54:276 (1995).

Hansson, *Basic Res. Cardiol.,* 89(1):41 (1994).

Harris et al., *Hepatol.* 27:1341-48 (1998).

Harris et al., *J. Clin. Invest.* 91:1028-34 (1993).

Haughey et al., HIV-1 Tat through phosphorylation of NMDA receptors potentiates glutamate excitotoxicity, *J. Neurochem.* 78(3):457-67 (2001).

Henderson et al., *Microbiol. Rev.* 60:316-34 (1996).

Holtzman et al., Low density lipoprotein receptor-related protein mediates apolipoprotein E-dependent neurite outgrowth in a central nervous system-derived neuronal cell line. *Proc. Natl. Acad. Sci.* 92:9480-9484 (1995).

Horsburgh et al., Increased neuronal damage in apolipoprotein E-deficient mice following global ischaemia. *Neuroreport* 10:837-841 (1999).

Horsburgh et al., Intraventricular infusion of apolipoprotein E ameliorates acute neuronal damage after global cerebral ischemia in mice. *J. Cereb. Blood Flow Metab.* 20:458-62 (2000).

Huang et al., Apolipoprotein E fragments present in Alzheimer's Disease brains induce neurofibrillary tangle-like intracellular inclusions in neurons. *Proc. Natl. Acad. Sci. USA* 91:11183-11186 (2001).

Huettinger et al., Characteristics of chylomicron remnant uptake into rat liver, *Clin. Biochem.* 21(2):87-92 (1988).

Innerarity et al., *J. Biol. Chem.* 254:4186-4190 (1979).

Innerarity et al., The receptor-binding domain of human apolipoprotein E: binding of apolipoprotein E fragments, *J. Biol. Chem.* 258:12341-47 (1983).

Jones et al., Attenuation of acute morphine withdrawal in the neonatal rat by the competitive NMDA receptor antagonist LY2359592002, *Neuropsychopharmacology* 26(3):301-10 (2002).

Jordan et al., Isoform-specific effect of apolipoprotein E on cell survival and beta-amyloid-induced toxicity in rat hippocampal pyramidal neuronal cultures, *J. Neurosci.* 18:195-204 (1998).

Jordan et al., Apolipoprotein E epsilon-4 associated with chronic traumatic brain injury in boxing, *JAMA* 278:136-140 (1997).

Kim et al., Human apolipoprotein E receptor 2. J. Biol. Chem. 271, 8373-8380 (1996). Klopman and Sedykh, An MCASE approach to the search of a cure for Parkinson's Disease, *BMC Pharmacol.* 2(1):8 (2002).

Kolker et al., NMDA receptor activation and respiratory chain complex V inhibition contribute to neurodegeneration in d-2-hydroxyglutaric aciduria, *Eur. J. Neurosci.* 16(1):21-8 (2002).

Kotlinska, NMDA antagonists inhibit the development of ethanol dependence in rats, *Pol. J. Pharmacol.* 2001 January-February; 53(1):47-50 (2001).

Krieger and Herz, Structures and functions of multiligand lipoprotein receptors: macrophage scavenger receptors and LDL receptor-related protein (LRP), *Annual Review of Biochemistry.* 63:601-37 (1994).

Kudo et al., Absence of direct antioxidant effects from volatile anesthetics in mixed neuronal-glial culture, *Anesthesiology* 94:303-312 (2001).

Lalazar et al., Site-specific mutagenesis of human apolipoprotein E. Receptor binding activity of variants with single amino acid substitutions. *J. Biol. Chem.* 263:3542-3545 (1998).

Laskowitz et al., *J. Neuroimmunol.* 76:70 (1997).

Laskowitz et al., Apolipoprotein E-deficient mice have increased susceptibility to focal cerebral ischemia. *J. Cereb. Blood Flow Metab.* 17:753-758 (1997).

Laskowitz et al., Downregulation of microglial activation by Apolipoprotein E and apoE-mimetic peptides, *Exp. Neurol.* 167:74-85 (2001).

Le and Lipton, Potential and current use of N-methyl-D-aspartate (NMDA) receptor antagonists in diseases of aging, *Drugs Aging* 18(10):717-24 (2001).

Lendon et al., No effect of apolipoprotein E on neuronal cell death due to excitotoxic and apoptotic agents in vitro and neonatal hypoxic ischaemia in vivo, *Euro. J. Neurosci.* 12:2235-2242 (2000).

Linton et al., Phenotypes of apolipoprotein B and apolipoprotein E after liver transplantation, *J. Clin. Invest.* 270-81 (1991).

Linton et al., *Science,* 267:1034 (1995).

Lovestone et al., Apolipoprotein E gene and Alzheimer's disease: is tau the link? *Biochem. Soc. Symp.* (67):111-20 (2001).

Lynch et al., Apolipoprotein E modulates glial activation and the endogenous central nervous system inflammatory response. *J. Neuroimmunol.* 114:107-113 (2001).

Matsubara et al., Monoclonal antibodies against inflammatory mediators for the treatment of patients with sepsis, *Nippon Rinsho* 60(3):578-84 (2002).

Mayeux et al., *Neurology* 45:555 (1995).

McArron et al., The apolipoprotein E epsilon4 allele and outcome in cerebrovascular disease. *Stroke* 29:1882-1887 (1998).

McGeer et al., *Glia* 7:88 (1993).

McKenna and Melzack, Blocking NMDA receptors in the hippocampal dentate gyrus with AP5 produces analgesia in the formalin pain test, *Exp. Neurol.* 172(1):92-9 (2001).

Meldrum et al., Excitatory amino acid neurotoxicity and neurodegenerative disease. *Trends Pharmacol. Sci.* 11:379-387 (1990).

Misra et al. The relationship between low density lipoprotein-related protein/alpha 2-macroglobulin (alpha 2M) receptors and the newly described alpha 2M signaling receptor. *Journal of Biological Chemistry.* 269(28):18303-6 (1994).

Misra et al., Apolipoprotein E and apoE-mimetic peptides initiate a calcium dependent signaling response in macrophage. *J. Leukoc. Biol.* 70:677-683 2001).

Miyata et al., Apolipoprotein E allele-specific antioxidant activity and effects on cytotoxicity by oxidative insults and beta-amyloid peptides. *Nature Genet.* 14:55-61 (1996).

Miyazawa et al., Lactoferrin-lipopolysaccharide interactions. Effect of lactoferrin binding to monocyte/macrophage-differentiated HL-60 cells, *J. Immunol.* 146:723-729 (1991).

Moulder et al., Analysis of a novel mechanism of neuronal toxicity produced by an apolipoprotein E-derived peptide. *J. Neurochem.* 72:1069-1080 (1999).

Muller et al., Apolipoprotein E isoforms increase intracellular $Ca^{2+}$ differentially through a omega-agatoxin IVa-sensitive $Ca^{2+}$-channel. *Brain Pathol.,* 8:641-53 (1998).

Myers et al., Helix propensities are identical in proteins and peptides. *Biochemistry* 36:10923-10929 (1997).

Mytilineou et al., L-deprenyl protects mesencephalic dopamine neurons from glutamate receptor-mediated toxicity in vitro, *J. Neurochem.* 68(1):33-9 (1997).

Newman et al., *Ann. Thorac. Surg.* 59:1326 (1995).

Nguimfack, Do the glutamate excitotoxicity theory and potential free radicals implication in schizophrenia aetiopathogenesis provide a new enlightenment to links between: genome, environment and biology in the determinism of that disorder? *Encephale* 28(2):147-53 (2002).

Nicoll et al., *Nat. Med.* 1:135 (1995).

Novak et al., A new low density lipoprotein receptor homologue with 8 binding ligand repeats in brain of chicken and mouse. *J. Biol. Chem.* 271:11732-11736 (1996).

Paul and Bolton, Modulation of blood-brain barrier dysfunction and neurological deficits during acute experimental allergic encephalomyelitis by the N-methyl-D-aspartate receptor antagonist memantine, *J. Pharmacol. Exp. Ther.* 302(1):50-7 (2002).

Pearlstein et al., Neuroprotective effects of NMDA receptor glycine recognition site antagonism: dependence on glycine concentration. *J. Neurochem.* 70:2012-2019 (1998).

Perez et al., Evaluation of HIV-1 Tat induced neurotoxicity in rat cortical cell culture, *J. Neurovirol.* 7(1):1-10 (2001).

Rao et al., Neuroprotection by memantine, a non-competitive NMDA receptor antagonist after traumatic brain injury in rats, *Brain Res.* 911(1):96-100 (2001).

Regner et al., Neurochemical characterization of traumatic brain injury in humans, *J. Neurotrauma* 18(8):783-92 (2001).

Rensen et al., Human recombinant apolipoprotein E redirects lipopolysaccharide from Kupffer cells to liver parenchymal cells in rats in vivo, *J. Clin. Invest.* 99(10):2438-45 (1997).

Rogers et al., *Neurology* 43:1609 (1993).

Rothwell and Relton, *Cerebrovasc. Brain Metab. Rev.* 5:178 (1993).

Schiefer et al., Riluzole prolongs survival time and alters nuclear inclusion formation in a transgenic mouse model of Huntington's disease, *Mov. Disord.* 17(4):748-57 (2002).

Schiefermeier et al., Apolipoprotein E polymorphism. Survival and neurological outcome after cardiopulmonary resuscitation. *Stroke* 21: 2068-2071 (2000).

Seliger et al., *Neurology* (Abstract) page A213 (1997).

Sheng et al., *J. Neurochem* 63:1872 (1994).

Sheng et al., Apolipoprotein E deficiency worsens outcome from global ischemia in the mouse. *Stroke* 30:1118-1123 (1999).

Sheng et al., Apolipoprotein E isoform specific differences in outcome from focal ischemia in transgenic mice. *J. Cereb. Blood Flow Metab.* 18:361-366 (1998).

Slooter et al., Apolipoprotein E4 and risk of dementia with stroke, a population-based investigation. *JAMA* 227:818-821 (1997).

Sorbi et al., *Neurology* 46:A307 (abstract) (1996).

Sorbi et al., ApoE as a prognostic factor for post-traumatic coma. *Nat. Med.* 1:852 (1995).

Soyka et al., NMDA receptor challenge with dextromethorphan-subjective response, neuroendocrinological findings and possible clinical implications, *J. Neural. Transm.* 107(6):701-14 (2000).

Stoll and Mueller, *Neurosci. Lett.* 72:233 (1986).

Stoll et al., *Glia* 2:170 (1989).

Strittmatter et al., Apolipoprotein-e-epsilon-4 allele distributions in late-onset alzheimers disease and in other amyloid-forming diseases. *Proc. Natl. Acad. Sci. USA* 90:1977-81 (1993).

Tardiff et al., Preliminary report of a genetic basis for cognitive decline after cardiac operations. The Neurologic Outcome Research Group of the Duke Heart Center, *Ann. Thorac. Surg.* 64:715-20 (1997).

Teasdale et al., G. M., Nicoll, J. A., Murray, G., Fiddes, M., 1997. Association of apolipoprotein E polymorphism with outcome after head injury, *Lancet* 350, 1069-1071.

Tesseur et al., Expression of human apolipoprotein E4 in neurons causes hyperphosphorylation of protein tau in the brains of transgenic mice, *Am. J. Pathol.* 156(3):951-64 (2000).

Tolar et al., Truncated apolipoprotein E (ApoE) causes increased intracellular calcium and may mediate apoE neurotoxicity. *J. Neurosci.* 19:7100-7110 (1999).

Tolar et al., Neurotoxicity of the 22 kDa thrombin-cleavage fragment of apolipoprotein E and related synthetic peptides is receptor-mediated. *J. Neurosci.* 17:5678-5686 (1997).

Van Oosten et al., Apolipoprotein E protects against bacterial lipopolysaccharide-induced lethality, *J. Biol. Chem.* 276 (12):8820-24 (2001).

Veinbergs et al., Role of apolipoprotein E receptors in regulating the differential in vivo neurotrophic effects of apolipoprotein E, *Exp. Neurol.* 170(1):15-26 (2001).

Von Bergen et al., Effect of intrathecal non-NMDA EAA receptor antagonist LY293558 in rats: a new class of drugs for spinal anesthesia, *Anesthesiology* 97(1):177-82 (2002).

Waage et al., *J. Exp. Med.* 169:333-38 (1987).

Wang et al., Apolipoprotein E (ApoE) peptide regulates tau phosphorylation via two different signaling pathways. *J. Neurosci. Res.* 51:658-665 (1998).

Wang et al., Rapid elevation of neuronal cytoplasmic calcium by apolipoprotein E peptide. *J. Cell. Physiol.* 173:73-83 (1997).

Watanabe et al., *Int. J. Cardiol.* 54:551 (1997).

Weisbarger et al., The receptor-binding domain of human apolipoprotein E: monoclonal antibody inhibition of binding, *J. Biol. Chem.* 258:12348-54 (1983).

Weisgraber et al., Abnormal lipoprotein receptor-binding activity of the human E apoprotein due to cysteine-arginine interchange at a single site. *J. Biol. Chem.* 257:2518-2521 (1982).

Weisgraber Apolipoprotein E: Structure-function relationships. *Adv. Protein Chem.* 45:249-302 (1994).

Wettereau et al., Human apolipoprotein E3 is aqueous solution. Evidence for two structural domains, *J. Biol. Chem.* 263:6240-48 (1988).

Wisniewski et al., Apolipoprotein E: a pathological chaperone in patients with cerebral and systemic amyloid. *Neurosci. Let.* 135:235-238 (1992).

Xu and Luo, Relationship between changes of N-methyl-D-aspartate receptor activity and brain edema after brain injury in rats, *Clin. J. Traumatol.* 4(3):135-8 (2001).

Zanotti et al., Cytokine modulation in sepsis and septic shock, *Expert Opin. Investig. Drugs* 11(8):1061-75 (2002).

---

That which is claimed is:

1. A method of treating or reducing the inflammation associated with sepsis in a subject in need thereof, comprising administering to the subject a composition comprising an ApoE peptide, wherein said ApoE peptide is a peptide of 18 to 50 amino acids comprising the sequence of SEQ ID NO: 10, and wherein said composition is administered in an amount sufficient to reduce serum levels of inflammatory cytokines in the subject as compared to that which would occur in the absence of said composition.

2. The method of claim 1, wherein said inflammatory cytokines include TNFα or IL-6.

3. The method of claim 1, wherein said composition is administered concurrently or sequentially with one or more anti-inflammatory cytokines or monoclonal antibodies.

4. The method of claim 3, wherein said anti-inflammatory cytokines are selected from the group consisting of IL-10, transforming growth factor-beta, granulocyte colony-stimulating factor, IFN-phi, macrophage migration inhibitory factor and high mobility group 1 protein.

5. The method of claim 3, wherein said monoclonal antibodies are selected from the group consisting of antiendotoxin antibodies, anti-tumor necrosis factor antibodies, and anti-CD14 antibodies.

6. A method of treating or reducing the inflammation associated with sepsis in a subject, comprising administering a composition comprising an ApoE peptide, wherein said ApoE peptide consists of the sequence of SEQ ID NO: 10, and wherein said composition is administered in an amount sufficient to reduce serum levels of inflammatory cytokines in the subject as compared to that which would occur in the absence of the composition.

* * * * *

SEQUENCE LISTING

```
<160> NUMBER OF SEQ ID NOS: 14

<210> SEQ ID NO 1
<211> LENGTH: 16
<212> TYPE: PRT
<213> ORGANISM: Artificial sequence
<220> FEATURE:
<223> OTHER INFORMATION: fragment of ApoE containing LDL receptor
      binding site

<400> SEQUENCE: 1

His Leu Arg Lys Leu Arg Lys Arg Leu Leu Arg Asp Ala Asp Asp Leu
1               5                   10                  15

<210> SEQ ID NO 2
<211> LENGTH: 9
<212> TYPE: PRT
<213> ORGANISM: Artificial sequence
<220> FEATURE:
<223> OTHER INFORMATION: fragment of ApoE containing LDL receptor
      binding site

<400> SEQUENCE: 2

Leu Arg Lys Leu Arg Lys Arg Leu Leu
1               5

<210> SEQ ID NO 3
<211> LENGTH: 18
<212> TYPE: PRT
<213> ORGANISM: Artificial sequence
<220> FEATURE:
<223> OTHER INFORMATION: fragment of ApoE containing LDL receptor
      binding site

<400> SEQUENCE: 3

Leu Arg Lys Leu Arg Lys Arg Leu Leu Leu Arg Lys Leu Arg Lys Arg
1               5                   10                  15

Leu Leu

<210> SEQ ID NO 4
<211> LENGTH: 31
<212> TYPE: PRT
<213> ORGANISM: Artificial sequence
<220> FEATURE:
<223> OTHER INFORMATION: fragment of ApoE containing LDL receptor
```

-continued binding site

<400> SEQUENCE: 4

Thr Glu Glu Leu Arg Val Arg Leu Ala Ser His Leu Arg Lys Leu Arg
1               5                   10                  15

Lys Arg Leu Leu Arg Asp Ala Asp Asp Leu Gln Lys Leu Ala
            20                  25                  30

<210> SEQ ID NO 5
<211> LENGTH: 31
<212> TYPE: PRT
<213> ORGANISM: Artificial sequence
<220> FEATURE:
<223> OTHER INFORMATION: fragment of ApoE containing LDL receptor
      binding site

<400> SEQUENCE: 5

Thr Glu Glu Leu Arg Val Arg Leu Ala Ser His Leu Arg Lys Leu Arg
1               5                   10                  15

Lys Arg Leu Leu Arg Asp Ala Asp Asp Leu Gln Lys Cys Leu Ala
            20                  25                  30

<210> SEQ ID NO 6
<211> LENGTH: 20
<212> TYPE: PRT
<213> ORGANISM: Artificial sequence
<220> FEATURE:
<223> OTHER INFORMATION: fragment of ApoE containing LDL receptor
      binding site

<400> SEQUENCE: 6

Thr Glu Glu Leu Arg Val Arg Leu Ala Ser His Leu Arg Lys Leu Arg
1               5                   10                  15

Lys Arg Leu Leu
            20

<210> SEQ ID NO 7
<211> LENGTH: 31
<212> TYPE: PRT
<213> ORGANISM: Artificial sequence
<220> FEATURE:
<223> OTHER INFORMATION: fragment of ApoE containing LDL receptor
      binding site

<400> SEQUENCE: 7

Thr Glu Glu Leu Arg Val Arg Leu Ala Arg His Leu Arg Lys Leu Arg
1               5                   10                  15

Lys Arg Leu Leu Arg Asp Ala Asp Asp Leu Gln Lys Arg Leu Ala
            20                  25                  30

<210> SEQ ID NO 8
<211> LENGTH: 31
<212> TYPE: PRT
<213> ORGANISM: Artificial sequence
<220> FEATURE:
<223> OTHER INFORMATION: fragment of ApoE containing LDL receptor
      binding site

<400> SEQUENCE: 8

Thr Glu Glu Leu Arg Val Arg Leu Ala Arg His Leu Arg Lys Leu Arg
1               5                   10                  15

Lys Arg Leu Leu Arg Asp Ala Asp Asp Leu Gln Lys Cys Leu Ala
            20                  25                  30

<210> SEQ ID NO 9

```
<211> LENGTH: 20
<212> TYPE: PRT
<213> ORGANISM: Artificial sequence
<220> FEATURE:
<223> OTHER INFORMATION: fragment of ApoE containing LDL receptor
      binding site

<400> SEQUENCE: 9

Thr Glu Glu Leu Arg Val Arg Leu Ala Arg His Leu Arg Lys Leu Arg
1               5                   10                  15

Lys Arg Leu Leu
            20

<210> SEQ ID NO 10
<211> LENGTH: 17
<212> TYPE: PRT
<213> ORGANISM: Homo sapiens
<220> FEATURE:
<221> NAME/KEY: misc_feature
<223> OTHER INFORMATION: fragment of receptor-binding domain of human
      ApoE

<400> SEQUENCE: 10

Leu Arg Val Arg Leu Ala Ser His Leu Arg Lys Leu Arg Lys Arg Leu
1               5                   10                  15

Leu

<210> SEQ ID NO 11
<211> LENGTH: 14
<212> TYPE: PRT
<213> ORGANISM: Homo sapiens
<220> FEATURE:
<221> NAME/KEY: misc_feature
<223> OTHER INFORMATION: fragment of receptor-binding domain of human
      ApoE

<400> SEQUENCE: 11

Arg Leu Ala Ser His Leu Arg Lys Leu Arg Lys Arg Leu Leu
1               5                   10

<210> SEQ ID NO 12
<211> LENGTH: 11
<212> TYPE: PRT
<213> ORGANISM: Homo sapiens
<220> FEATURE:
<221> NAME/KEY: misc_feature
<223> OTHER INFORMATION: fragment of receptor-binding domain of human
      ApoE

<400> SEQUENCE: 12

Ser His Leu Arg Lys Leu Arg Lys Arg Leu Leu
1               5                   10

<210> SEQ ID NO 13
<211> LENGTH: 21
<212> TYPE: PRT
<213> ORGANISM: Homo sapiens
<220> FEATURE:
<221> NAME/KEY: misc_feature
<223> OTHER INFORMATION: fragment of receptor-binding domain of human
      ApoE

<400> SEQUENCE: 13

Thr Glu Glu Leu Arg Val Arg Leu Ala Ser His Leu Arg Lys Leu Arg
1               5                   10                  15

Lys Arg Leu Leu Arg
            20
```

```
<210> SEQ ID NO 14
<211> LENGTH: 17
<212> TYPE: PRT
<213> ORGANISM: Artificial sequence
<220> FEATURE:
<223> OTHER INFORMATION: Synthetic peptide:  scrambled control peptide

<400> SEQUENCE: 14

Leu Ala Arg Lys Leu Arg Ser Arg Leu Val His Leu Arg Leu Lys Leu
1               5                   10                  15

Arg
```